(12) United States Patent
Campbell et al.

(10) Patent No.: US 11,512,113 B2
(45) Date of Patent: Nov. 29, 2022

(54) CLEAVABLE LINKER COMPOSITIONS AND METHODS

(71) Applicant: Janux Therapeutics, Inc., San Diego, CA (US)

(72) Inventors: David Campbell, San Diego, CA (US); Thomas R. DiRaimondo, San Diego, CA (US)

(73) Assignee: JANUX THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 17/398,500

(22) Filed: Aug. 10, 2021

(65) Prior Publication Data

US 2022/0048949 A1    Feb. 17, 2022

Related U.S. Application Data

(60) Provisional application No. 63/064,268, filed on Aug. 11, 2020.

(51) Int. Cl.
| C07K 7/08 | (2006.01) |
| A61K 47/65 | (2017.01) |
| A61K 47/68 | (2017.01) |

(52) U.S. Cl.
CPC ............. C07K 7/08 (2013.01); A61K 47/65 (2017.08); A61K 47/68 (2017.08); A61K 47/6889 (2017.08)

(58) Field of Classification Search
None
See application file for complete search history.

(56) References Cited

U.S. PATENT DOCUMENTS

| | | |
|---|---|---|
| 4,694,778 A | 9/1987 | Learn et al. |
| 9,453,078 B2 | 9/2016 | Stagliano et al. |
| 9,562,073 B2 | 2/2017 | Moore et al. |
| 10,118,961 B2 | 11/2018 | Stagliano et al. |
| 10,138,272 B2 | 11/2018 | Moore et al. |
| 11,028,126 B2 | 6/2021 | Moore et al. |
| 2001/0031264 A1 | 10/2001 | Segal |
| 2016/0193332 A1* | 7/2016 | Lowman .......... A61P 17/06 424/9.6 |
| 2016/0194399 A1 | 7/2016 | Irving et al. |
| 2016/0355599 A1 | 12/2016 | Sagert et al. |
| 2017/0196996 A1 | 7/2017 | Lowman et al. |
| 2017/0369563 A1 | 12/2017 | Dubridge et al. |
| 2018/0125988 A1 | 5/2018 | Yang et al. |
| 2019/0153115 A1 | 5/2019 | Schellenberger et al. |
| 2019/0359714 A1 | 11/2019 | Tipton et al. |
| 2021/0002343 A1 | 1/2021 | Karow et al. |
| 2021/0020264 A1 | 1/2021 | Stroh et al. |
| 2021/0054077 A1 | 2/2021 | Schellenberger et al. |

FOREIGN PATENT DOCUMENTS

| | | |
|---|---|---|
| WO | WO-2007147001 A2 | 12/2007 |
| WO | WO-2008119567 A2 | 10/2008 |
| WO | WO-2014079000 A1 | 5/2014 |
| WO | WO-2016118629 A1 | 7/2016 |
| WO | WO-2019075405 A1 | 4/2019 |
| WO | WO-2019183218 A1 | 9/2019 |
| WO | WO-2020069398 A1 | 4/2020 |
| WO | WO2020118109 A2 * | 6/2020 ............. A61K 38/05 |
| WO | WO-2020247867 A2 | 12/2020 |
| WO | WO-2020247871 A2 | 12/2020 |
| WO | WO-2022035866 A1 | 2/2022 |

OTHER PUBLICATIONS

NCBI WP_048120037.1. Multispecies: sporulation protein [Methanosarcina], https://www.ncbi.nlm.nih.gov/protein/WP_048120037.1?report=genbank&log$=protalign . . . Jan. 22, 2022 (Year: 2022).*
Olson et al. In vivo characterization of activatable cell penetrating peptides for targeting protease activity in cancer. Integr Biol (Camb). Jun. 2009 ; 1(5-6): 382-393. (Year: 2009).*
Liao et al. Activation of lymphocytes by anti-CD3 single-chain antibody dimers expressed on the plasma membrane of tumor cells. Gene Therapy. 2000; 7: 339-347. (Year: 2000).*
PCT/US2021/045395 International Search Report and Written Opinion dated Dec. 10, 2021.
UniProtKB A0A1D2VVTX0. Sporulatioti protein [online] Dec. 11, 2019 [retrieved Nov. 2, 2021], Available on the internet: httias://www.uniprot.org/uniprot/A0A1D2VVIX0.
Altschul et al. Basic Local Alignment Search Tool. J. Mol. Biol. 215: 403-410 (1990).
Altschul, et al. Gapped BLAST and PSI-BLAST: a new generation of protein database search programs. Nucleic Acids Res 25:3389-3402 (1997).
Bird et al. Single-chain antigen-binding proteins. Science 242:423-442 (1988).
Clackson et al. Making antibody fragments using phage display libraries. Nature 352(6336):624-628 (1991).
Colberre-Garapin et al. A new dominant hybrid selective marker for higher eukaryotic cells. J Mol Biol 150:1-14 (1981).
Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).
Goldspiel et al. Human gene therapy. Clin Pharm 12:488-505 (1993).
Hanes et al. In vitro selection and evolution of functional proteins by using ribosome display. PNAS USA 94:4937-4942 (1997).
Huse et al. Generation of a large combinatorial library of the immunoglobulin repertoire in phage lambda. Science 246(4935):1275-1281 (1989).

(Continued)

*Primary Examiner* — Aradhana Sasan
*Assistant Examiner* — Jia-Hai Lee
(74) *Attorney, Agent, or Firm* — Wilson Sonsini Goodrich & Rosati

(57) ABSTRACT

Provided herein are cleavable linkers, pharmaceutical compositions thereof, as well as nucleic acids, and methods for making and discovering the same. The cleavable linkers described herein have improved efficacy and safety.

25 Claims, 15 Drawing Sheets

Specification includes a Sequence Listing.

(56) References Cited

OTHER PUBLICATIONS

Huston et al. Protein engineering of antibody binding sites: recovery of specific activity in an anti-digoxin single-chain Fv analogue produced in *Escherichia coli*. PNAS USA 85(16):5879-5883 (1988).
Karlin, et al. Applications and statistics for multiple high-scoring segments in molecular sequences. PNAS USA 90:5873-5877 (1993).
Karlin et al. Methods for assessing the statistical significance of molecular sequence features by using general scoring schemes. PNAS USA 87: 2264-2268 (1990).
Kessenbrock et al. Matrix metalloproteinases: regulators of the tumor microenvironment. Cell 141(1):52-67 (2010).
Kohler et al. Continuous cultures of fused cells secreting antibody of predefined specificity. Nature 256:495-497 (1975).
Kozbor et al. The production of monoclonal antibodies from human lymphocytes. Immunology Today 4:72-79 (1983).
Lowy et al., Isolation of transforming DNA: Cloning the hamster aprt gene. Cell 22:817-823 (1980).
Morgan et al. Human gene therapy. Ann Rev Biochem 62:191-217 (1993).
Morrison et al. Chimeric human antibody molecules: mouse antigen-binding domains with human constant region domains. PNAS USA 81(21):6851-6855 (1984).
Mulligan et al. Selection for animal cells that express the *Escherichia coli* gene coding for xanthine-guanine phosphoribosyltransferase. PNAS USA 78(4):2072-2076 (1981).
Neuberger et al. Recombinant antibodies possessing novel effector functions. Nature 312(5995):604-608 (1984).
O'Hare et al. Transformation of mouse fibroblasts to methotrexate resistance by a recombinant plasmid expressing a prokaryotic dihydrofolate reductase. PNAS USA 78:1527-1531 (1981).
PCT/US2020/036493 International Invitation to Pay Additional Fees dated Sep. 15, 2020.
PCT/US2020/036493 International Search Report and Written Opinion dated Dec. 21, 2020.
Santerre et al. Expression of prokaryotic genes for hygromycin B and G418 resistance as dominant-selection markers in mouse L cells. Gene 30(1-3):147-156 (1984).
Skerra et al. Assembly of a functional Immunoglobulin Fv fragment in *Escherichia coli*. Science 240(4855):1038-1041 (1988).
Szybalska et al. Genetics of human cell line. IV. DNA-mediated heritable transformation of a biochemical trait. PNAS USA 48:2026-2034 (1962).
Takeda et al. Construction of chimaeric processed immunoglobulin genes containing mouse variable and human constant region sequences. Nature 314(6010):452-454 (1985).
Tolstoshev. Gene Therapy, Concepts, Current Trials and Future Directions. Ann. Rev. Pharmacol. Toxicol. 32:573-596 (1993).
UniProt Accession No. A0A315V0J1 (A0A315V0J1_GAMAF) Gambusia affinis (*Western mosquitofish*) (*Heterandria affinis*) Phosphoinositide phospholipase C; retrieved from https://www.uniprot.org/uniprot/A0A315V0J1 (2018).
Ward et al. Binding activities of a repertoire of single immunoglobulin variable domains secreted from *Escherichia coli*. Nature 341(6242):544-546 (1989).
Wigler et al. Transfer of purified herpes virus thymidine kinase gene to cultured mouse cells. Cell 11:223-232 (1977).
Wigler et al. Transformation of mammalian cells with an amplifiable dominant-acting gene. PNAS USA 77:3567-3570 (1980).
Wootton et al. Statistics of local complexity in amino acid sequences and sequence databases. Computers & Chemistry 17(2):149-163 (Jun. 1993).
Wu et al. Delivery systems for gene therapy. Biotherapy 3:87-95 (1991).

* cited by examiner

SEQUENCE LISTING

<160> NUMBER OF SEQ ID NOS: 27

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Ser Gly Arg Ser Asp Ala Gly
1               5

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Ser Ser Gly Leu Leu Ser Gly Arg Ser Asp Asn His
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Ser Ser Gly Leu Leu Ser Gly Arg Ser Asp Ala Gly
1               5                   10

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ala Gly Leu Leu Ala Pro Pro Gly Gly Leu Ser Gly Arg Ser Asp
1               5                   10                  15

Ala Gly

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Pro Leu Gly Leu Ser Gly Arg Ser Asp Ala Gly
1               5                   10

<210> SEQ ID NO 6
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Leu Ser Gly Arg Ser Asp Ala Gly Ser Pro Leu Gly Leu Ala Gly
1               5                   10                  15

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gly Gln Ser Gly Gln Leu Ser Cys Glu Gly Trp Ala Met Asn Arg
1               5                   10                  15

Glu Gln Cys Arg Ala
            20

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Pro Cys Arg Ser His Ile Asp Val Ala Lys Pro Ile Cys Val
1               5                   10                  15

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gly Gln Ser Gly Gln Gly Tyr Leu Trp Gly Cys Glu Trp Asn Cys
1               5                   10                  15

Gly Gly Ile Thr Thr
            20

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gly Gln Ser Gly Ser Gly Tyr Leu Trp Gly Cys Glu Trp Asn Cys
1               5                   10                  15

Ala Gly Ile Thr Thr
            20

<210> SEQ ID NO 11
<211> LENGTH: 115
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 11

```
Glu Val Gln Leu Val Glu Ser Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser
        115
```

<210> SEQ ID NO 12
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Gln Gly Gln Ser Gly Gln Leu Ser Cys Glu Gly Trp Ala Met Asn Arg
1               5                   10                  15

Glu Gln Cys Arg Ala Gly Ser Ser Gly Gly Ser Gly Gly Ser Gly Gly
            20                  25                  30

Ser Gly Ile Ser Ser Gly Leu Leu Ser Gly Arg Ser Asp Asn His Gly
        35                  40                  45

Ser Ser Gly Thr Asp Ile Leu Leu Thr Gln Ser Pro Val Ile Leu Ser
50                  55                  60

Val Ser Pro Gly Glu Arg Val Ser Phe Ser Cys Arg Ala Ser Gln Ser
65                  70                  75                  80

Ile Gly Thr Asn Ile His Trp Tyr Gln Gln Arg Thr Asn Gly Ser Pro
            85                  90                  95

Arg Leu Leu Ile Lys Tyr Ala Ser Glu Ser Ile Ser Gly Ile Pro Ser
            100                 105                 110

Arg Phe Ser Gly Ser Gly Ser Gly Thr Asp Phe Thr Leu Ser Ile Asn
        115                 120                 125

Ser Val Glu Ser Glu Asp Ile Ala Asp Tyr Tyr Cys Gln Gln Asn Asn
130                 135                 140

Asn Trp Pro Thr Thr Phe Gly Ala Gly Thr Lys Leu Glu Leu Lys Arg
145                 150                 155                 160

Thr Val Ala Ala Pro Ser Val Phe Ile Phe Pro Pro Ser Asp Glu Gln
                165                 170                 175

Leu Lys Ser Gly Thr Ala Ser Val Val Cys Leu Leu Asn Asn Phe Tyr
            180                 185                 190

Pro Arg Glu Ala Lys Val Gln Trp Lys Val Asp Asn Ala Leu Gln Ser
        195                 200                 205
```

```
Gly Asn Ser Gln Glu Ser Val Thr Glu Gln Asp Ser Lys Asp Ser Thr
        210                 215                 220

Tyr Ser Leu Ser Ser Thr Leu Thr Leu Ser Lys Ala Asp Tyr Glu Lys
225                 230                 235                 240

His Lys Val Tyr Ala Cys Glu Val Thr His Gln Gly Leu Ser Ser Pro
                245                 250                 255

Val Thr Lys Ser Phe Asn Arg Gly Glu Cys
            260                 265

<210> SEQ ID NO 13
<211> LENGTH: 676
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser Gly Gly Gly Gly Ser Gly Gly Gly Ser Gln Gly Gln Ser
        115                 120                 125

Gly Gln Gly Tyr Leu Trp Gly Cys Glu Trp Asn Cys Gly Gly Ile Thr
    130                 135                 140

Thr Gly Ser Ser Gly Gly Ser Gly Gly Ser Gly Gly Ile Ser Ser Gly
145                 150                 155                 160

Leu Leu Ser Gly Arg Ser Asp Asn His Gly Gly Ser Gln Thr Val
                165                 170                 175

Val Thr Gln Glu Pro Ser Leu Thr Val Ser Pro Gly Gly Thr Val Thr
            180                 185                 190

Leu Thr Cys Arg Ser Ser Thr Gly Ala Val Thr Thr Ser Asn Tyr Ala
        195                 200                 205

Asn Trp Val Gln Gln Lys Pro Gly Gln Ala Pro Arg Gly Leu Ile Gly
    210                 215                 220

Gly Thr Asn Lys Arg Ala Pro Gly Thr Pro Ala Arg Phe Ser Gly Ser
225                 230                 235                 240

Leu Leu Gly Gly Lys Ala Ala Leu Thr Leu Ser Gly Val Gln Pro Glu
                245                 250                 255

Asp Glu Ala Glu Tyr Tyr Cys Ala Leu Trp Tyr Ser Asn Leu Trp Val
            260                 265                 270

Phe Gly Gly Gly Thr Lys Leu Thr Val Leu Gly Gly Gly Gly Ser Gly
        275                 280                 285

Gly Gly Gly Ser Gly Gly Gly Gly Ser Glu Val Gln Leu Val Glu Ser
```

-continued

```
                290                 295                 300
Gly Gly Gly Leu Val Gln Pro Gly Gly Ser Leu Lys Leu Ser Cys Ala
305                 310                 315                 320

Ala Ser Gly Phe Thr Phe Asn Thr Tyr Ala Met Asn Trp Val Arg Gln
                325                 330                 335

Ala Pro Gly Lys Gly Leu Glu Trp Val Ala Arg Ile Arg Ser Lys Tyr
            340                 345                 350

Asn Asn Tyr Ala Thr Tyr Tyr Ala Asp Ser Val Lys Asp Arg Phe Thr
                355                 360                 365

Ile Ser Arg Asp Asp Ser Lys Asn Thr Ala Tyr Leu Gln Met Asn Asn
        370                 375                 380

Leu Lys Thr Glu Asp Thr Ala Val Tyr Tyr Cys Val Arg His Gly Asn
385                 390                 395                 400

Phe Gly Asn Ser Tyr Val Ser Trp Phe Ala Tyr Trp Gly Gln Gly Thr
                405                 410                 415

Leu Val Thr Val Ser Ser Gly Gly Gly Ser Gln Val Gln Leu Lys
            420                 425                 430

Gln Ser Gly Pro Gly Leu Val Gln Pro Ser Gln Ser Leu Ser Ile Thr
        435                 440                 445

Cys Thr Val Ser Gly Phe Ser Leu Thr Asn Tyr Gly Val His Trp Val
450                 455                 460

Arg Gln Ser Pro Gly Lys Gly Leu Glu Trp Leu Gly Val Ile Trp Ser
465                 470                 475                 480

Gly Gly Asn Thr Asp Tyr Asn Thr Pro Phe Thr Ser Arg Leu Ser Ile
                485                 490                 495

Asn Lys Asp Asn Ser Lys Ser Gln Val Phe Phe Lys Met Asn Ser Leu
            500                 505                 510

Gln Ser Asn Asp Thr Ala Ile Tyr Tyr Cys Ala Arg Ala Leu Thr Tyr
        515                 520                 525

Tyr Asp Tyr Glu Phe Ala Tyr Trp Gly Gln Gly Thr Leu Val Thr Val
    530                 535                 540

Ser Ala Ala Ser Thr Lys Gly Pro Ser Val Phe Pro Leu Ala Pro Ser
545                 550                 555                 560

Ser Lys Ser Thr Ser Gly Gly Thr Ala Ala Leu Gly Cys Leu Val Lys
                565                 570                 575

Asp Tyr Phe Pro Glu Pro Val Thr Val Ser Trp Asn Ser Gly Ala Leu
            580                 585                 590

Thr Ser Gly Val His Thr Phe Pro Ala Val Leu Gln Ser Ser Gly Leu
        595                 600                 605

Tyr Ser Leu Ser Ser Val Val Thr Val Pro Ser Ser Ser Leu Gly Thr
    610                 615                 620

Gln Thr Tyr Ile Cys Asn Val Asn His Lys Pro Ser Asn Thr Lys Val
625                 630                 635                 640

Asp Lys Lys Val Glu Pro Lys Ser Cys Gly Gly His His His His
                645                 650                 655

His His His Gly Gly Gly Leu Asn Asp Ile Phe Glu Ala Gln Lys Ile
            660                 665                 670

Glu Trp His Glu
        675

<210> SEQ ID NO 14
<211> LENGTH: 255
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 14

Gly Gly Pro Cys Arg Ser His Ile Asp Val Ala Lys Pro Ile Cys Val
1               5                   10                  15

Gly Gly Gly Gly Ser Gly Gly Ser Ile Ser Ser Gly Leu Leu Ser Gly
                20                  25                  30

Arg Ser Asp Ala Gly Gly Gly Ser Asp Ile Leu Leu Thr Gln Ser
            35                  40                  45

Pro Val Ile Leu Ser Val Ser Pro Gly Glu Arg Val Ser Phe Ser Cys
50                  55                  60

Arg Ala Ser Gln Ser Ile Gly Thr Asn Ile His Trp Tyr Gln Gln Arg
65                  70                  75                  80

Thr Asn Gly Ser Pro Arg Leu Leu Ile Lys Tyr Ala Ser Glu Ser Ile
                85                  90                  95

Ser Gly Ile Pro Ser Arg Phe Ser Gly Ser Gly Ser Gly Thr Asp Phe
                100                 105                 110

Thr Leu Ser Ile Asn Ser Val Glu Ser Glu Asp Ile Ala Asp Tyr Tyr
            115                 120                 125

Cys Gln Gln Asn Asn Asn Trp Pro Thr Thr Phe Gly Ala Gly Thr Lys
130                 135                 140

Leu Glu Leu Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
                180                 185                 190

Asn Ala Leu Gln Ser Gly Asn Ser Gln Glu Ser Val Thr Glu Gln Asp
            195                 200                 205

Ser Lys Asp Ser Thr Tyr Ser Leu Ser Ser Thr Leu Thr Leu Ser Lys
210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255

<210> SEQ ID NO 15
<211> LENGTH: 660
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Arg Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80
```

```
Leu Gln Met Asn Ser Leu Arg Pro Glu Asp Thr Ala Val Tyr Tyr Cys
                85                  90                  95
Thr Ile Gly Gly Ser Leu Ser Val Ser Ser Gln Gly Thr Leu Val Thr
            100                 105                 110
Val Ser Ser Gly Gly Gly Gly Ser Gly Gly Gly Ser Gln Gly Gln Ser
        115                 120                 125
Gly Gln Gly Tyr Leu Trp Gly Cys Glu Trp Asn Cys Ala Gly Ile Thr
    130                 135                 140
Thr Gly Ser Ser Gly Gly Ser Gly Gly Ser Gly Gly Ile Ser Ser Gly
145                 150                 155                 160
Leu Leu Ser Gly Arg Ser Asp Ala Gly Gly Gly Ser Gln Thr Val
                165                 170                 175
Val Thr Gln Glu Pro Ser Leu Thr Val Ser Pro Gly Gly Thr Val Thr
            180                 185                 190
Leu Thr Cys Arg Ser Ser Thr Gly Ala Val Thr Thr Ser Asn Tyr Ala
        195                 200                 205
Asn Trp Val Gln Gln Lys Pro Gly Gln Ala Pro Arg Gly Leu Ile Gly
    210                 215                 220
Gly Thr Asn Lys Arg Ala Pro Gly Thr Pro Ala Arg Phe Ser Gly Ser
225                 230                 235                 240
Leu Leu Gly Gly Lys Ala Ala Leu Thr Leu Ser Gly Val Gln Pro Glu
                245                 250                 255
Asp Glu Ala Glu Tyr Tyr Cys Ala Leu Trp Tyr Ser Asn Leu Trp Val
            260                 265                 270
Phe Gly Gly Gly Thr Lys Leu Thr Val Leu Gly Gly Gly Gly Ser Gly
        275                 280                 285
Gly Gly Gly Ser Gly Gly Gly Ser Glu Val Gln Leu Val Glu Ser
    290                 295                 300
Gly Gly Gly Leu Val Gln Pro Gly Gly Ser Leu Lys Leu Ser Cys Ala
305                 310                 315                 320
Ala Ser Gly Phe Thr Phe Asn Thr Tyr Ala Met Asn Trp Val Arg Gln
                325                 330                 335
Ala Pro Gly Lys Gly Leu Glu Trp Val Ala Arg Ile Arg Ser Lys Tyr
            340                 345                 350
Asn Asn Tyr Ala Thr Tyr Tyr Ala Asp Ser Val Lys Asp Arg Phe Thr
        355                 360                 365
Ile Ser Arg Asp Asp Ser Lys Asn Thr Ala Tyr Leu Gln Met Asn Asn
    370                 375                 380
Leu Lys Thr Glu Asp Thr Ala Val Tyr Tyr Cys Val Arg His Gly Asn
385                 390                 395                 400
Phe Gly Asn Ser Tyr Val Ser Trp Phe Ala Tyr Trp Gly Gln Gly Thr
                405                 410                 415
Leu Val Thr Val Ser Ser Gly Gly Gly Ser Gln Val Gln Leu Lys
            420                 425                 430
Gln Ser Gly Pro Gly Leu Val Gln Pro Ser Gln Ser Leu Ser Ile Thr
        435                 440                 445
Cys Thr Val Ser Gly Phe Ser Leu Thr Asn Tyr Gly Val His Trp Val
    450                 455                 460
Arg Gln Ser Pro Gly Lys Gly Leu Glu Trp Leu Gly Val Ile Trp Ser
465                 470                 475                 480
Gly Gly Asn Thr Asp Tyr Asn Thr Pro Phe Thr Ser Arg Leu Ser Ile
                485                 490                 495
```

```
Asn Lys Asp Asn Ser Lys Ser Gln Val Phe Lys Met Asn Ser Leu
            500                 505                 510

Gln Ser Asn Asp Thr Ala Ile Tyr Tyr Cys Ala Arg Ala Leu Thr Tyr
        515                 520                 525

Tyr Asp Tyr Glu Phe Ala Tyr Trp Gly Gln Gly Thr Leu Val Thr Val
    530                 535                 540

Ser Ala Ala Ser Thr Lys Gly Pro Ser Val Phe Pro Leu Ala Pro Ser
545                 550                 555                 560

Ser Lys Ser Thr Ser Gly Gly Thr Ala Ala Leu Gly Cys Leu Val Lys
            565                 570                 575

Asp Tyr Phe Pro Glu Pro Val Thr Val Ser Trp Asn Ser Gly Ala Leu
        580                 585                 590

Thr Ser Gly Val His Thr Phe Pro Ala Val Leu Gln Ser Ser Gly Leu
            595                 600                 605

Tyr Ser Leu Ser Ser Val Val Thr Val Pro Ser Ser Ser Leu Gly Thr
        610                 615                 620

Gln Thr Tyr Ile Cys Asn Val Asn His Lys Pro Ser Asn Thr Lys Val
625                 630                 635                 640

Asp Lys Lys Val Glu Pro Lys Ser Cys Ala Ala Ala His His His His
            645                 650                 655

His His His His
        660

<210> SEQ ID NO 16
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Gly Pro Cys Arg Ser His Ile Asp Val Ala Lys Pro Ile Cys Val
1               5                   10                  15

Gly Gly Gly Gly Ser Ser Gly Gly Ser Ala Ala Gly Leu Leu Ala Pro
            20                  25                  30

Pro Gly Gly Leu Ser Gly Arg Ser Asp Ala Gly Gly Gly Gly Ser Asp
        35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
            85                  90                  95

Tyr Ala Ser Glu Ser Ile Ser Gly Ile Pro Ser Arg Phe Ser Gly Ser
        100                 105                 110

Gly Ser Gly Thr Asp Phe Thr Leu Ser Ile Asn Ser Val Glu Ser Glu
    115                 120                 125

Asp Ile Ala Asp Tyr Tyr Cys Gln Gln Asn Asn Asn Trp Pro Thr Thr
130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
            165                 170                 175

Ala Ser Val Val Cys Leu Leu Asn Asn Phe Tyr Pro Arg Glu Ala Lys
        180                 185                 190
```

```
Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 17
<211> LENGTH: 660
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser Gly Gly Gly Gly Ser Gly Gly Gly Ser Gln Gly Gln Ser
        115                 120                 125

Gly Gln Gly Tyr Leu Trp Gly Cys Glu Trp Asn Cys Ala Gly Ile Thr
    130                 135                 140

Thr Gly Ser Ser Gly Gly Ser Ala Ala Gly Leu Leu Ala Pro Pro Gly
145                 150                 155                 160

Gly Leu Ser Gly Arg Ser Asp Ala Gly Gly Gly Ser Gln Thr Val
                165                 170                 175

Val Thr Gln Glu Pro Ser Leu Thr Val Ser Pro Gly Gly Thr Val Thr
            180                 185                 190

Leu Thr Cys Arg Ser Ser Thr Gly Ala Val Thr Thr Ser Asn Tyr Ala
        195                 200                 205

Asn Trp Val Gln Gln Lys Pro Gly Gln Ala Pro Arg Gly Leu Ile Gly
    210                 215                 220

Gly Thr Asn Lys Arg Ala Pro Gly Thr Pro Ala Arg Phe Ser Gly Ser
225                 230                 235                 240

Leu Leu Gly Gly Lys Ala Ala Leu Thr Leu Ser Gly Val Gln Pro Glu
                245                 250                 255

Asp Glu Ala Glu Tyr Tyr Cys Ala Leu Trp Tyr Ser Asn Leu Trp Val
            260                 265                 270

Phe Gly Gly Gly Thr Lys Leu Thr Val Leu Gly Gly Gly Gly Ser Gly
```

Gly Gly Gly Ser Gly Gly Gly Ser Glu Val Gln Leu Val Glu Ser
275                 280                 285
Gly Gly Gly Leu Val Gln Pro Gly Gly Ser Leu Lys Leu Ser Cys Ala
290                 295                 300
Ala Ser Gly Phe Thr Phe Asn Thr Tyr Ala Met Asn Trp Val Arg Gln
305                 310                 315                 320
        325                 330                 335
Ala Pro Gly Lys Gly Leu Glu Trp Val Ala Arg Ile Arg Ser Lys Tyr
        340                 345                 350
Asn Asn Tyr Ala Thr Tyr Tyr Ala Asp Ser Val Lys Asp Arg Phe Thr
            355                 360                 365
Ile Ser Arg Asp Asp Ser Lys Asn Thr Ala Tyr Leu Gln Met Asn Asn
370                 375                 380
Leu Lys Thr Glu Asp Thr Ala Val Tyr Tyr Cys Val Arg His Gly Asn
385                 390                 395                 400
Phe Gly Asn Ser Tyr Val Ser Trp Phe Ala Tyr Trp Gly Gln Gly Thr
            405                 410                 415
Leu Val Thr Val Ser Ser Gly Gly Gly Gly Ser Gln Val Gln Leu Lys
            420                 425                 430
Gln Ser Gly Pro Gly Leu Val Gln Pro Ser Gln Ser Leu Ser Ile Thr
        435                 440                 445
Cys Thr Val Ser Gly Phe Ser Leu Thr Asn Tyr Gly Val His Trp Val
450                 455                 460
Arg Gln Ser Pro Gly Lys Gly Leu Glu Trp Leu Gly Val Ile Trp Ser
465                 470                 475                 480
Gly Gly Asn Thr Asp Tyr Asn Thr Pro Phe Thr Ser Arg Leu Ser Ile
            485                 490                 495
Asn Lys Asp Asn Ser Lys Ser Gln Val Phe Phe Lys Met Asn Ser Leu
            500                 505                 510
Gln Ser Asn Asp Thr Ala Ile Tyr Tyr Cys Ala Arg Ala Leu Thr Tyr
        515                 520                 525
Tyr Asp Tyr Glu Phe Ala Tyr Trp Gly Gln Gly Thr Leu Val Thr Val
530                 535                 540
Ser Ala Ala Ser Thr Lys Gly Pro Ser Val Phe Pro Leu Ala Pro Ser
545                 550                 555                 560
Ser Lys Ser Thr Ser Gly Gly Thr Ala Ala Leu Gly Cys Leu Val Lys
            565                 570                 575
Asp Tyr Phe Pro Glu Pro Val Thr Val Ser Trp Asn Ser Gly Ala Leu
            580                 585                 590
Thr Ser Gly Val His Thr Phe Pro Ala Val Leu Gln Ser Ser Gly Leu
        595                 600                 605
Tyr Ser Leu Ser Ser Val Val Thr Val Pro Ser Ser Leu Gly Thr
        610                 615                 620
Gln Thr Tyr Ile Cys Asn Val Asn His Lys Pro Ser Asn Thr Lys Val
625                 630                 635                 640
Asp Lys Lys Val Glu Pro Lys Ser Cys Ala Ala Ala His His His His
            645                 650                 655
His His His His
        660

<210> SEQ ID NO 18
<211> LENGTH: 255
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 18

Gly Gly Pro Cys Arg Ser His Ile Asp Val Ala Lys Pro Ile Cys Val
1               5                   10                  15

Gly Gly Gly Gly Ser Gly Gly Gly Ser Pro Leu Gly Leu Ser Gly
            20                  25                  30

Arg Ser Asp Ala Gly Gly Gly Ser Asp Ile Leu Leu Thr Gln Ser
        35                  40                  45

Pro Val Ile Leu Ser Val Ser Pro Gly Glu Arg Val Ser Phe Ser Cys
50                  55                  60

Arg Ala Ser Gln Ser Ile Gly Thr Asn Ile His Trp Tyr Gln Gln Arg
65                  70                  75                  80

Thr Asn Gly Ser Pro Arg Leu Leu Ile Lys Tyr Ala Ser Glu Ser Ile
                85                  90                  95

Ser Gly Ile Pro Ser Arg Phe Ser Gly Ser Gly Ser Gly Thr Asp Phe
            100                 105                 110

Thr Leu Ser Ile Asn Ser Val Glu Ser Glu Asp Ile Ala Asp Tyr Tyr
        115                 120                 125

Cys Gln Gln Asn Asn Asn Trp Pro Thr Thr Phe Gly Ala Gly Thr Lys
130                 135                 140

Leu Glu Leu Lys Arg Thr Val Ala Ala Pro Ser Val Phe Ile Phe Pro
145                 150                 155                 160

Pro Ser Asp Glu Gln Leu Lys Ser Gly Thr Ala Ser Val Val Cys Leu
                165                 170                 175

Leu Asn Asn Phe Tyr Pro Arg Glu Ala Lys Val Gln Trp Lys Val Asp
            180                 185                 190

Asn Ala Leu Gln Ser Gly Asn Ser Gln Glu Ser Val Thr Glu Gln Asp
        195                 200                 205

Ser Lys Asp Ser Thr Tyr Ser Leu Ser Ser Thr Leu Thr Leu Ser Lys
            210                 215                 220

Ala Asp Tyr Glu Lys His Lys Val Tyr Ala Cys Glu Val Thr His Gln
225                 230                 235                 240

Gly Leu Ser Ser Pro Val Thr Lys Ser Phe Asn Arg Gly Glu Cys
                245                 250                 255

<210> SEQ ID NO 19
<211> LENGTH: 660
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80
```

```
Leu Gln Met Asn Ser Leu Arg Pro Glu Asp Thr Ala Val Tyr Tyr Cys
                85                  90                  95
Thr Ile Gly Gly Ser Leu Ser Val Ser Ser Gln Gly Thr Leu Val Thr
            100                 105                 110
Val Ser Ser Gly Gly Gly Gly Ser Gly Gly Gly Ser Gln Gly Gln Ser
        115                 120                 125
Gly Gln Gly Tyr Leu Trp Gly Cys Glu Trp Asn Cys Ala Gly Ile Thr
    130                 135                 140
Thr Gly Ser Ser Gly Gly Ser Gly Gly Gly Ser Gly Gly Ser Pro Leu
145                 150                 155                 160
Gly Leu Ser Gly Arg Ser Asp Ala Gly Gly Gly Ser Gln Thr Val
                165                 170                 175
Val Thr Gln Glu Pro Ser Leu Thr Val Ser Pro Gly Gly Thr Val Thr
            180                 185                 190
Leu Thr Cys Arg Ser Ser Thr Gly Ala Val Thr Thr Ser Asn Tyr Ala
        195                 200                 205
Asn Trp Val Gln Gln Lys Pro Gly Gln Ala Pro Arg Gly Leu Ile Gly
    210                 215                 220
Gly Thr Asn Lys Arg Ala Pro Gly Thr Pro Ala Arg Phe Ser Gly Ser
225                 230                 235                 240
Leu Leu Gly Gly Lys Ala Ala Leu Thr Leu Ser Gly Val Gln Pro Glu
            245                 250                 255
Asp Glu Ala Glu Tyr Tyr Cys Ala Leu Trp Tyr Ser Asn Leu Trp Val
        260                 265                 270
Phe Gly Gly Gly Thr Lys Leu Thr Val Leu Gly Gly Gly Ser Gly
    275                 280                 285
Gly Gly Gly Ser Gly Gly Gly Ser Glu Val Gln Leu Val Glu Ser
        290                 295                 300
Gly Gly Gly Leu Val Gln Pro Gly Gly Ser Leu Lys Leu Ser Cys Ala
305                 310                 315                 320
Ala Ser Gly Phe Thr Phe Asn Thr Tyr Ala Met Asn Trp Val Arg Gln
            325                 330                 335
Ala Pro Gly Lys Gly Leu Glu Trp Val Ala Arg Ile Arg Ser Lys Tyr
        340                 345                 350
Asn Asn Tyr Ala Thr Tyr Tyr Ala Asp Ser Val Lys Asp Arg Phe Thr
    355                 360                 365
Ile Ser Arg Asp Asp Ser Lys Asn Thr Ala Tyr Leu Gln Met Asn Asn
370                 375                 380
Leu Lys Thr Glu Asp Thr Ala Val Tyr Tyr Cys Val Arg His Gly Asn
385                 390                 395                 400
Phe Gly Asn Ser Tyr Val Ser Trp Phe Ala Tyr Trp Gly Gln Gly Thr
            405                 410                 415
Leu Val Thr Val Ser Ser Gly Gly Gly Ser Gln Val Gln Leu Lys
        420                 425                 430
Gln Ser Gly Pro Gly Leu Val Gln Pro Ser Gln Ser Leu Ser Ile Thr
    435                 440                 445
Cys Thr Val Ser Gly Phe Ser Leu Thr Asn Tyr Gly Val His Trp Val
450                 455                 460
Arg Gln Ser Pro Gly Lys Gly Leu Glu Trp Leu Gly Val Ile Trp Ser
465                 470                 475                 480
Gly Gly Asn Thr Asp Tyr Asn Thr Pro Phe Thr Ser Arg Leu Ser Ile
            485                 490                 495
```

```
Asn Lys Asp Asn Ser Lys Ser Gln Val Phe Lys Met Asn Ser Leu
            500                 505                 510

Gln Ser Asn Asp Thr Ala Ile Tyr Tyr Cys Ala Arg Ala Leu Thr Tyr
            515                 520                 525

Tyr Asp Tyr Glu Phe Ala Tyr Trp Gly Gln Gly Thr Leu Val Thr Val
            530                 535                 540

Ser Ala Ala Ser Thr Lys Gly Pro Ser Val Phe Pro Leu Ala Pro Ser
545                 550                 555                 560

Ser Lys Ser Thr Ser Gly Gly Thr Ala Ala Leu Gly Cys Leu Val Lys
                565                 570                 575

Asp Tyr Phe Pro Glu Pro Val Thr Val Ser Trp Asn Ser Gly Ala Leu
            580                 585                 590

Thr Ser Gly Val His Thr Phe Pro Ala Val Leu Gln Ser Ser Gly Leu
            595                 600                 605

Tyr Ser Leu Ser Ser Val Val Thr Val Pro Ser Ser Ser Leu Gly Thr
            610                 615                 620

Gln Thr Tyr Ile Cys Asn Val Asn His Lys Pro Ser Asn Thr Lys Val
625                 630                 635                 640

Asp Lys Lys Val Glu Pro Lys Ser Cys Ala Ala Ala His His His His
                645                 650                 655

His His His His
            660

<210> SEQ ID NO 20
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Gly Pro Cys Arg Ser His Ile Asp Val Ala Lys Pro Ile Cys Val
1               5                   10                  15

Gly Gly Gly Gly Ser Gly Gly Leu Ser Gly Arg Ser Asp Ala Gly Ser
            20                  25                  30

Pro Leu Gly Leu Ala Gly Ser Gly Gly Ser Asp Ile Leu Leu Thr Gln
            35                  40                  45

Ser Pro Val Ile Leu Ser Val Ser Pro Gly Glu Arg Val Ser Phe Ser
    50                  55                  60

Cys Arg Ala Ser Gln Ser Ile Gly Thr Asn Ile His Trp Tyr Gln Gln
65                  70                  75                  80

Arg Thr Asn Gly Ser Pro Arg Leu Leu Ile Lys Tyr Ala Ser Glu Ser
                85                  90                  95

Ile Ser Gly Ile Pro Ser Arg Phe Ser Gly Ser Gly Ser Gly Thr Asp
            100                 105                 110

Phe Thr Leu Ser Ile Asn Ser Val Glu Ser Glu Asp Ile Ala Asp Tyr
            115                 120                 125

Tyr Cys Gln Gln Asn Asn Asn Trp Pro Thr Thr Phe Gly Ala Gly Thr
130                 135                 140

Lys Leu Glu Leu Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190
```

```
Asp Asn Ala Leu Gln Ser Gly Asn Ser Gln Glu Ser Val Thr Glu Gln
            195                 200                 205

Asp Ser Lys Asp Ser Thr Tyr Ser Leu Ser Ser Thr Leu Thr Leu Ser
            210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
            245                 250                 255

<210> SEQ ID NO 21
<211> LENGTH: 660
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser Gly Gly Gly Gly Ser Gly Gly Gly Ser Gln Gly Gln Ser
            115                 120                 125

Gly Gln Gly Tyr Leu Trp Gly Cys Glu Trp Asn Cys Ala Gly Ile Thr
        130                 135                 140

Thr Gly Ser Ser Gly Gly Ser Gly Gly Leu Ser Gly Arg Ser Asp Ala
145                 150                 155                 160

Gly Ser Pro Leu Gly Leu Ala Gly Ser Gly Gly Ser Gln Thr Val
                165                 170                 175

Val Thr Gln Glu Pro Ser Leu Thr Val Ser Pro Gly Gly Thr Val Thr
            180                 185                 190

Leu Thr Cys Arg Ser Ser Thr Gly Ala Val Thr Thr Ser Asn Tyr Ala
            195                 200                 205

Asn Trp Val Gln Gln Lys Pro Gly Gln Ala Pro Arg Gly Leu Ile Gly
        210                 215                 220

Gly Thr Asn Lys Arg Ala Pro Gly Thr Pro Ala Arg Phe Ser Gly Ser
225                 230                 235                 240

Leu Leu Gly Gly Lys Ala Ala Leu Thr Leu Ser Gly Val Gln Pro Glu
                245                 250                 255

Asp Glu Ala Glu Tyr Tyr Cys Ala Leu Trp Tyr Ser Asn Leu Trp Val
            260                 265                 270

Phe Gly Gly Gly Thr Lys Leu Thr Val Leu Gly Gly Gly Gly Ser Gly
        275                 280                 285

Gly Gly Gly Ser Gly Gly Gly Gly Ser Glu Val Gln Leu Val Glu Ser
```

```
            290                 295                 300
Gly Gly Gly Leu Val Gln Pro Gly Gly Ser Leu Lys Leu Ser Cys Ala
305                 310                 315                 320
Ala Ser Gly Phe Thr Phe Asn Thr Tyr Ala Met Asn Trp Val Arg Gln
                325                 330                 335
Ala Pro Gly Lys Gly Leu Glu Trp Val Ala Arg Ile Arg Ser Lys Tyr
            340                 345                 350
Asn Asn Tyr Ala Thr Tyr Tyr Ala Asp Ser Val Lys Asp Arg Phe Thr
        355                 360                 365
Ile Ser Arg Asp Asp Ser Lys Asn Thr Ala Tyr Leu Gln Met Asn Asn
    370                 375                 380
Leu Lys Thr Glu Asp Thr Ala Val Tyr Tyr Cys Val Arg His Gly Asn
385                 390                 395                 400
Phe Gly Asn Ser Tyr Val Ser Trp Phe Ala Tyr Trp Gly Gln Gly Thr
                405                 410                 415
Leu Val Thr Val Ser Ser Gly Gly Gly Ser Gln Val Gln Leu Lys
            420                 425                 430
Gln Ser Gly Pro Gly Leu Val Gln Pro Ser Gln Ser Leu Ser Ile Thr
        435                 440                 445
Cys Thr Val Ser Gly Phe Ser Leu Thr Asn Tyr Gly Val His Trp Val
    450                 455                 460
Arg Gln Ser Pro Gly Lys Gly Leu Glu Trp Leu Gly Val Ile Trp Ser
465                 470                 475                 480
Gly Gly Asn Thr Asp Tyr Asn Thr Pro Phe Thr Ser Arg Leu Ser Ile
                485                 490                 495
Asn Lys Asp Asn Ser Lys Ser Gln Val Phe Phe Lys Met Asn Ser Leu
            500                 505                 510
Gln Ser Asn Asp Thr Ala Ile Tyr Tyr Cys Ala Arg Ala Leu Thr Tyr
        515                 520                 525
Tyr Asp Tyr Glu Phe Ala Tyr Trp Gly Gln Gly Thr Leu Val Thr Val
    530                 535                 540
Ser Ala Ala Ser Thr Lys Gly Pro Ser Val Phe Pro Leu Ala Pro Ser
545                 550                 555                 560
Ser Lys Ser Thr Ser Gly Gly Thr Ala Ala Leu Gly Cys Leu Val Lys
                565                 570                 575
Asp Tyr Phe Pro Glu Pro Val Thr Val Ser Trp Asn Ser Gly Ala Leu
            580                 585                 590
Thr Ser Gly Val His Thr Phe Pro Ala Val Leu Gln Ser Ser Gly Leu
        595                 600                 605
Tyr Ser Leu Ser Ser Val Val Thr Val Pro Ser Ser Ser Leu Gly Thr
    610                 615                 620
Gln Thr Tyr Ile Cys Asn Val Asn His Lys Pro Ser Asn Thr Lys Val
625                 630                 635                 640
Asp Lys Lys Val Glu Pro Lys Ser Cys Ala Ala His His His
                645                 650                 655
His His His His
            660

<210> SEQ ID NO 22
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 22

```
Gln Ile Leu Leu Thr Gln Ser Pro Val Ile Leu Ser Val Ser Pro Gly
1               5                  10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Thr Val Val Thr Gln Glu Pro Ser Leu Thr Val Ser Pro Gly Gly
1               5                  10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Ser Gly Gly Gly Gly Ser Glu Val Gln Leu
        115                 120                 125
```

```
Val Glu Ser Gly Gly Gly Leu Val Gln Pro Gly Gly Ser Leu Lys Leu
    130                 135                 140

Ser Cys Ala Ala Ser Gly Phe Thr Phe Asn Thr Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Asp
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Gly Asn Phe Gly Asn Ser Tyr Val Ser Trp Phe Ala Tyr Trp Gly
225                 230                 235                 240

Gln Gly Thr Leu Val Thr Val Ser Ser Gly Gly Gly Ser Gln Val
                245                 250                 255

Gln Leu Lys Gln Ser Gly Pro Gly Leu Val Gln Pro Ser Gln Ser Leu
            260                 265                 270

Ser Ile Thr Cys Thr Val Ser Gly Phe Ser Leu Thr Asn Tyr Gly Val
        275                 280                 285

His Trp Val Arg Gln Ser Pro Gly Lys Gly Leu Glu Trp Leu Gly Val
    290                 295                 300

Ile Trp Ser Gly Gly Asn Thr Asp Tyr Asn Thr Pro Phe Thr Ser Arg
305                 310                 315                 320

Leu Ser Ile Asn Lys Asp Asn Ser Lys Ser Gln Val Phe Phe Lys Met
                325                 330                 335

Asn Ser Leu Gln Ser Gln Asp Thr Ala Ile Tyr Tyr Cys Ala Arg Ala
            340                 345                 350

Leu Thr Tyr Tyr Asp Tyr Glu Phe Ala Tyr Trp Gly Gln Gly Thr Leu
        355                 360                 365

Val Thr Val Ser Ala Ala Ser Thr Lys Gly Pro Ser Val Phe Pro Leu
    370                 375                 380

Ala Pro Ser Ser Lys Ser Thr Ser Gly Gly Thr Ala Ala Leu Gly Cys
385                 390                 395                 400

Leu Val Lys Asp Tyr Phe Pro Glu Pro Val Thr Val Ser Trp Asn Ser
                405                 410                 415

Gly Ala Leu Thr Ser Gly Val His Thr Phe Pro Ala Val Leu Gln Ser
            420                 425                 430

Ser Gly Leu Tyr Ser Leu Ser Ser Val Val Thr Val Pro Ser Ser Ser
        435                 440                 445

Leu Gly Thr Gln Thr Tyr Ile Cys Asn Val Asn His Lys Pro Ser Asn
    450                 455                 460

Thr Lys Val Asp Lys Lys Val Glu Pro Lys Ser Cys Gly Gly His His
465                 470                 475                 480

His His His His His Gly Gly Gly Leu Asn Asp Ile Phe Glu Ala
                485                 490                 495

Gln Lys Ile Glu Trp His Glu
            500
```

<210> SEQ ID NO 24
<211> LENGTH: 214
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 24

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

```
Gly Ser Gly Gly Gly Ser Gly Gly Gly Ser Glu Val Gln Leu
            115                 120                 125
Val Glu Ser Gly Gly Leu Val Gln Pro Gly Ser Leu Lys Leu
    130                 135                 140
Ser Cys Ala Ala Ser Gly Phe Thr Phe Asn Thr Tyr Ala Met Asn Trp
145                 150                 155                 160
Val Arg Gln Ala Pro Gly Lys Gly Leu Glu Trp Val Ala Arg Ile Arg
                165                 170                 175
Ser Lys Tyr Asn Asn Tyr Ala Thr Tyr Tyr Ala Asp Ser Val Lys Asp
                180                 185                 190
Arg Phe Thr Ile Ser Arg Asp Asp Ser Lys Asn Thr Ala Tyr Leu Gln
                195                 200                 205
Met Asn Asn Leu Lys Thr Glu Asp Thr Ala Val Tyr Tyr Cys Val Arg
210                 215                 220
His Gly Asn Phe Gly Asn Ser Tyr Val Ser Trp Phe Ala Tyr Trp Gly
225                 230                 235                 240
Gln Gly Thr Leu Val Thr Val Ser Ser Gly Gly Gly Ser Gln Val
                245                 250                 255
Gln Leu Lys Gln Ser Gly Pro Gly Leu Val Gln Pro Ser Gln Ser Leu
        260                 265                 270
Ser Ile Thr Cys Thr Val Ser Gly Phe Ser Leu Thr Asn Tyr Gly Val
    275                 280                 285
His Trp Val Arg Gln Ser Pro Gly Lys Gly Leu Glu Trp Leu Gly Val
    290                 295                 300
Ile Trp Ser Gly Gly Asn Thr Asp Tyr Asn Thr Pro Phe Thr Ser Arg
305                 310                 315                 320
Leu Ser Ile Asn Lys Asp Asn Ser Lys Ser Gln Val Phe Phe Lys Met
                325                 330                 335
Asn Ser Leu Gln Ser Asn Asp Thr Ala Ile Tyr Tyr Cys Ala Arg Ala
                340                 345                 350
Leu Thr Tyr Tyr Asp Tyr Glu Phe Ala Tyr Trp Gly Gln Gly Thr Leu
                355                 360                 365
Val Thr Val Ser Ala Ala Ser Thr Lys Gly Pro Ser Val Phe Pro Leu
    370                 375                 380
Ala Pro Ser Ser Lys Ser Thr Ser Gly Gly Thr Ala Ala Leu Gly Cys
385                 390                 395                 400
Leu Val Lys Asp Tyr Phe Pro Glu Pro Val Thr Val Ser Trp Asn Ser
                405                 410                 415
Gly Ala Leu Thr Ser Gly Val His Thr Phe Pro Ala Val Leu Gln Ser
                420                 425                 430
Ser Gly Leu Tyr Ser Leu Ser Ser Val Val Thr Val Pro Ser Ser Ser
        435                 440                 445
Leu Gly Thr Gln Thr Tyr Ile Cys Asn Val Asn His Lys Pro Ser Asn
    450                 455                 460
Thr Lys Val Asp Lys Lys Val Glu Pro Lys Ser Cys Gly Gly His His
465                 470                 475                 480
His His His His His His Gly Gly Gly Leu Asn Asp Ile Phe Glu Ala
                485                 490                 495
Gln Lys Ile Glu Trp His Glu
            500
```

<210> SEQ ID NO 26
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 26

Ala Gly Leu Leu Ala Pro Pro Gly Gly Leu Ser Gly Arg Ser Asp Ala
1               5                   10                  15

Gly

<210> SEQ ID NO 27
<211> LENGTH: 5
<212> TYPE: PRT
<213> ORGANISM: Unknown
<220> FEATURE:
<223> OTHER INFORMATION: Description of Unknown:
      Type I cytokine receptor sequence
<220> FEATURE:
<221> NAME/KEY: MOD_RES
<222> LOCATION: (3)..(3)
<223> OTHER INFORMATION: Any amino acid

<400> SEQUENCE: 27

Trp Ser Xaa Trp Ser
1               5
```

US 11,512,113 B2

CLEAVABLE LINKER COMPOSITIONS AND METHODS

CROSS-REFERENCE

This application claims the benefit of U.S. Provisional Application No. 63/064,268, filed Aug. 11, 2020, which application is incorporated herein by reference.

SEQUENCE LISTING

The instant application contains a Sequence Listing which has been submitted electronically in ASCII format and is hereby incorporated by reference in its entirety. Said ASCII copy, created on Aug. 5, 2021, is named 52426_720_201_SL.txt and is 58,324 bytes in size.

SUMMARY

Disclosed herein, in certain embodiments, are isolated polypeptides comprising a cleavable linker according to the amino acid sequence of SEQ ID NO: 1 (LSGRSDAG). In some embodiments, the cleavable linker comprises the amino acid sequence of SEQ ID NO: 3 (ISSGLLSGRSDAG). In some embodiments, the cleavable linker comprises the amino acid sequence of SEQ ID NO: 26 (AGLLAPPGGLSGRSDAG). In some embodiments, the cleavable linker comprises the amino acid sequence of SEQ ID NO: 4 (AAGLLAPPGGLSGRSDAG). In some embodiments, the cleavable linker comprises the amino acid sequence of SEQ ID NO: 5 (SPLGLSGRSDAG). In some embodiments, the cleavable linker comprises the amino acid sequence of SEQ ID NO: 6 (LSGRSDAGSPLGLAG). In some embodiments, the cleavable linker is cleavable by a protease. In some embodiments, the protease comprises a tumor specific protease. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the serine protease comprises matriptase, urokinase, or hepsin. In some embodiments, the isolated polypeptide further comprises an antigen binding domain that binds to a target antigen. In some embodiments, the antigen binding domain is C-terminal to the cleavable linker. In some embodiments, the isolated polypeptide further comprises a cytokine or cytokine fragment that binds to a cytokine receptor. In some embodiments, the cytokine or cytokine fragment is C-terminal to the cleavable linker. In some embodiments, the cleavable linker connects a peptide to an antigen binding domain that binds to a target antigen or to a cytokine or cytokine fragment that binds to a cytokine receptor in a configuration according to Formula I: $A_1$-$L_1$-$P_1$ wherein $A_1$ comprises the antigen binding domain that binds to the target antigen or the cytokine or cytokine fragment that binds to the cytokine receptor; $L_1$ comprises the cleavable linker; $P_1$ comprises a peptide that impairs binding of the antigen binding domain to the target antigen or impairs binding of the cytokine to the cytokine receptor. In some embodiments, $P_1$ is connected N-terminal to the cleavable linker and $A_1$ is connected C-terminal to the cleavable linker. In some embodiments, $P_1$ is connected C-terminal to the cleavable linker and $A_1$ is connected N-terminal to the cleavable linker. In some embodiments, $P_1$ is bound to $A_1$ through ionic interactions, electrostatic interactions, hydrophobic interactions, $P_1$-stacking interactions, and H-bonding interactions, or a combination thereof. In some embodiments, $P_1$ has less than 70% sequence homology to the target antigen or the cytokine receptor. In some embodiments, P1 comprises a peptide sequence of at least 10 amino acids in length. In some embodiments, $P_1$ comprises a peptide sequence of at least 10 amino acids in length and no more than 20 amino acids in length. In some embodiments, $P_1$ comprises a peptide sequence of at least 16 amino acids in length. In some embodiments, $P_1$ comprises a peptide sequence of no more than 40 amino acids in length. In some embodiments, $P_1$ comprises a cyclic peptide or a linear peptide. In some embodiments, $P_1$ comprises a cyclic peptide. In some embodiments, $P_1$ is further linked to a half-life extending moiety. In some embodiments, the half-life extending moiety is a single-domain antibody. In some embodiments, the single domain antibody comprises 10G. In some embodiments, $A_1$ comprises an antibody, a single chain variable fragment (scFv), a heavy chain variable domain (VH domain), a light chain variable domain (VL domain), a variable domain (VHH) of a camelid derived single domain antibody, a Fab, a Fab', a Fab light chain polypeptide, or a Fab heavy chain polypeptide. In some embodiments, the target antigen comprises a tumor antigen. In some embodiments, $A_1$ comprises the Fab light chain polypeptide or the Fab heavy chain polypeptide. In some embodiments, $A_1$ comprises an epidermal growth factor receptor (EGFR) binding domain. In some embodiments, the target antigen comprises an effector cell antigen. In some embodiments, $A_1$ comprises the scFv. In some embodiments, the scFv comprises an anti-CD3e single chain variable fragment. In some embodiments, $A_1$ comprises the cytokine. In some embodiments, the cytokine or cytokine fragment is a wild-type cytokine. In some embodiments, the cytokine or cytokine fragment is a mutein of the cytokine. In some embodiments, the cytokine receptor is an interferon receptor or an interleukin receptor. In some embodiments, the cytokine receptor comprises an interferon receptor, GM-CSF receptor, IL-2 receptor, IL-4 receptor, IL-6 receptor, IL-7 receptor, IL-10 receptor, IL-12 receptor, IL-15 receptor, IL-21 receptor, or TGF-β receptor. In some embodiments, the cytokine or cytokine fragment comprises an interferon, GM-CSF, IL-2, IL-7, IL-12, IL-15, or IL-21. In some embodiments, the cytokine or cytokine fragment comprises an IL-2, IL-12, IL-6, IL-4, IL-10, or TGFβ. In some embodiments, the isolated polypeptide is complexed with a second isolated polypeptide comprising a second antigen binding domain or a second cytokine or second cytokine fragment. In some embodiments, the second isolated polypeptide is in a configuration according to Formula II: $A_2$-$L_2$-$P_2$ wherein $A_2$ comprises the second antigen binding domain or the second cytokine; $L_2$ comprises a second cleavable linker; $P_2$ comprises a second peptide that impairs binding of the second antigen binding domain to a second target antigen or impairs binding of the second cytokine or second cytokine fragment to a second cytokine receptor. In some embodiments, the second cleavable linker comprises the amino acid sequence of SEQ ID NO: 1 (LSGRSDAG). In some embodiments, the second cleavable linker comprises the amino acid sequence of SEQ ID NO: 3 (ISSGLLSGRSDAG). In some embodiments, the second cleavable linker comprises the amino acid sequence of SEQ ID NO: 26 (AGLLAPPGGLSGRSDAG). In some embodiments, the second cleavable linker comprises the amino acid sequence of SEQ ID NO: 4 (AAGLLAPPGGLSGRSDAG). In some embodiments, the second cleavable linker comprises the amino acid sequence of SEQ ID NO: 5 (SPLGLSGRSDAG). In some embodiments, the second cleavable linker comprises the amino acid sequence of SEQ ID NO: 6 (LSGRSDAGSPLGLAG). In some embodiments, $P_2$ is connected N-terminal to the second cleavable linker and $A_2$ is connected C-terminal to the second cleavable linker. In some embodiments, $P_2$ is connected C-terminal to the second cleavable linker and $A_2$ is connected N-terminal to the second cleavable linker. In some embodiments, $P_2$ is bound to $A_2$ through ionic interactions, electrostatic interactions, hydrophobic interactions, $P_1$-stacking interactions, and H-bonding interactions, or a combination thereof. In some embodiments, $P_2$ has less than 70% sequence homology to the second target antigen or the second cytokine receptor. In some embodiments, $P_2$ comprises a peptide sequence of at least 10 amino acids in length. In some embodiments, $P_2$ comprises a peptide sequence of at least 10 amino acids in length and no more than 20 amino acids in length. In some embodiments, $P_2$ comprises a peptide sequence of at least 16 amino acids in length. In some embodiments, $P_2$ comprises a peptide sequence of no more than 40 amino acids in length. In some embodiments, $P_2$ comprises a cyclic peptide or a linear peptide. In some embodiments, $P_2$ comprises a cyclic peptide. In some embodiments, $A_2$ comprises an antibody, a single chain variable fragment (scFv), a heavy chain variable domain (VH domain), a light chain variable domain (VL domain), a variable domain (VHH) of a camelid derived single domain antibody, a Fab, a Fab', a Fab light chain polypeptide, or a Fab heavy chain polypeptide. In some embodiments, the second target antigen comprises a tumor antigen. In some embodiments, $A_2$ comprises the Fab light chain polypeptide or the Fab heavy chain polypeptide. In some embodiments, $A_2$ comprises an epidermal growth factor receptor (EGFR) binding domain. In some embodiments, the second target antigen comprises an effector cell antigen. In some embodiments, $A_2$ comprises the scFv. In some embodiments, the scFv comprises an anti-CD3e single chain variable fragment. In some embodiments, $A_2$ comprises the second cytokine. In some embodiments, the second cytokine or second cytokine fragment is a wild-type cytokine. In some embodiments, the second cytokine or second cytokine fragment is a mutein of the cytokine. In some embodiments, the second cytokine receptor is an interferon receptor or an interleukin receptor. In some embodiments, the second cytokine receptor comprises an interferon receptor, GM-CSF receptor, IL-2 receptor, IL-4 receptor, IL-6 receptor, IL-7 receptor, IL-10 receptor, IL-12 receptor, IL-15 receptor, IL-21 receptor, or TGF-β receptor. In some embodiments, the second cytokine or second cytokine fragment comprises an interferon, GM-CSF, IL-2, IL-7, IL-12, IL-15, or IL-21. In some embodiments, the second cytokine or second cytokine fragment comprises an IL-2, IL-12, IL-6, IL-4, IL-10, or TGFβ.

Disclosed herein are pharmaceutical compositions comprising: the isolated polypeptide comprising a cleavable linker according to any of the above embodiments; and a pharmaceutically acceptable excipient.

Disclosed herein are isolated recombinant nucleic acid molecule encoding the isolated polypeptide comprising a cleavable linker according to any of the above embodiments.

Disclosed herein are vectors comprising the recombinant nucleic acid molecule according to the above embodiment.

Disclosed herein are methods of producing an isolated polypeptide comprising a cleavable linker comprising culturing a cell under conditions that lead to expression of the polypeptide, wherein the cell comprises the vector of the above embodiment.

Disclosed herein are methods of manufacturing an isolated polypeptide comprising a cleavable linker, the method comprising: (a) culturing a cell comprising the recombinant nucleic acid molecule of the above embodiments under conditions that lead to expression of the polypeptide, and (b) isolating the polypeptide.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1A:
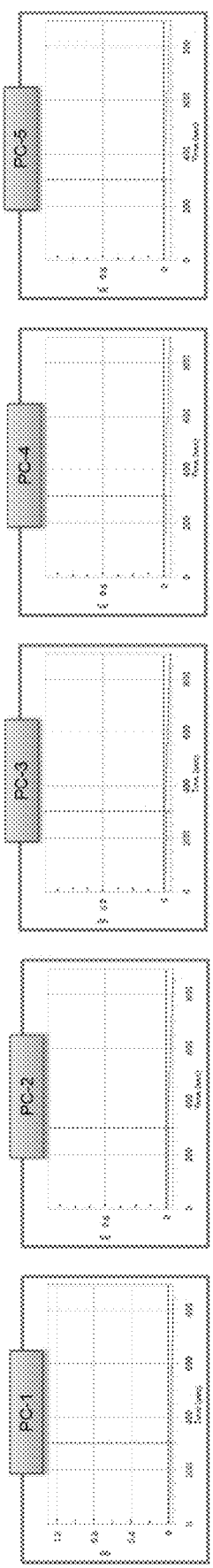
FIGS. 1A-1B illustrate binding of polypeptide complexes PC-1, PC-2, PC-3, PC-4, and PC-5 comprising EGFR masking (FIG. 1A) and followed by cleavage by the tumor protease MTSP1 (FIG. 1B).

Protein-based therapies such as antibodies, T cell receptors (TCR), and cytokine therapies have proven effective for a variety diseases and disorders. As with any therapy, there is a need to minimize off-target effects of the protein-based therapy in healthy tissue while maintaining activity of the protein-based therapy in disease tissue. One such strategy is to create an inactive form of the protein-based therapy in which a necessary binding site on the protein-based therapy is blocked with a peptide linked to the protein-based therapy, thereby preventing the protein-based therapy from binding or interacting with its cognate receptor or target antigen when in healthy tissue. For activating the protein-based therapy in the desired disease-state microenvironment, the peptide is linked to the protein-based therapy with a linker that is cleavable by a protease that is specific to the disease-state microenvironment. The peptide is then released from the protein-based therapy when in the disease-state microenvironment.

Accordingly, disclosed herein, are cleavable linkers which can be applied to a variety of protein-based therapy formats, for use in reducing off-target effects of the protein-based therapy in healthy tissue, while maintaining activity of the protein-based therapy in disease tissue. The cleavable linkers, as disclosed herein, have desirable properties, which include, for example but are not limited to, increased rates of proteolysis by tumor proteases or cleavable by an expanded panel of tumor proteases while also having comparable safety profiles relative to control linkers.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

"Fragment" as used herein refers to a peptide or a polypeptide that comprises less than the full length amino acid sequence.

"Peptide", "$P_1$", or "$P_2$" as used herein refers to an amino acid sequence of less than 50 amino acids and specifically excludes a cytokine ligand binding domain, fragments, or muteins thereof, a cytokine receptor, fragments, or muteins thereof, and any antibody or antibody binding fragments (for example, a single domain antibody, Fab, or scFv) that binds to a cytokine, or binds to a cognate cytokine receptor.

As disclosed herein, in some embodiments, are isolated polypeptides comprising a cleavable linker according to the amino acid sequence of SEQ ID NO: 1 (LSGRSDAG)

In some embodiments, the cleavable linker comprises the amino acid sequence of SEQ ID NO: 3 (ISSGLLSGRSDAG). In some embodiments, the cleavable linker comprises the amino acid sequence of SEQ ID NO: 26 (AGLLAPPGGLSGRSDAG). In some embodiments, the cleavable linker comprises the amino acid sequence of SEQ ID NO: 4 (AAGLLAPPGGLSGRSDAG). In some embodiments, the cleavable linker comprises the amino acid sequence of SEQ ID NO: 5 (SPLGLSGRSDAG). In some embodiments, the cleavable linker comprises the amino acid sequence of SEQ ID NO: 6 (LSGRSDAGSPLGLAG).

In some embodiments, the cleavable linker consists of the amino acid sequence of SEQ ID NO: 1 (LSGRSDAG). In some embodiments, the cleavable linker consists of the amino acid sequence of SEQ ID NO: 3 (ISSGLLSGRSDAG). In some embodiments, the cleavable linker consists of the amino acid sequence of SEQ ID NO: 26 (AGLLAPPGGLSGRSDAG). In some embodiments, the cleavable linker consists of the amino acid sequence of SEQ ID NO: 4 (AAGLLAPPGGLSGRSDAG). In some embodiments, the cleavable linker consists of the amino acid sequence of SEQ ID NO: 5 (SPLGLSGRSDAG). In some embodiments, the cleavable linker consists of the amino acid sequence of SEQ ID NO: 6 (LSGRSDAGSPLGLAG).

In some embodiments, the cleavable linker comprises the amino acid sequence selected from the group consisting of SEQ ID NO: 3, 4, 5, and 6.

In some embodiments, are isolated polypeptides comprising a cleavable linker according to the amino acid sequence of Linker 1 (ISSGLLSGRSDAG) SEQ ID NO: 3, Linker 2 (AAGLLAPPGGLSGRSDAG) SEQ ID NO:4, Linker 3 (SPLGLSGRSDAG) SEQ ID NO: 5, or Linker 4 (LSGRSDAGSPLGLAG) SEQ ID NO: 6 or an isolated polypeptide comprising a cleavable linker that has 1, 2, or 3 amino acid substitutions, additions, or deletions relative to the amino acid sequence of Linker 1, Linker 2, Linker 3, or Linker 4.

In some embodiments, the cleavable linker comprises the amino acid sequence of Linker 1. In some embodiments, the cleavable linker consists of the amino acid sequence of Linker 1. In some embodiments, the cleavable linker has 1 amino acid substitution, addition, or deletion relative to the amino acid sequence of Linker 1. In some embodiments, the cleavable linker has 2 amino acid substitutions, additions, or deletions relative to the amino acid sequence of Linker 1. In some embodiments, the cleavable linker has 3 amino acid substitutions, additions, or deletions relative to the amino acid sequence of Linker 1.

In some embodiments, the cleavable linker comprises the amino acid sequence of Linker 2. In some embodiments, the cleavable linker consists of the amino acid sequence of Linker 2. In some embodiments, the cleavable linker has 1 amino acid substitution, addition, or deletion relative to the amino acid sequence of Linker 2. In some embodiments, the cleavable linker has 2 amino acid substitutions, additions, or deletions relative to the amino acid sequence of Linker 2. In some embodiments, the cleavable linker has 3 amino acid substitutions, additions, or deletions relative to the amino acid sequence of Linker 2.

In some embodiments, the cleavable linker comprises the amino acid sequence of Linker 3. In some embodiments, the cleavable linker consists of the amino acid sequence of Linker 3. In some embodiments, the cleavable linker has 1 amino acid substitution, addition, or deletion relative to the amino acid sequence of Linker 3. In some embodiments, the cleavable linker has 2 amino acid substitutions, additions, or deletions relative to the amino acid sequence of Linker 3. In some embodiments, the cleavable linker has 3 amino acid substitutions, additions, or deletions relative to the amino acid sequence of Linker 3.

In some embodiments, the cleavable linker comprises the amino acid sequence of Linker 4. In some embodiments, the cleavable linker consists of the amino acid sequence of Linker 4. In some embodiments, the cleavable linker has 1 amino acid substitution, addition, or deletion relative to the amino acid sequence of Linker 4. In some embodiments, the cleavable linker has 2 amino acid substitutions, additions, or deletions relative to the amino acid sequence of Linker 4. In some embodiments, the cleavable linker has 3 amino acid substitutions, additions, or deletions relative to the amino acid sequence of Linker 4.

In some embodiments, the amino acid substitution, addition, or deletion results in an amino acid sequence that is at least 75% identical, e.g., 77%, 80%, 82%, 85%, 88%, 90%, 91%, 92%, 93%, 94%, 95%, 96%, 97%, 98%, 99%, or 100% identical to the amino acid sequence of any protein described herein. In some embodiments, the amino acid substitution is a conservative amino acid substitution. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

In some embodiments, the cleavable linker comprises a modified amino acid or non-natural amino acid, or a modified non-natural amino acid, or a combination thereof. In some embodiments, the modified amino acid or a modified non-natural amino acid comprises a post-translational modification. In some embodiments, the cleavable linker comprises a modification including, but not limited, to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to the cleavable linker including the peptide backbone, or the amino acid side chains.

In some embodiments, the cleavable linker is cleavable by a protease. In some embodiments, the protease is present in higher levels in a disease-state microenvironment relative to levels in healthy tissue or a microenvironment that is not the disease-state microenvironment. In some embodiments, the protease comprises a tumor specific protease. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the matrix metalloprotease is selected from the group consisting of MMP2, MMP7, MMP9, MMP13, and MMP14. In some embodiments, the matrix metalloprotease comprises MMP2. In some embodiments, the matrix metalloprotease comprises MMP7. In some embodiments, the matrix metalloprotease comprises MMP9. In some embodiments, the matrix metalloprotease comprises MMP13. In some embodiments, the matrix metalloprotease comprises MMP14. In some embodiments, the serine protease comprises matriptase, urokinase, or hepsin. In some embodiments, the serine protease is selected from the group consisting of matriptase, urokinase, and hepsin. In some embodiments, the serine protease comprises matriptase. In some embodiments, the serine protease comprises urokinase. In some embodiments, the serine protease comprises hepsin. In some embodiments, the cleavable linker is cleaved by a variety of proteases. In some embodiments, the cleavable linker is cleaved by at least 1, 2, 3, 4, 5, 6, 7, 8, 9, 10, 15, 20, or more than 20 different proteases.

In some embodiments, the cleavable linker has increased rates of proteolysis as compared to the rates of proteolysis for linkers without the cleavable linker sequences. In some embodiments, the cleavable linker has increased rates of proteolysis that is at least 5× higher than the rates of proteolysis for linkers without the cleavable linker sequences. In some embodiments, the cleavable linker has increased rates of proteolysis that is at least 8× higher than the rates of proteolysis for linkers without the cleavable linker sequences. In some embodiments, the cleavable linker has increased rates of proteolysis that is at least 10× higher than the rates of proteolysis for linkers without the cleavable linker sequences. In some embodiments, the cleavable linker has increased rates of proteolysis that is at least 15× higher than the rates of proteolysis for linkers without the cleavable linker sequences. In some embodiments, the cleavable linker has increased rates of proteolysis that is at least 20× higher than the rates of proteolysis for linkers without the cleavable linker sequences. In some embodiments, the cleavable linker has increased rates of proteolysis that is at least 25× higher than the rates of proteolysis for linkers without the cleavable linker sequences. In some embodiments, the cleavable linker has increased rates of proteolysis that is at least 30× higher than the rates of proteolysis for linkers without the cleavable linker sequences. In some embodiments, the cleavable linker has increased rates of proteolysis that is at least 40× higher than the rates of proteolysis for linkers without the cleavable linker sequences. In some embodiments, the cleavable linker has increased rates of proteolysis that is at least 50× higher than the rates of proteolysis for linkers without the cleavable linker sequences. In some embodiments, the cleavable linker has increased rates of proteolysis that is at least 60× higher than the rates of proteolysis for linkers without the cleavable linker sequences. In some embodiments, the cleavable linker has increased rates of proteolysis that is at least 70× higher than the rates of proteolysis for linkers without the cleavable linker sequences. In some embodiments, the cleavable linker has increased rates of proteolysis that is at least 75× higher than the rates of proteolysis for linkers without the cleavable linker sequences. In some embodiments, the cleavable linker has increased rates of proteolysis that is at least 80× higher than the rates of proteolysis for linkers without the cleavable linker sequences. In some embodiments, the cleavable linker has increased rates of proteolysis that is at least 90× higher than the rates of proteolysis for linkers without the cleavable linker sequences. In some embodiments, the cleavable linker has increased rates of proteolysis that is at least 100× higher than the rates of proteolysis for linkers without the cleavable linker sequences. In some embodiments, the cleavable linker has increased rates of proteolysis that is at least 120× higher than the rates of proteolysis for linkers without the cleavable linker sequences. In some embodiments, the cleavable linker is cleaved by a protease. In some embodiments, the protease comprises a tumor specific protease. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the serine protease comprises matriptase, urokinase, or hepsin.

In some embodiments, the cleavable linker has improved stability in human serum as compared to the stability in human serum without the cleavable linker sequences. In some embodiments, the cleavable linker has improved stability in human serum that is at least 5× higher than the stability in human serum for linkers without the cleavable linker sequences. In some embodiments, the cleavable linker has improved stability in human serum that is at least 8× higher than the stability in human serum for linkers without the cleavable linker sequences. In some embodiments, the cleavable linker has improved stability in human serum that is at least 10× higher than the stability in human serum for linkers without the cleavable linker sequences. In some embodiments, the cleavable linker has improved stability in human serum that is at least 15× higher than the stability in human serum for linkers without the cleavable linker sequences. In some embodiments, the cleavable linker has improved stability in human serum that is at least 20× higher than the stability in human serum for linkers without the cleavable linker sequences. In some embodiments, the cleavable linker has improved stability in human serum that is at least 25× higher than the stability in human serum for linkers without the cleavable linker sequences. In some embodiments, the cleavable linker has improved stability in human serum that is at least 30× higher than the stability in human serum for linkers without the cleavable linker sequences. In some embodiments, the cleavable linker has improved stability in human serum that is at least 40× higher than the stability in human serum for linkers without the cleavable linker sequences. In some embodiments, the cleavable linker has improved stability in human serum that is at least 50× higher than the stability in human serum for linkers without the cleavable linker sequences. In some embodiments, the cleavable linker has improved stability in human serum that is at least 60× higher than the stability in human serum for linkers without the cleavable linker sequences. In some embodiments, the cleavable linker has improved stability in human serum that is at least 70× higher than the stability in human serum for linkers without the cleavable linker sequences. In some embodiments, the cleavable linker has improved stability in human serum that is at least 75× higher than the stability in human serum for linkers without the cleavable linker sequences. In some embodiments, the cleavable linker has improved stability in human serum that is at least 80× higher than the stability in human serum for linkers without the cleavable linker sequences. In some embodiments, the cleavable linker has improved stability in human serum that is at least 90× higher than the stability in human serum for linkers without the cleavable linker sequences. In some embodiments, the cleavable linker has improved stability in human serum that is at least 100× higher than the stability in human serum for linkers without the cleavable linker sequences. In some embodiments, the cleavable linker has improved stability in human serum that is at least 120× higher than the stability in human serum for linkers without the cleavable linker sequences.

In some embodiments, the isolated polypeptide comprising the cleavable linker has increased rates of proteolysis as compared to an isolated polypeptide of the same amino acid sequence but comprising a cleavable linker according to the amino acid sequence of SEQ ID NO: 2.

In some embodiments, the isolated polypeptide comprising the cleavable linker has improved or equivalent serum stability as compared to an isolated polypeptide of the same amino acid sequence but comprising a cleavable linker according to the amino acid sequence of SEQ ID NO: 2.

In some embodiments, the isolated polypeptide comprising the cleavable linker has improved or equivalent in vitro tumor cell killing as compared to an isolated polypeptide of the same amino acid sequence but comprising a cleavable linker according to the amino acid sequence of SEQ ID NO: 2.

In some embodiments, the isolated polypeptide comprising the cleavable linker has improved or equivalent pharmacokinetic parameters in cynomolgus monkeys as compared to an isolated polypeptide of the same amino acid sequence but comprising a cleavable linker according to the amino acid sequence of SEQ ID NO: 2.

In some embodiments, the isolated polypeptide comprising the cleavable linker has improved or equivalent liver toxicity levels in cynomolgus monkeys as compared to an isolated polypeptide of the same amino acid sequence but comprising a cleavable linker according to the amino acid sequence of SEQ ID NO: 2.

In some embodiments, the isolated polypeptide further comprises an antigen binding domain that binds to a target antigen. In some embodiments, the antigen binding domain is C-terminal to the cleavable linker. In some embodiments, the isolated polypeptide further comprises a cytokine or cytokine fragment that binds to a cytokine receptor. In some embodiments, the cytokine or cytokine fragment is C-terminal to the cleavable linker.

In some embodiments, the cleavable linker connects a peptide to an antigen binding domain that binds to a target antigen or to a cytokine that binds to a cytokine receptor in a configuration according to Formula I:

$$A_1\text{-}L_1\text{-}P_1 \quad \text{(Formula I)}$$

wherein $A_1$ comprises the antigen binding domain that binds to the target antigen or the cytokine that binds to the cytokine receptor; $L_1$ comprises the cleavable linker; $P_1$ comprises a peptide that impairs binding of the antigen binding domain to the target antigen or impairs binding of the cytokine to the cytokine receptor. In some embodiments, $P_1$ is connected N-terminal to the cleavable linker and $A_1$ is connected C-terminal to the cleavable linker. In some embodiments, $P_1$ is connected C-terminal to the cleavable linker and $A_1$ is connected N-terminal to the cleavable linker.

In some embodiments, the isolated polypeptide is complexed with a second isolated polypeptide comprising a second antigen binding domain or a second cytokine. In some embodiments, the second isolated polypeptide is in a configuration according to Formula II:

$$A_2\text{-}L_2\text{-}P_2 \quad \text{(Formula II)}$$

wherein $A_2$ comprises the second antigen binding domain or the second cytokine; $L_2$ comprises a second cleavable linker; and $P_2$ comprises a second peptide that impairs binding of the second antigen binding domain to a second target antigen or impairs binding of the second cytokine to a second cytokine receptor.

In some embodiments, $P_2$ is connected N-terminal to the second cleavable linker and $A_2$ is connected C-terminal to the second cleavable linker. In some embodiments, $P_2$ is connected C-terminal to the second cleavable linker and $A_2$ is connected N-terminal to the second cleavable linker.

In some embodiments, the second cleavable linker comprises the amino acid sequence of SEQ ID NO: 1 (LSGRSDAG). In some embodiments, the second cleavable linker comprises the amino acid sequence of SEQ ID NO: 3 (ISSGLLSGRSDAG). In some embodiments, the second cleavable linker comprises the amino acid sequence of SEQ ID NO: 26 (AGLLAPPGGLSGRSDAG). In some embodiments, the second cleavable linker comprises the amino acid sequence of SEQ ID NO: 4 (AAGLLAPPGGLSGRSDAG). In some embodiments, the second cleavable linker comprises the amino acid sequence of SEQ ID NO: 5 (SPLGLSGRSDAG). In some embodiments, the second cleavable linker comprises the amino acid sequence of SEQ ID NO: 6 (LSGRSDAGSPLGLAG).

In some embodiments, $L_1$ or $L_2$ is at least 8 amino acids in length. In some embodiments, $L_1$ or $L_2$ is at least 10 amino acids in length but no more than 50 amino acids in length. In some embodiments, $L_1$ or $L_2$ is at least 10 amino acids in length but no more than 30 amino acids in length. In some embodiments, $L_1$ or $L_2$ is at least 18 amino acids in length. In some embodiments, $L_1$ or $L_2$ is at least 26 amino acids in length. In some embodiments, $L_1$ or $L_2$ is at least 30 amino acids in length. In some embodiments, $L_1$ or $L_2$ is at least 40 amino acids in length. In some embodiments, $L_1$ or $L_2$ is at least 50 amino acids in length.

Peptide ($P_1$ or $P_2$)

In some embodiments, $P_1$ comprises a peptide that impairs binding of the antigen binding domain to the target antigen. In some embodiments, $P_1$ comprises a peptide that impairs binding of the cytokine to the cytokine receptor. In some embodiments, $P_1$ is bound to $A_1$ through ionic interactions, electrostatic interactions, hydrophobic interactions, $P_1$-stacking interactions, and H-bonding interactions, or a combination thereof. In some embodiments, $P_1$ is bound to $A_1$ at or near a cytokine receptor binding site. In some embodiments, $P_1$ is bound to $A_1$ at or near an antigen binding site. In some embodiments, $P_1$ becomes unbound from $A_1$ when $L_1$ is cleaved by the protease thereby exposing $P_1$ to the target antigen or cytokine receptor. In some embodiments, the protease comprises a tumor specific protease. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the serine protease comprises matriptase, urokinase, or hepsin. In some embodiments, $P_1$ impairs binding of $A_1$ to the target antigen or cytokine receptor by non-steric blocking. In some embodiments, $P_1$ impairs binding of $A_1$ to the target antigen or cytokine receptor through covalent interactions. In some embodiments, $P_1$ is not a cytokine, cytokine binding fragment, cytokine mutein, or combinations thereof of the cognate receptor of the cytokine. In some embodiments, $A_1$ is not an antibody or fragment thereof that binds to the cytokine receptor.

In some embodiments, $P_2$ comprises a peptide that impairs binding of the second antigen binding domain to the second target antigen. In some embodiments, $P_2$ comprises a peptide that impairs binding of the second cytokine to the second cytokine receptor. In some embodiments, $P_2$ is bound to $A_2$ through ionic interactions, electrostatic interactions, hydrophobic interactions, $P_1$-stacking interactions, and H-bonding interactions, or a combination thereof. In some embodiments, $P_2$ is bound to $A_2$ at or near a cytokine receptor binding site. In some embodiments, $P_2$ is bound to $A_2$ at or near an antigen binding site. In some embodiments, $P_2$ becomes unbound from $A_2$ when $L_2$ is cleaved by the protease thereby exposing $P_2$ to the second target antigen or second cytokine receptor. In some embodiments, the protease comprises a tumor specific protease. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the serine protease comprises matriptase, urokinase, or hepsin. In some embodiments, $P_2$ impairs binding of $A_2$ to the second target antigen or second cytokine receptor by non-steric blocking. In some embodiments, $P_2$ impairs binding of $A_2$ to the second target antigen or second cytokine receptor through covalent interactions. In some embodiments, $P_2$ is not a cytokine, cytokine binding fragment, cytokine mutein, or combinations thereof of the cognate receptor of the cytokine. In some embodiments, $A_2$ is not an antibody or fragment thereof that binds to the cytokine receptor.

In some embodiments, $P_1$ has less than 70% sequence homology to the target antigen. In some embodiments, $P_1$ has less than 75% sequence homology to the target antigen. In some embodiments, $P_1$ has less than 80% sequence homology to the target antigen. In some embodiments, $P_1$ has less than 85% sequence homology to the target antigen. In some embodiments, $P_1$ has less than 90% sequence homology to the target antigen. In some embodiments, $P_1$ has less than 95% sequence homology to the target antigen. In some embodiments, $P_1$ has less than 98% sequence homology to the target antigen. In some embodiments, $P_1$ has less than 99% sequence homology to the target antigen.

In some embodiments, $P_1$ has less than 70% sequence homology to the cytokine receptor. In some embodiments, $P_1$ has less than 75% sequence homology to the cytokine receptor. In some embodiments, $P_1$ has less than 80% sequence homology to the cytokine receptor. In some embodiments, $P_1$ has less than 85% sequence homology to the cytokine receptor. In some embodiments, $P_1$ has less than 90% sequence homology to the cytokine receptor. In some embodiments, $P_1$ has less than 95% sequence homology to the cytokine receptor. In some embodiments, $P_1$ has less than 98% sequence homology to the cytokine receptor. In some embodiments, $P_1$ has less than 99% sequence homology to the cytokine receptor.

In some embodiments, $P_2$ has less than 70% sequence homology to the second target antigen. In some embodiments, $P_2$ has less than 75% sequence homology to the second target antigen. In some embodiments, $P_2$ has less than 80% sequence homology to the second target antigen. In some embodiments, $P_2$ has less than 85% sequence homology to the second target antigen. In some embodiments, $P_2$ has less than 90% sequence homology to the second target antigen. In some embodiments, $P_2$ has less than 95% sequence homology to the second target antigen. In some embodiments, $P_2$ has less than 98% sequence homology to the second target antigen. In some embodiments, $P_2$ has less than 99% sequence homology to the second target antigen.

In some embodiments, $P_2$ has less than 70% sequence homology to the second cytokine receptor. In some embodiments, $P_2$ has less than 75% sequence homology to the second cytokine receptor. In some embodiments, $P_2$ has less than 80% sequence homology to the second cytokine receptor. In some embodiments, $P_2$ has less than 85% sequence homology to the second cytokine receptor. In some embodiments, $P_2$ has less than 90% sequence homology to the second cytokine receptor. In some embodiments, $P_2$ has less than 95% sequence homology to the second cytokine receptor. In some embodiments, $P_2$ has less than 98% sequence homology to the second cytokine receptor. In some embodiments, $P_2$ has less than 99% sequence homology to the second cytokine receptor.

In some embodiments, $P_1$ or $P_2$ comprises a de novo amino acid sequence that shares less than 50% sequence homology to a cytokine, cytokine receptor, or antibody or fragments thereof that bind to the cytokine or cytokine receptor. In some embodiments, $P_1$ or $P_2$ comprises a de novo amino acid sequence that shares less than 40% sequence homology to a cytokine, cytokine receptor, or antibody or fragments thereof that bind to the cytokine or cytokine receptor. In some embodiments, $P_1$ or $P_2$ comprises a de novo amino acid sequence that shares less than 30% sequence homology to a cytokine, cytokine receptor, or antibody or fragments thereof that bind to the cytokine or cytokine receptor. In some embodiments, $P_1$ or $P_2$ comprises a de novo amino acid sequence that shares less than 20% sequence homology to a cytokine, cytokine receptor, or antibody or fragments thereof that bind to the cytokine or cytokine receptor. In some embodiments, $P_1$ or $P_2$ comprises a de novo amino acid sequence that shares less than 10% sequence homology to a cytokine, cytokine receptor, or antibody or fragments thereof that bind to the cytokine or cytokine receptor. In some embodiments, $P_1$ or $P_2$ is identified from a peptide library that contains random amino acid sequences.

In some embodiments, $P_1$ or $P_2$ comprises a de novo amino acid sequence that shares less than 50% sequence homology to the target antigen. In some embodiments, $P_1$ or $P_2$ comprises a de novo amino acid sequence that shares less than 40% sequence homology to the target antigen. In some embodiments, $P_1$ or $P_2$ comprises a de novo amino acid sequence that shares less than 30% sequence homology to the target antigen. In some embodiments, $P_1$ or $P_2$ comprises a de novo amino acid sequence that shares less than 20% sequence homology to the target antigen. In some embodiments, $P_1$ or $P_2$ comprises a de novo amino acid sequence that shares less than 10% sequence homology to the target antigen. In some embodiments, $P_1$ or $P_2$ is identified from a peptide library that contains random amino acid sequences.

In some embodiments, $P_1$ or $P_2$ comprises a peptide sequence of at least 5 amino acids in length. In some embodiments, $P_1$ or $P_2$ comprises a peptide sequence of at least 6 amino acids in length. In some embodiments, $P_1$ or $P_2$ comprises a peptide sequence of at least 10 amino acids in length. In some embodiments, $P_1$ or $P_2$ comprises a peptide sequence of at least 10 amino acids in length and no more than 20 amino acids in length. In some embodiments, $P_1$ or $P_2$ comprises a peptide sequence of at least 16 amino acids in length. In some embodiments, $P_1$ or $P_2$ comprises a peptide sequence of no more than 40 amino acids in length. In some embodiments, $P_1$ or $P_2$ comprises at least two cysteine amino acid residues. In some embodiments, $P_1$ or $P_2$ comprises a cyclic peptide or a linear peptide. In some embodiments, $P_1$ or $P_2$ comprises a cyclic peptide. In some embodiments, $P_1$ or $P_2$ comprises a linear peptide.

In some embodiments, $P_1$ or $P_2$ comprise a modified amino acid or non-natural amino acid, or a modified non-natural amino acid, or a combination thereof. In some embodiments, the modified amino acid or a modified non-natural amino acid comprises a post-translational modification. In some embodiments $P_1$ or $P_2$ comprise a modification including, but not limited to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to $P_1$ or $P_2$ including the peptide backbone, the amino acid side chains, and the terminus.

In some embodiments, $P_1$ or $P_2$ does not comprise albumin or an albumin fragment. In some embodiments, $P_1$ or $P_2$ does not comprise an albumin binding domain.

$A_1$ and $A_2$

In some embodiments, $A_1$ or $A_2$ is an antigen recognizing molecule. In some embodiments, the antigen recognizing molecule is an antibody or an antibody fragment. In some embodiments, the antibody or the antibody fragment thereof comprises a single chain variable fragment, a single domain antibody, Fab, Fab'. In some embodiments, the antibody or antibody fragment thereof comprises a single chain variable fragment (scFv), a heavy chain variable domain (VH domain), a light chain variable domain (VL domain), or a variable domain (VHH) of a camelid derived single domain antibody. In some embodiments, the antibody or antibody fragment thereof comprises a single-chain variable fragment. In some embodiments, the antibody or antibody fragment thereof is humanized or human.

In some embodiments, $A_1$ or $A_2$ is a Fab. In some embodiments, the Fab comprises (a) a Fab light chain polypeptide; and (b) a Fab heavy chain polypeptide. In some embodiments, $L_1$ or $L_2$ is bound to N-terminus of the Fab light chain polypeptide. In some embodiments, $L_1$ or $L_2$ is bound to N-terminus of the Fab heavy chain polypeptide. In some embodiments, $L_1$ or $L_2$ is bound to C-terminus of the Fab light chain polypeptide. In some embodiments, $L_1$ or $L_2$ is bound to C-terminus of the Fab heavy chain polypeptide.

In some embodiments, $A_1$ or $A_2$ is a single chain variable fragment (scFv). In some embodiments, $L_1$ or $L_2$ is bound to N-terminus of the scFv. In some embodiments, $L_1$ or $L_2$ is bound to C-terminus of the scFv. In some embodiments, the scFv comprises a light chain variable domain and a heavy chain variable domain. In some embodiments, $L_1$ or $L_2$ is bound to a N-terminus of the light chain variable domain of the single chain variable fragment (scFv). In some embodiments, $L_1$ or $L_2$ is bound to a N-terminus of the heavy chain variable domain of the single chain variable fragment (scFv).

In some embodiments, the antibody or antibody fragment thereof comprises an epidermal growth factor receptor (EGFR) binding domain. In some embodiments, the antibody or antibody fragment thereof comprises a cluster of differentiation 3 (CD3) binding domain. In some embodiments, the antibody or antibody fragment thereof comprises a cluster of differentiation 3 epsilon (CDR) binding domain. In some embodiments, the target antigen comprises EGFR. In some embodiments, the target antigen comprises CD3. In some embodiments, the target antigen comprises CD3ε.

In some embodiments, $A_1$ or $A_2$ binds to a polypeptide that is part of a TCR-CD3 complex on the effector cell. In some embodiments, the target antigen is an anti-CD3 effector cell antigen. In some embodiments, the polypeptide that is part of the TCR-CD3 complex is human CD3ε. In some embodiments, $A_1$ or $A_2$ comprises an anti-CD3e single-chain variable fragment. In some embodiments, $A_1$ or $A_2$ comprises an anti-CD3e single-chain variable fragment that has a $K_D$ binding of 1 µM or less to CD3 on CD3 expressing cells. In some embodiments, $A_1$ or $A_2$ comprises a variable light chain and variable heavy chain each of which is capable of specifically binding to human CD3. In some embodiments, $A_1$ or $A_2$ comprises complementary determining regions (CDRs) selected from the group consisting of muromonab-CD3 (OKT3), otelixizumab (TRX4), teplizumab (MGA031), visilizumab (Nuvion), SP34, X35, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1, WT-31, 15865, 15865v12, 15865v16, and 15865v19.

In some embodiments, $A_1$ or $A_2$ is a soluble T cell receptor (TCR). Native TCRs are transmembrane receptors expressed on the surface of T cells that recognize antigens bound to major histocompatibility complex molecules (MHC). Native TCRs are heterodimeric and comprise an alpha polypeptide chain and a beta polypeptide chain linked through a disulfide bond. The alpha polypeptide chain and the beta polypeptide chain are expressed as part of a complex with accessory proteins which include, for example, two CD3 epsilon polypeptides, one CD3 gamma polypeptide, one CD3 delta polypeptide, and two CD3 zeta polypeptides. When a TCR engages with a target antigen and MHC, the T cell is activated resulting in a series of signaling events mediated by associated enzymes, co-receptors, adapter molecules, and activated or released transcription factors.

In native TCRs, the alpha polypeptide chain and the beta polypeptide chain comprise an extracellular domain, a transmembrane domain, and a cytoplasmic domain. Each extracellular domain comprises a variable region (V), a joining region (J), and a constant region (C). The constant region is N-terminal to the transmembrane domain, and the transmembrane domain is N-terminal to the cytoplasmic domain. The variable regions of both the alpha polypeptide chain and the beta polypeptide chain comprise three hypervariable or complementarity determining regions (CDRs). The beta polypeptide chain usually contains a short diversity region between the variable and joining regions. The three CDRs are embedded into a framework sequence, with one CDR being the hypervariable region named CDR3. The alpha chain variable region (Vα) and the beta chain variable region (Vβ) are of several types that are distinguished by their framework sequences, CDR1 and CDR2 sequences, and a partly defined CDR3 sequence.

TCRs are described using the International Immunogenetics (IMGT) TCR nomenclature. The Vα in IMGT nomenclature is referred to by a unique "TRAV" number. In the same way, Vβ is referred to by a unique "TRBV" number. The corresponding joining and constant regions are referred to as TRAJ and TRAC, respectively for the α joining and constant regions, and TRBJ and TRBC, respectively for the β joining and constant regions. The sequences defined by the IMGT nomenclature are known in the art and are contained within the online IMGT public database.

In some embodiments, the soluble TCR is a single chain TCR comprising a variable region of a TCR alpha extracellular domain, or fragment thereof, and a variable region of a TCR beta extracellular domain, or fragment thereof. In some embodiments, the soluble TCR comprises an alpha TCR polypeptide comprising a TCR alpha extracellular domain and a beta TCR polypeptide comprising a TCR beta extracellular domain.

In some embodiments, the soluble TCR is a single chain TCR comprising a variable region of a TCR alpha extracellular domain, or fragment thereof, and a variable region of a TCR beta extracellular domain, or fragment thereof. In some embodiments, the soluble TCR comprises an alpha TCR polypeptide comprising a TCR alpha extracellular domain and a beta TCR polypeptide comprising a TCR beta extracellular domain. In some embodiments, $L_1$ is bound to N-terminus of the alpha TCR polypeptide. In some embodiments, $L_1$ is bound to N-terminus of the beta TCR polypeptide. In some embodiments, $A_2$ is bound to C-terminus of the alpha TCR polypeptide. In some embodiments, $A_2$ is bound to N-terminus of the alpha TCR polypeptide. In some embodiments, $A_2$ is bound to C-terminus of the beta TCR polypeptide. In some embodiments, $A_2$ is bound to N-terminus of the beta TCR polypeptide. In some embodiments, $L_1$ is bound to N-terminus of the alpha TCR polypeptide and $A_2$ is bound to N-terminus of the beta TCR polypeptide. In some embodiments, $L_1$ is bound to N-terminus of the alpha TCR polypeptide and $A_2$ is bound to C-terminus of the beta TCR polypeptide. In some embodiments, $L_1$ is bound to N-terminus of the alpha TCR polypeptide and $A_2$ is bound to C-terminus of the alpha TCR polypeptide. In some embodiments, L 1 is bound to N-terminus of the beta TCR polypeptide and $A_2$ is bound to N-terminus of the alpha TCR polypeptide. In some embodiments, $L_1$ is bound to N-terminus of the beta TCR polypeptide and $A_2$ is bound to C-terminus of the beta TCR polypeptide. In some embodiments, $L_1$ is bound to N-terminus of the beta TCR polypeptide and $A_2$ is bound to C-terminus of the alpha TCR polypeptide.

In some embodiments, the polypeptide or polypeptide complex has weaker binding affinity for the target antigen or second target antigen as compared to the binding affinity for the target antigen or second target antigen of a polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 5× higher than the binding affinity for the target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 8× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 10× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 20× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 25× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 30× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 40× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 50× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 60× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 70× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 75× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 80× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 90× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 100× higher than the binding affinity for the target antigen or second target antigen of a form of the polypeptide or polypeptide complex that does not have $P_1$ or $P_2$ or $L_1$ or $L_2$. In some embodiments, the polypeptide or polypeptide complex has weaker binding affinity for the target antigen or second target antigen that is at least 120× higher than the binding affinity for the target antigen or second target antigen of a form of the polypeptide or polypeptide complex that does not have $P_1$ or $P_2$ or $L_1$ or $L_2$.

In some embodiments, the polypeptide or polypeptide complex has weaker binding affinity for the target antigen or second target antigen as compared to the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 5× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 8× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 10× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 20× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 25× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 30× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 40× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 50× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 60× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 70× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 75× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 80× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 90× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 100× higher than the binding affinity for the target antigen or second target antigen of the polypeptide or polypeptide complex in which $L_1$ or $L_2$ has been cleaved. In some embodiments, the polypeptide or polypeptide complex has weaker binding affinity for the target antigen or second target antigen that is at least 120× higher than the binding affinity for the target antigen or second target antigen of the polypeptide or polypeptide complex in which $L_1$ or $L_2$ has been cleaved. In some embodiments, $L_1$ or $L_2$ is cleaved by a protease. In some embodiments, the protease comprises a tumor specific protease. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the serine protease comprises matriptase, urokinase, or hepsin.

In some embodiments, $A_1$ or $A_2$ is a cytokine or cytokine fragment. In some embodiments, $A_1$ or $A_2$ is a mutein of the cytokine or the cytokine fragment. In some embodiments, the cytokine or the cytokine fragment is a mutein of the cytokine or the cytokine fragment.

Cytokines are a diverse group of small peptides, including chemokines, interferons, interleukins, lymphokines, adipokines, mesenchymal growth factors, and tumor necrosis factors, which are involved in intercellular signaling in a variety of biological pathways. They are particularly important in immune and inflammatory responses. Signaling occurs following recognition of the cytokine by a corresponding cytokine receptor, which are transmembrane receptors comprising an extracellular domain for ligand binding and an intracellular domain that allows signal transduction.

The diversity of cytokines comes with a corresponding diversity in cytokine receptors, which can comprise a single chain or subunit or dimeric/multimeric domains. Cytokine receptors include Type I cytokine receptors, exemplified by interleukin receptors, and Type II cytokine receptors, exemplified by interferon receptors, both of which comprise a cytokine receptor homology domain (CHD). The CHD of Type I cytokine receptors share a common amino acid motif (WSXWS (SEQ ID NO: 27)), while Type II cytokine receptors lack this motif. Cytokine receptors can include an alpha subunit, beta subunit, gamma subunit, or dimeric, or trimeric combinations thereof. In one example, a high affinity receptor for IL-2 comprises an IL-2Rα subunit, IL-2Rβ subunit, and IL-2Rγ subunit, an intermediate affinity receptor for IL-2 comprises only the IL-2Rβ subunit and IL-2Rγ subunit, and low affinity receptor for IL-2 comprises only the IL-2Rα subunit.

In some embodiments, the cytokine is a chemokine, an interferon, an interleukin, a lymphokine, an adipokine, a growth factor, or a tumor necrosis factor. In some embodiments, the interferon (IFN) is IFNα, IFNβ, IFNγ, or a fragment thereof. In some embodiments, the interleukin (IL) is IL-2, IL-4, IL-6, IL-7, IL-10, IL-12, IL-15, IL-21, or a fragment thereof. In some embodiments, the growth factor is granulocyte-macrophage colony-stimulating factor (GM-CSF) or a fragment thereof. In some embodiments the cytokine is TGF-β.

In some embodiments, a cytokine mutein is a variant of a wild-type cytokine. In some embodiments, a cytokine mutein is a mutant of a wild-type cytokine. In some embodiments, the cytokine mutein comprises at least 1, 2, 3, 4, 5, 6, 7, 8, 9, 10, 20, 30, 40, 50, or more than 50 amino acid substitutions relative to a wild-type cytokine. In some embodiments, the cytokine mutein comprises no more than 2, 3, 4, 5, 6, 7, 8, 9, 10, 20, 30, 40, 50, or more than 50 amino acid substitutions relative to a wild-type cytokine. In some embodiments, the cytokine mutein is a non-naturally occurring cytokine. In some embodiments, the cytokine mutein comprises at least 1, 2, 3, 4, 5, 6, 7, 8, 9, 10, 20, 30, 40, 50, or more than 50 amino acid substitutions relative to a naturally occurring cytokine. In some embodiments, the cytokine mutein comprises no more than 2, 3, 4, 5, 6, 7, 8, 9, 10, 20, 30, 40, 50, or more than 50 amino acid substitutions relative to a naturally occurring cytokine.

In some embodiments, the cytokine or cytokine fragment binds to a cytokine receptor. In some embodiments, the cytokine receptor is a receptor for a chemokine, an interferon, an interleukin, a lymphokine, an adipokine, a growth factor, or a tumor necrosis factor. In some embodiments, the cytokine receptor is a type I cytokine receptor or a type II cytokine receptor. In some embodiments, the cytokine receptor is a dimer or a trimer. In some embodiments, the cytokine receptor comprises an alpha subunit, a beta subunit, a gamma subunit, or any combination thereof. For example, in some embodiments, the cytokine receptor comprises an alpha subunit, a beta subunit, and a gamma subunit. In another example, in some embodiments, the cytokine receptor comprises a beta subunit and a gamma subunit. In some embodiments, the cytokine receptor comprises an alpha subunit and a beta subunit.

In some embodiments, the polypeptide or polypeptide complex has a weaker binding affinity for its cytokine receptor as compared to the binding affinity for the cytokine receptor of a polypeptide or polypeptide complex that does not have $P_1$ or $P_2$ or $L_1$ or $L_2$. In some embodiments, the polypeptide or polypeptide complex has weaker binding affinity for its cytokine receptor that is at least 5× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 8× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 10× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 20× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 25× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 30× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 40× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 50× weaker than the binding affinity for the cytokine receptor of a form of the polypeptide or polypeptide complex that does not have $P_1$ or $P_2$ or $L_1$ or $L_2$In some embodiments, the polypeptide or polypeptide complex has weaker binding affinity for its cytokine receptor that is at least 60× weaker than the binding affinity for the cytokine receptor of a form of the polypeptide or polypeptide complex that does not have $P_1$ or $P_2$ or $L_1$ or $L_2$In some embodiments, the polypeptide or polypeptide complex has weaker binding affinity for its cytokine receptor that is at least 70× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 75× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 80× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 90× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 100× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 120× weaker than the binding affinity for the cytokine receptor of a form of the polypeptide or polypeptide complex that does not have $P_1$ or $P_2$ or $L_1$ or $L_2$. In some embodiments, the polypeptide or polypeptide complex has weaker binding affinity for its cytokine receptor that is at least 150× weaker than the binding affinity for the cytokine receptor of a form of the polypeptide or polypeptide complex that does not have $P_1$ or $P_2$ or $L_1$ or $L_2$. In some embodiments, the cytokine or cytokine fragment comprises an interferon, GM-CSF, IL-2, IL-7, IL-12, IL-15, or IL-21. In some embodiments, the cytokine or cytokine fragment comprises IL-2, IL-12, IL-6, IL-4, IL-10, or TGF-p. In some embodiments, the cytokine receptor comprises an interferon receptor, GM-CSF receptor, IL-2 receptor, IL-7 receptor, IL-12 receptor, IL-15 receptor, or IL-21 receptor. In some embodiments, the cytokine receptor comprises IL-2 receptor, IL-12 receptor, IL-6 receptor, IL-4 receptor, IL-10 receptor, or TGF-β receptor.

In some embodiments, the polypeptide or polypeptide complex has weaker binding affinity for its cytokine receptor as compared to the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 5× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 8× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 10× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 15× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 20× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 25× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 30× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 40× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 50× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 60× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 70× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 75× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 80× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 90× weaker than the binding affinity for the cytokine receptor of the polypeptide or polypeptide complex in which $L_1$ or $L_2$ has been cleaved. In some embodiments, the polypeptide or polypeptide complex has weaker binding affinity for its cytokine receptor that is at least 100× weaker than the binding affinity for the cytokine receptor of the polypeptide or polypeptide complex in which $L_1$ or $L_2$ has been cleaved. In some embodiments, the cytokine or cytokine fragment comprises an interferon, GM-CSF, IL-2, IL-7, IL-12, IL-15, or IL-21. In some embodiments, the cytokine receptor comprises an interferon receptor, GM-CSF receptor, IL-2 receptor, IL-7 receptor, IL-12 receptor, IL-15 receptor, or IL-21 receptor. In some embodiments, $L_1$ or $L_2$ is cleaved by a protease. In some embodiments, the protease comprises a tumor specific protease. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the serine protease comprises matriptase, urokinase, or hepsin.

Half-Life Extending Moiety

In some embodiments, $P_1$ is further linked to a half-life extending moiety. In some embodiments, $P_1$ is further linked to a half-life extending moiety in a configuration according to Formula Ia

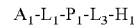  (Formula Ia)

wherein $H_1$ is the half-life extending moiety and $L_3$ is a linker that connects $H_1$ to $P_1$. In some embodiments, $L_3$ is a non-cleavable linker. In some embodiments, the half-life extending moiety ($H_1$) does not block $A_1$ binding to the target antigen. In some embodiments, the half-life extending moiety ($H_1$) does not have binding affinity to $A_1$. In some embodiments, the half-life extending moiety ($H_1$) does not have binding affinity to the target antigen. In some embodiments, the half-life extending moiety ($H_1$) does not shield $A_1$ from the target antigen. In some embodiments, the half-life extending moiety ($H_1$) is not directly linked to $A_1$.

In some embodiments, the half-life extending moiety ($H_1$) does not block $A_1$ binding to the cytokine receptor. In some embodiments, the half-life extending moiety ($H_1$) does not have binding affinity to the cytokine or cytokine receptor. In some embodiments, the half-life extending moiety ($H_1$) does not shield the cytokine or cytokine fragment from the cytokine receptor. In some embodiments, the half-life extending moiety ($H_1$) is not directly linked to the cytokine or cytokine fragment.

In some embodiments, $H_1$ comprises an amino acid sequence that has repetitive sequence motifs. In some embodiments, $H_1$ comprises an amino acid sequence that has highly ordered secondary structure. "Highly ordered secondary structure," as used in this context, means that at least about 50%, or about 70%, or about 80%, or about 90%, of amino acid residues of $H_1$ contribute to secondary structure, as measured or determined by means, including, but not limited to, spectrophotometry (e.g. by circular dichroism spectroscopy in the "far-UV" spectral region (190-250 nm), and computer programs or algorithms, such as the Chou-Fasman algorithm and the Garnier-Osguthorpe-Robson ("GOR") algorithm.

In some embodiments, $H_1$ comprises a polymer. In some embodiments, the polymer is polyethylene glycol (PEG). In some embodiments, $H_1$ comprises albumin. In some embodiments, $H_1$ comprises a Fc domain. In some embodiments, the albumin is serum albumin. In some embodiments, the albumin is human serum albumin. In some embodiments, $H_1$ comprises a polypeptide, a ligand, or a small molecule. In some embodiments, the polypeptide, the ligand or the small molecule binds serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, sIgA, IgM or IgD. In some embodiments, the serum protein is albumin. In some embodiments, the polypeptide is an antibody. In some embodiments, the antibody comprises a single domain antibody, a single chain variable fragment or a Fab. In some embodiments, the antibody comprises a single domain antibody. In some embodiments, the antibody comprises a single domain antibody that binds to albumin. In some embodiments, the antibody comprises a single domain antibody that binds to human serum albumin. In some embodiments, the antibody is a human or humanized antibody. In some embodiments, the single domain antibody is selected from the group consisting of 645gH1gL1, 645dsgH5gL4, 23-13-A01-sc02, A10m3 or a fragment thereof, DOM7r-31, DOM7h-11-15, Alb-1, Alb-8, Alb-23, 10G, 10GE, and SA21.

In some embodiments, $H_1$ comprises a single domain antibody. In some embodiments, $H_1$ comprises a single domain antibody that binds to albumin. In some embodiments, $H_1$ comprises a single domain antibody that binds to human serum albumin.

In some embodiments, $H_1$ comprise a modified amino acid or non-natural amino acid, or a modified non-natural amino acid, or a combination thereof. In some embodiments, the modified amino acid or a modified non-natural amino acid comprises a post-translational modification. In some embodiments, $H_1$ comprise a modification including, but not limited to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to $H_1$ including the peptide backbone, the amino acid side chains, and the terminus.

Polynucleotides Encoding Polypeptides or Polypeptide Complexes

Disclosed herein, in some embodiments, are isolated recombinant nucleic acid molecules encoding polypeptides or polypeptide complexes as disclosed herein. Described herein, in some embodiments, are isolated recombinant nucleic acid molecules encoding polypeptides comprising a cleavable linker.

As disclosed herein, in some embodiments, are isolated recombinant nucleic acid molecules encoding polypeptides comprising a cleavable linker according to the amino acid sequence of SEQ ID NO: 1 (LSGRSDAG).

In some embodiments, the cleavable linker comprises the amino acid sequence of SEQ ID NO: 3 (ISSGLLSGRSDAG). In some embodiments, the cleavable linker comprises the amino acid sequence of SEQ ID NO: 26 (AGLLAPPGGLSGRSDAG). In some embodiments, the cleavable linker comprises the amino acid sequence of SEQ ID NO: 4 (AAGLLAPPGGLSGRSDAG). In some embodiments, the cleavable linker comprises the amino acid sequence of SEQ ID NO: 5 (SPLGLSGRSDAG). In some embodiments, the cleavable linker comprises the amino acid sequence of SEQ ID NO: 6 (LSGRSDAGSPLGLAG).

Disclosed herein, in some embodiments, are isolated recombinant nucleic acid molecules encoding an isolated polypeptide comprising a cleavable linker according to the amino acid sequence of Linker 1 (ISSGLLSGRSDAG) (SEQ ID NO: 3), Linker 2 (AAGLLAPPGGLSGRSDAG) (SEQ ID NO: 4), Linker 3 (SPLGLSGRSDAG) (SEQ ID NO: 5), or Linker 4 (LSGRSDAGSPLGLAG) (SEQ ID NO: 6), or an isolated polypeptide comprising a cleavable linker that has 1, 2, or 3 amino acid substitutions, additions, or deletions relative to the amino acid sequence of Linker 1, Linker 2, Linker 3, or Linker 4. Disclosed herein, in some embodiments, are isolated recombinant nucleic acid molecules encoding an isolated polypeptide comprising a cleavable linker according to the amino acid sequence of Linker 1 (ISSGLLSGRSDAG) (SEQ ID NO: 3). Disclosed herein, in some embodiments, are isolated recombinant nucleic acid molecules encoding an isolated polypeptide comprising a cleavable linker according to the amino acid sequence of Linker 2 (AAGLLAPPGGLSGRSDAG) (SEQ ID NO: 4). Disclosed herein, in some embodiments, are isolated recombinant nucleic acid molecules encoding an isolated polypeptide comprising a cleavable linker according to the amino acid sequence of Linker 3 (SPLGLSGRSDAG) (SEQ ID NO: 5). Disclosed herein, in some embodiments, are isolated recombinant nucleic acid molecules encoding an isolated polypeptide comprising a cleavable linker according to the amino acid sequence of Linker 4 (LSGRSDAGSPLGLAG) (SEQ ID NO: 6). Disclosed herein, in some embodiments, are isolated recombinant nucleic acid molecules encoding an isolated polypeptide comprising a cleavable linker according to the the amino acid sequence LSGRSDAG (SEQ ID NO: 1).

Disclosed herein, in some embodiments, are isolated recombinant nucleic acid molecules encoding polypeptides or polypeptide complexes according to Formula I:

$$A_1\text{-}L_1\text{-}P_1 \quad \text{(Formula I)}$$

wherein $A_1$ comprises the antigen binding domain that binds to the target antigen or the cytokine that binds to the cytokine receptor; $L_1$ comprises the cleavable linker; and $P_1$ comprises a peptide that impairs binding of the antigen binding domain to the target antigen or impairs binding of the cytokine to the cytokine receptor. Disclosed herein, in some embodiments, are isolated recombinant nucleic acid molecules encoding polypeptides or polypeptide complexes comprising Formula I:

$$A_1\text{-}L_1\text{-}P_1 \qquad \text{(Formula I)}$$

wherein $A_1$ comprises the antigen binding domain that binds to the target antigen or the cytokine that binds to the cytokine receptor; $L_1$ comprises the cleavable linker; and $P_1$ comprises a peptide that impairs binding of the antigen binding domain to the target antigen or impairs binding of the cytokine to the cytokine receptor. Disclosed herein, in some embodiments, are isolated recombinant nucleic acid molecules enco LAPPGGLSGRSDAG) (SEQ ID NO: 4) and (b) a pharmaceutically acceptable excipient. In some embodiments, the pharmaceutical composition comprises (a the polypeptides or polypeptide complexes comprising a cleavable linker according to the amino acid sequence of Linker 3 (SPLGLSGRSDAG) (SEQ ID NO: 5) and (b) a pharmaceutically acceptable excipient. In some embodiments, the pharmaceutical composition comprises (a) the polypeptides or polypeptide complexes comprising a cleavable linker according to the amino acid sequence of Linker 4 (LSGRSDAGSPLGLAG) (SEQ ID NO: 6) and (b) a pharmaceutically acceptable excipient. In some embodiments, the pharmaceutical composition comprises (a) the polypeptides or polypeptide complexes comprising a cleavable linker according to the amino acid sequence LSGRSDAG (SEQ ID NO: 1) and (b) a pharmaceutically acceptable excipient.

In some embodiments, the pharmaceutical composition comprises (a) isolated polypeptide polypeptides or polypeptide complexes according to Formula I:

$$A_1\text{-}L_1\text{-}P_1 \quad \text{(Formula I)}$$

wherein $A_1$ comprises the antigen binding domain that binds to the target antigen or the cytokine that binds to the cytokine receptor; $L_1$ comprises the cleavable linker; and $P_1$ comprises a peptide that impairs binding of the antigen binding domain to the target antigen or impairs binding of the cytokine to the cytokine receptor; and (b) a pharmaceutically acceptable excipient. In some embodiments, the pharmaceutical composition comprises (a) isolated polypeptide polypeptides or polypeptide complexes comprising Formula I:

$$A_1\text{-}L_1\text{-}P_1 \quad \text{(Formula I)}$$

wherein $A_1$ comprises the antigen binding domain that binds to the target antigen or the cytokine that binds to the cytokine receptor; $L_1$ comprises the cleavable linker; and $P_1$ comprises a peptide that impairs binding of the antigen binding domain to the target antigen or impairs binding of the cytokine to the cytokine receptor; and (b) a pharmaceutically acceptable excipient. In some embodiments, the pharmaceutical composition comprises (a) isolated polypeptide polypeptides or polypeptide complexes according to Formula I:

$$A_1\text{-}L_1\text{-}P_1 \quad \text{(Formula I)}$$

wherein $A_1$ is the antigen binding domain that binds to the target antigen or the cytokine that binds to the cytokine receptor; $L_1$ is the cleavable linker; and $P_1$ is a peptide that impairs binding of the antigen binding domain to the target antigen or impairs binding of the cytokine to the cytokine receptor; and (b) a pharmaceutically acceptable excipient. In some embodiments, the pharmaceutical composition comprises (a) isolated polypeptide polypeptides or polypeptide complexes comprising Formula I:

$$A_1\text{-}L_1\text{-}P_1 \quad \text{(Formula I)}$$

wherein $A_1$ is the antigen binding domain that binds to the target antigen or the cytokine that binds to the cytokine receptor; $L_1$ is the cleavable linker; and $P_1$ is a peptide that impairs binding of the antigen binding domain to the target antigen or impairs binding of the cytokine to the cytokine receptor; and (b) a pharmaceutically acceptable excipient.

Disclosed herein, in some embodiments, are polypeptides or polypeptide complexes, wherein the isolated polypeptide is complexed with a second isolated polypeptide comprising a second antigen binding domain or a second cytokine. In some embodiments, the pharmaceutical composition comprises (a) isolated polypeptide polypeptides or polypeptide complexes according to Formula II:

$$A_2\text{-}L_2\text{-}P_2 \quad \text{(Formula II)}$$

wherein $A_2$ comprises the second antigen binding domain or the second cytokine; $L_2$ comprises a second cleavable linker; and $P_2$ comprises a second peptide that impairs binding of the second antigen binding domain to a second target antigen or impairs binding of the second cytokine to a second cytokine receptor; and (b) a pharmaceutically acceptable excipient. In some embodiments, the pharmaceutical composition comprises (a) isolated polypeptide polypeptides or polypeptide complexes comprising Formula II:

$$A_2\text{-}L_2\text{-}P_2 \ ganisms may be ensured by the inclusion of various antibacterial and antifungal agents.

The pharmaceutical composition may be in any suitable form, (depending upon the desired method of administration). It may be provided in unit dosage form, may be provided in a sealed container and may be provided as part of a kit. Such a kit may include instructions for use. It may include a plurality of said unit dosage forms.

The pharmaceutical composition may be adapted for administration by any appropriate route, including a parenteral (e.g., subcutaneous, intramuscular, or intravenous) route. Such compositions may be prepared by any method known in the art of pharmacy, for example by mixing the active ingredient with the carrier(s) or excipient(s) under sterile conditions.

Dosages of the substances of the present disclosure can vary between wide limits, depending upon the disease or disorder to be treated, the age and condition of the individual to be treated, etc. and a physician will ultimately determine appropriate dosages to be used.

Table 1 provides the amino acid sequences of constructs described herein.

TABLE 1

Summary of Amino Acid Sequences

| Construct ID | Construct Description | Amino Acid Sequence (N to C) | SEQ ID NO: |
|---|---|---|---|
| LINKER SEQUENCES | | | |
| Linker-0 | Cleavable linker (control) | ISSGLLSGRSDNH | 2 |
| Linker-1 | Cleavable linker | ISSGLLSGRSDAG | 3 |
| Linker-2 | Cleavable linker | AAGLLAPPGGLSGRSDAG | 4 |
| Linker-3 | Cleavable linker | APLGLSGRSDAG | 5 |
| Linker-4 | Cleavable linker | LSGRSDAGSPLGLAG | 6 |
| Linker-5 | Cleavable linker | LSGRSDAG | 1 |
| Linker-6 | Cleavable linker | AGLLAPPGGLSGRSDAG | 26 |
| PEPTIDE MASK SEQUENCES | | | |
| Peptide-1 | anti-EGFR peptide mask | QGQSGQLSCEGWAMNREQCRA | 7 |
| Ppetide-2 | anti-EGFR peptide mask | GGPCRSHIDVAKPICV | 8 |
| Peptide-3 | anti-CD3 peptide mask | QGQSGQGYLWGCEWNCGGITT | 9 |
| Peptide-4 | anti-CD3 peptide mask | QGQSGSGYLWGCEWNCAGITT | 10 |
| HALF-LIFE EXTENDING MOIETIES | | | |
| HE-1 | 10G single domain antibody | EVQLVESGGGLVQPGNSLRLSCAASGFTFSKFGMSWVRQAPGKGL EWVSSISGSGRDTLYADSVKGRFTISRDNAKTTLYLQMNSLRPED TAVYYCTIGGSLSVSSQGTLVTVSS | 11 |
| FULL LENGTH CONSTRUCTS | | | |
| PC-1 | Light Chain Sequence: N-[Peptide-1]-[Linker-0]-[anti-EGFR Fab light chain]-C (control) | QGQSGQLSCEGWAMNREQCRAGSSGGSGGSGGSGISSGLLSGRSD NHGSSGTDILLTQSPVILSVSPGERVSFSCRASQSIGTNIHWYQQ RTNGSPRLLIKYASESISGIPSRFSGSGSGTDFTLSINSVESEDI ADYYCQQNNNWPTTFGAGTKLELKRTVAAPSVFIFPPSDEQLKSG TASVVCLLNNFYPREAKVQWKVDNALQSGNSQESVTEQDSKDSTY SLSSTLTLSKADYEKHKVYACEVTHQGLSSPVTKSFNRGEC | 12 |
| PC-1 | Heavy Chain Sequence: N-[10G SDA]-[Peptide-3]-[Linker-0]-[anti-CD3 scFv light chain-heavy chain)]-[anti-EGFR Fab heavy chain]-C (control) | EVQLVESGGGLVQPGNSLRLSCAASGFTFSKFGMSWVRQAPGKGL EWVSSISGSGRDTLYADSVKGRFTISRDNAKTTLYLQMNSLRPED TAVYYCTIGGSLSVSSQGTLVTVSSGGGGSGGGSQGQSGQYLWG CEWNCGGITTGSSGGSGGSGGISSGLLSGRSDNHGGGSQTVVTQE PSLTVSPGGTVTLTCRSSTGAVTTSNYANWVQQKPGQAPRGLIGG TNKRAPGTPARFSGSLLGGKAALTLSGVQPEDEAEYYCALWYSNL WVFGGGTKLTVLGGGGSGGGGSGGGGSEVQLVESGGGLVQPGGSL KLSCAASGFTFNTYAMNWVRQAPGKGLEWVARIRSKYNNYATYYA DSVKDRFTISRDDSKNTAYLQMNNLKTEDTAVYYCVRHGNFGNSY VSWFAYWGQGTLVTVSSGGGGSQVQLKQSGPGLVQPSQSLSITCT VSGFSLTNYGVHWVRQSPGKLGEWLGVIWSGGNTDYNTPFTSRLS INKDNSKSQVFFKMNSLQSNDTAIYYCARALTYYDYEFAYWGQGT LVTVSAASTKGPSVFPLAPSSKSTSGGTAALGCLVKDYFPEPVTV SWNSGALTSGVHTFPAVLQSSGLYSLSSVVTVPSSSLGTQTYICN VNHKPSNTKVDKKVEPKSCGGHHHHHHHGGGLNDIFEAQKIEWH E | 13 |
| PC-2 | Light Chain Sequence: N-[Peptide-2]-[Linker-1]-[anti-EGFR Fab light chain]-C | GGPCRSHIDVAKPICVGGGGSGGGSISSGLLSGRSDAGGGGSDILL TQSPVILSVSPGERVSFSCRASQSIGTNIHWYQQRTNGSPRLLIK YASESISGIPSRFSGSGSGTDFTLSINSVESEDIADYYCQQNNNW PTTFGAGTKLELKRTVAAPSVFIFPPSDEQLKSGTASVVCLLNNF YPREAKVQWKVDNALQSGNSQESVTEQDSKDSTYSLSSTLTLSKA DYEKHKVYACEVTHQGLSSPVTKSFNRGEC | 14 |

TABLE 1-continued

Summary of Amino Acid Sequences

| Construct ID | Construct Description | Amino Acid Sequence (N to C) | SEQ ID NO: |
|---|---|---|---|
| PC-2 | Heavy Chain Sequence: N-[10G SDA]-[Peptide-4]-[Linker-1]-[anti-CD3 scFv (light chain-heavy chain)]-[anti-EGFR Fab heavy chain]-C | EVQLVESGGGLVQPGNSLRLSCAASGFTFSKFGMSWVRQAPGKGL EWVSSISGSGRDTLYADSVKGRFTISRDNAKTTLYLQMNSLRPED TAVYYCTIGGSLSVSSQGTLVTVSSGGGGSGGGGSQGQSGQGYLWG CEWNCAGITTGSSGGSGGGGISSGLLSGRSDAGGGGSQTVVTQE PSLTVSPGGTVTLTCRSSTGAVTTSNYANWVQQKPGQAPRGLIGG TNKRAPGTPARFSGSLLGGKAALTLSGVQPEDEAEYYCALWYSNL WVFGGGTKLTVLGGGGSGGGGSGGGGSEVQLVESGGGLVQPGGSL KLSCAASGFTFNTYAMNWVRQAPGKGLEWVARIRSKYNNYATYYA DSVKDRFTISRDDSKNTAYLQMNNLKTEDTAVYYCVRHGNFGSNY VSWFAYWGQGTLVTVSSGGGGSQVQLKQSGPGLVQPSQSLSITCT VSGFSLTNYGVHWVRQSPGKGLEWLGVIWSGGNTDYNTPFTSRLS INKDNSKSQVFFKMNSLQSNDTAIYYCARALTYYDYEFAYWGQGT LVTVSAASTKGPSVFPLAPSSKSTSGGTAALGCLVKDYFPEPVTV SWNSGALTSGVHTFPAVLQSSGLYSLSSVVTVPSSSLGTQTYICN VNHKPSNTKVDKKVEPKSCAAHHHHHHHH | 15 |
| PC-3 | Light Chain Sequence: N-[Peptide-2]-[Linker-2]-[anti-EGFR Fab light chain]-C | GGPCRSHIDVAKPICVGGGGSSGGSAAGLLAPPGGLSGRSDAGGG GSDILLTQSPVILSVSPFERVSFSCRASQSIGTNIHWYQQRTNGS PRLLIKYASESISGIPSRFSGSGSGTDFTLSINSVESEDIADYYC QQNNNWPTTFGAGTKLELKRTVAAPSVFIFPPSDEQLKSGTASVV CLLNNFYPREAKVQWKVDNALQSGNSQESVTEQDSKDSTYSLSST LTLSKADYEKHKVYACEVTHQGLSSPVTKSFNRGEC | 16 |
| PC-3 | Heavy Chain Sequence: N-[10G SDA]-[Peptide-4]-[linker Linker-2]-[anti-CD3 scFv (light chain-heavy chain)]-[anti-EGFR Fab heavy chain]-C | EVQLVESGGGLVQPGNSLRLSCAASGFTFSKFGMSWVRQAPGKGL EWVSSISGSGRDTLYADSVKGRFTISRDNAKTTLYLQMNSLRPED TAVYYCTIGGSLSVSSQGTLVTVSSGGGGSGGGGSQGQSGQGYLWG CEWNCAGITTGSSGGSAAGLLAPPGGLSGRSDAGGGGSQTVVTQE PSLTVSPGGTVTLTCRSSTGAVTTSNYANWVQQKPGQAPRGLIGG TNKRAPGTPARFSGSLLGGKAALTLSGVQPEDEAEYYCALWYSNL WVFGGGTKLTVLGGGGSGGGGSGGGGSEVQLVESGGGLVQPGGSL KLSCAASGFTGNTYAMNWVRQAPGKGLEWVARIRSKYNNYATYYA DSVKDRFTISRDDSKNTAYLQMNNLKTEDTAVYYCVRHGNFGNSY VSWFAYWGQGTLVTVSSGGGGSQVQLKQSGPGLVQPSQSLSITCT VSGFSLTNYGVHWVRQSPGKGLEWLGVIWSGGNTDYNTPFTSRLS INKDNSKSQVFFKMNSLQSNDTAIYYCARALTYYDYEFAYWGQGT LVTVSAASTKGPSVFPLAPSSKSTSGGTAALGCLVKDYFPEPVTV SWNSGALTSGVHTFPAVLQSSGLYSLSSVVTVPSSSLGTQTYICN VNHKPSNTKVDKKVEPKSCAAHHHHHHHH | 17 |
| PC-4 | Light Chain Sequence: N-[Peptide-2]-[Linker-3]-[anti-EGFR Fab light chain]-C | GGPCRSHIDVAKPICVGGGGSGGGGSPLGLSGRSDAGGGGSDILL TQSPVILSVSPGERVSFSCRASQSIGTNIHWYQQRTNGSPRLLIK YASESISGIPSRFSGSGSGTDFTLSINSVESEDIADYYCQQNNNW PTTFGAGTKLELKRTVAAPSVFIFPPSDEQLKSGTASVVCLLNNF YPREAKVQWKVDNALQSGNSQESVTEQDSKDSTYSLSSTLTLSKA DYEKHKVYACEVTHQGLSSPVTKSFNRGEC | 18 |
| PC-4 | Heavy Chain Sequence: N-[10G SDA]-[Peptide-4]-[Linker-3]-[anti-CD3 scFv (light chain-heavy chain)]-[anti-EGFR Fab heavy chain]-C | EVQLVESGGGLVQPGNSLRLSCAASGFTFSKFGMSWVRQAPGKGL EWVSSISGSGRDTLYADSVKGRFTISRDNAKTTLYLQMNSLRPED TAVYYCTIGGSLSVSSQGTLVTVSSGGGGSGGGGSQGQSGQGYLWG CEWNCAGITTGSSGGSGGGSGGSPLGLSGRSDAGGGGSQTVVTQE PSLTVSPGGTVTLTCRSSTGAVTTSNYANWVQQKPGQAPRGLIGG TNKRAPGTPARFSGSLLGGKAALTLSGVQPEDEAEYYCALWYSNL WVFGGGTKLTVLGGGGSGGGGSGGGGSEVQLVESGGGLVQPGGSL KLSCAASGFTFNTYAMNWVRQAPGKGLEWVARIRSKYNNYATYYA DSVKDRFTISRDDSKNTAYLQMNNLKTEDTAVYYCVRHGNFGNSY VSWFAYWGQGTLVTVSSGGGGSQVQLKQSGPGLVQPSQSLSITCT VSGFSLTNYGVHWVRQSPGKGLEWLGVIWSGGNTDYNTPFTSRLS INKDNSKSQVFFKMNSLQSNDTAIYYCARALTYYDYEFAYWGQGT LVTVSAASTKGPSVFPLAPSSKSTSGGTAALGCLVKDYFPEPVTV SWNSGALTSGVHTFPAVLQSSGLYSLSSVVTVPSSSLGTQTYICN VNHKPSNTKVDKKVEPKSCAAHHHHHHHH | 19 |
| PC-5 | Light Chain Sequence: N-[Peptide-2]-[Linker-4]-[anti-EGFR Fab light chain]-C | GGPCRSHIDVAKPICVGGGGSGGLSGRSDAGSPLGLAGSGGGSDIL LTQSPVILSVSPGERVSFSCRASQSIGTNIHWYQQRTNGSPRLLI KYASESISGIPSRFSGSGSGTDFTLSINSVESEDIADYYCQQNNN WPTTFGAGTKLELKRTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSFNRGEC | 20 |
| PC-5 | Heavy Chain Sequence: N-[10 G SDA]-[Peptide-4]-[Linker-4]-[anti-CD3 scFv (light chain-heavy chain)]-[anti-EGFR Fab heavy chain]-C | EVQLVESGGGLVQPGNSLRLSCAASGFTFSKFGMSWVRQAPGKGL EWVSSISGSGRDTLYADSVKGRFTISRDNAKTTLYLQMNSLRPED TAVYYCTIGGSLSVSSQGTLVTVSSGGGGSGGGGSQGQSGQGYLWG CEWNCAGITTGSSGGSGGLSGRSDAGSPLGLAGSGGGSQTVVTQE PSLTVSPGGTVTLTCRSSTGAVTTSNYANWVQQKPGQAPRGLIGG TNKRAPGTPARFSGSLLGGKAALTLSGVQPEDEAEYYCALWYSNL WVFGGGTKLTVLGGGGSGGGGSGGGGSEVQLVESGGGLVQPGGSL KLSCAASGFTFNTYAMNWVRQAPGKGLEWVARIRSKYNNYATYYA DSVKDRFTISRDDSKNTAYLQMNNLKTEDTAVYYCVRHGNFGNSY VSWFAYWGQGTLVTVSSGGGGSQVQLKQSGPGLVQPSQSLSITCT VSGFSLTNYGVHWVRQSPGKGLEWLGVIWSGGNTDYNTPFTSRLS INKDNSKSQVFFKMNSLQSNDTAIYYCARALTYYDYEFAYWGQGT | 21 |

TABLE 1-continued

Summary of Amino Acid Sequences

| Construct ID | Construct Description | Amino Acid Sequence (N to C) | SEQ ID NO: |
|---|---|---|---|
| PC-6 | N-[anti-EGFR Fab heavy chain]-C | LVTVSAASTKGPSVFPLAPSSKSTSGGTAALGCLVKDYFPEPVTV SWNSGALTSGVHTFPAVLQSSGLYSLSSVVTVPSSSLGTQTYICN VNHKPSNTKVDKKVEPKSCAAHHHHHHHH QILLTQSPVILSVSPGERVSFSCRASQSIGTNIHWYQQRTNGSPR LLIKYASESISGIPSRFSGSGSGTDFTLSINSVESEDIADYYCQQ NNNWPTTFGAGTKLELKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC | 22 |
| PC-6 | N-[anti-CD3 scFv (light chain-heavy chain)]-[anti-EGFR Fab heavy chain]-C | QTVVTQEPSLTVSPGGTVTLTCRSSTGAVTTSNYANWVQQKPGQA PRGLIGGTNKRAPGTPARFSGSLLGGKAALTLSGVQPEDEAEYYC ALWYSNLWVFGGGTKLTVLGGGGSGGGGSGGGGSEVQLVESGGGL VQPGGSLKLSCAASGFTFNTYAMNWVRQAPGKGLEWVARIRSKYN NYATYYADSVKDRFTISRDDSKNTAYLQMNNLKTEDTAVYYCVRH GNFGNSYVSWFAYWGQGLTVTVSSGGGGSQVQLKQSGPGLVQPSQ SLSITCTVSGFSLTNYGVHWVRQSPGKGLEWLGVIWSGGNTDYNT PFTSRLSINKDNSKSQVFFKMNSLQSQDTAIYYCARALTYYDYEF AYWGQGTLVTVSAASTKGPSVFPLAPSSKSTSGGTAALGCLVDKY FPEPVTVSWNSGALTSGVHTFPAVLQSSGLYSLSSVVTVPSSSLG TQTYICNVNHKPSNTKVDKKVEPKSCGGHHHHHHHGGGLNDIFE AQKIEWHE | 23 |
| PC-7 | N-[anti-EGFR Fab heavy chain]-C | DILLTQSPVILSVSPGERVSFSCRASQSIGTNIHWYQQRTNGSPR LLIJYASESISGIPSRFSGSGSGTDFTLSINSVESEDIADYYCQQ NNNWPTTFGAGTKLELKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC | 24 |
| PC-7 | N-[anti-CD3 scFv (light chain-heavy chain)]-[anti-EGFR Fab heavy chain]-C | QTVVTQEPSLTVSPGGTVTLTCRSSTGAVTTSNYANWVQQKPGQA PRGLIGGTNKRAPGTPARFSGSLLGGKAALTLSGVQPEDEAEYYC ALWYSNLWVFGGGTKLTVLGGGGSGGGGSGGGGSEVQLVESGGGL VQPGGSLKLSCAASGFTFNTYAMNWVRQAPGKGLEWVARIRSKYN NYATYYADSVKDRFTISRDDSKNTAYLQMNNLKTEDTAVYYCVRH GNFGNSYVSWFAYWGQGLTVTVSSGGGGSQVQLKQSGPGLVQPSQ SLSITCTVSGFSLTNYGVHYWVRQSPGKGLEWLGVIWSGGNTDYN TPFTSRLSINDNSKSQVFFKMNSLQSNDTAIYYCARALTYYDYEF AYWGQGLTVTVSAASTKGPSVFPLAPSSKSTSGGTAALGCLVKDY FPEPVTVSWNSGALTSGVHTFPAVLQSSGLYSLSSVVTVPSSSLG TQTYICNVNHKPSNTKVDKKVEPKSCGGHHHHHHHGGGLNDIFE AQKIEWHE | 25 |

Polypeptides or polypeptide complexes, in some embodiments, comprise a sequence set forth in Table 1. In some embodiments, the sequence comprises at least or about 70%, 80%, 85%, 90%, 91%, 92%, 93%, 94%, 95%, 96%, 97%, 98%, 99%, or 100% sequence identity to SEQ ID NOs: 1, 2, 4, 5, 7, 8, 9, 12, 13, 14, 15, 16, 17, 18, 19, 20, 21, 22, 23, 24, or 25. In some instances, the sequence comprises at least or about 95% homology to SEQ ID NOs: 1, 2, 4, 5, 7, 8, 9, 12, 13, 14, 15, 16, 17, 18, 19, 20, 21, 22, 23, 24, or 25. In some instances, the sequence comprises at least or about 97% homology to SEQ ID NOs: 1, 2, 4, 5, 7, 8, 9, 12, 13, 14, 15, 16, 17, 18, 19, 20, 21, 22, 23, 24, or 25. In some instances, the sequence comprises at least or about 99% homology to SEQ ID NOs: 1, 2, 4, 5, 7, 8, 9, 12, 13, 14, 15, 16, 17, 18, 19, 20, 21, 22, 23, 24, or 25. In some instances, the sequence comprises at least or about 100% homology to SEQ ID NOs: 1, 2, 4, 5, 7, 8, 9, 12, 13, 14, 15, 16, 17, 18, 19, 20, 21, 22, 23, 24, or 25. In some instances, the sequence comprises at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, or more than 400 amino acids of SEQ ID NOs: 1, 2, 4, 5, 7, 8, 9, 12, 13, 14, 15, 16, 17, 18, 19, 20, 21, 22, 23, 24, or 25.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Wash. D. C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Production of Polypeptides Comprising Cleavable Linkers

In some embodiments, polypeptides described herein (e.g., antibodies and its binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994, BioTechniques 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its binding is optionally generated by immunizing an animal, such as a mouse, to generate polyclonal antibodies or, more preferably, by generating monoclonal antibodies, e.g., as described by Kohler and Milstein (1975, Nature 256:495-497) or, as described by Kozbor et al. (1983, Immunology Today 4:72) or Cole et al. (1985 in Monoclonal Antibodies and Cancer Therapy, Alan R. Liss, Inc., pp. 77-96). Alternatively, a clone encoding at least the Fab portion of the antibody is optionally obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

In some embodiments, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region.

In some embodiments, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli are also optionally used (Skerra et al., 1988, Science 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody, or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., E. coli and B. subtilis) transformed with recombinant bacteriophage DNA, plasmid DNA or cosmid DNA expression vectors containing an antibody or its binding fragment coding sequences; yeast (e.g., Saccharomyces Pichia) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, Cell 11:223), hypoxanthine-guanine phosphoribosyltransferase (Szybalska &

Szybalski, 192, Proc. Natl. Acad. Sci. USA 48:202), and adenine phosphoribosyltransferase (Lowy et al., 1980, Cell 22:817) genes are employed in tk-, hgprt- or aprt-cells, respectively. Also, antimetabolite resistance are used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May 1993, TIB TECH 11(5):155-215) and hygro, which confers resistance to hygromycin (Santerre et al., 1984, Gene 30:147). Methods commonly known in the art of recombinant DNA technology which can be used are described in Ausubel et al. (eds., 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1).

In some instances, the expression levels of an antibody are increased by vector amplification (for a review, see Bebbington and Hentschel, the use of vectors based on gene amplification for the expression of cloned genes in mammalian cells in DNA cloning, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, Mol. Cell Biol. 3:257).

In some instances, any method known in the art for purification of an antibody is used, for example, by chromatography (e.g., ion exchange, affinity, particularly by affinity for the specific antigen after Protein A, and sizing column chromatography), centrifugation, differential solubility, or by any other standard technique for the purification of proteins.

Expression Vectors

In some embodiments, vectors include any suitable vectors derived from either a eukaryotic or prokaryotic sources. In some cases, vectors are obtained from bacteria (e.g. *E. coli*), insects, yeast (e.g. *Pichia pastoris*), algae, or mammalian sources. Exemplary bacterial vectors include pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Exemplary insect vectors include pFastBac1, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

In some cases, yeast vectors include Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pFLD1 *Pichi pastoris* vector, pGAPZA, B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

Exemplary algae vectors include pChlamy-4 vector or MCS vector.

Examples of mammalian vectors include transient expression vectors or stable expression vectors. Mammalian transient expression vectors may include pRK5, p3×FLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3×FLAG-CMV 7.1, pFLAG-CMV 20, p3×FLAG-Myc-CMV 24, pCMV-FLAG-MAT1, pCMV-FLAG-MAT2, pBICEP-CMV 3, or pBICEP-CMV 4. Mammalian stable expression vector may include pFLAG-CMV 3, p3×FLAG-CMV 9, p3×FLAG-CMV 13, pFLAG-Myc-CMV 21, p3×FLAG-Myc-CMV 25, pFLAG-CMV 4, p3×FLAG-CMV 10, p3×FLAG-CMV 14, pFLAG-Myc-CMV 22, p3×FLAG-Myc-CMV 26, pBICEP-CMV 1, or pBICEP-CMV 2.

In some instances, a cell-free system is a mixture of cytoplasmic and/or nuclear components from a cell and is used for in vitro nucleic acid synthesis. In some cases, a cell-free system utilizes either prokaryotic cell components or eukaryotic cell components. Sometimes, a nucleic acid synthesis is obtained in a cell-free system based on for example *Drosophila* cell, *Xenopus* egg, or HeLa cells. Exemplary cell-free systems include, but are not limited to, *E. coli* S30 Extract system, *E. coli* T7 S30 system, or PURExpress®.

Host Cells

In some embodiments, a host cell includes any suitable cell such as a naturally derived cell or a genetically modified cell. In some instances, a host cell is a production host cell. In some instances, a host cell is a eukaryotic cell. In other instances, a host cell is a prokaryotic cell. In some cases, a eukaryotic cell includes fungi (e.g., yeast cells), animal cell or plant cell. In some cases, a prokaryotic cell is a bacterial cell. Examples of bacterial cell include gram-positive bacteria or gram-negative bacteria. Sometimes the gram-negative bacteria is anaerobic, rod-shaped, or both.

In some instances, gram-positive bacteria include Actinobacteria, Firmicutes or Tenericutes. In some cases, gram-negative bacteria include Aquificae, Deinococcus-Thermus, Fibrobacteres-Chlorobi/Bacteroidetes (FCB group), Fusobacteria, Gemmatimonadetes, Nitrospirae, Planctomycetes-Verrucomicrobia/Chlamydiae (PVC group), Proteobacteria, Spirochaetes or Synergistetes. Other bacteria can be Acidobacteria, Chloroflexi, Chrysiogenetes, Cyanobacteria, Deferribacteres, Dictyoglomi, Thermodesulfobacteria or Thermotogae. A bacterial cell can be *Escherichia coli, Clostridium botulinum*, or Coli bacilli.

Exemplary prokaryotic host cells include, but are not limited to, BL21, Mach1™, DH10B™, TOP10, DH5α, DH10Bac™, OmniMax™, MegaX™, DH12STM, INV110, TOP10F', INVαF, TOP10/P3, ccdB Survival, PIR1, PIR2, Stbl2™, Stbl3™, or Stbl4™.

In some instances, animal cells include a cell from a vertebrate or from an invertebrate. In some cases, an animal cell includes a cell from a marine invertebrate, fish, insects, amphibian, reptile, or mammal. In some cases, a fungus cell includes a yeast cell, such as brewer's yeast, baker's yeast, or wine yeast.

Fungi include ascomycetes such as yeast, mold, filamentous fungi, basidiomycetes, or zygomycetes. In some instances, yeast includes Ascomycota or Basidiomycota. In some cases, Ascomycota includes Saccharomycotina (true yeasts, e.g. *Saccharomyces cerevisiae* (baker's yeast)) or Taphrinomycotina (e.g. Schizosaccharomycetes (fission yeasts)). In some cases, Basidiomycota includes Agaricomycotina (e.g. Tremellomycetes) or Pucciniomycotina (e.g. Microbotryomycetes).

Exemplary yeast or filamentous fungi include, for example, the genus: *Saccharomyces, Schizosaccharomyces, Candida, Pichia, Hansenula, Kluyveromyces, Zygosaccharomyces, Yarrowia, Trichosporon, Rhodosporidi, Aspergillus, Fusarium,* or *Trichoderma*. Exemplary yeast or filamentous fungi include, for example, the species: *Saccharomyces cerevisiae, Schizosaccharomyces pombe, Candida utilis, Candida boidini, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Pichia metanolica, Pichia angusta, Pichia pastoris, Pichia anomala, Hansenula polymorpha, Kluyveromyces lactis, Zygosaccharomyces rouxii, Yarrowia lipolytica, Trichosporon pullulans, Rhodosporidium toru-Aspergillus niger, Aspergillus nidulans, Aspergillus awamori, Aspergillus oryzae, Trichoderma reesei, Yarrowia lipolytica, Brettanomyces bruxellensis, Candida stellata, Schizosaccharomyces pombe, Torulaspora delbrueckii, Zygosaccharomyces bailii, Cryptococcus neoformans, Cryptococcus gattii,* or *Saccharomyces boulardii*.

Exemplary yeast host cells include, but are not limited to, *Pichia pastoris* yeast strains such as GS115, KM71H, SMD1168, SMD1168H, and X-33; and *Saccharomyces cerevisiae* yeast strain such as INVSc1.

In some instances, additional animal cells include cells obtained from a mollusk, arthropod, annelid or sponge. In some cases, an additional animal cell is a mammalian cell, e.g., from a primate, ape, equine, bovine, porcine, canine, feline or rodent. In some cases, a rodent includes mouse, rat, hamster, gerbil, hamster, chinchilla, fancy rat, or guinea pig.

Exemplary mammalian host cells include, but are not limited to, 293A cell line, 293FT cell line, 293F cells, 293 H cells, CHO DG44 cells, CHO-S cells, CHO-K1 cells, FUT8 KO CHOK1, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some instances, a mammalian host cell is a stable cell line, or a cell line that has incorporated a genetic material of interest into its own genome and has the capability to express the product of the genetic material after many generations of cell division. In some cases, a mammalian host cell is a transient cell line, or a cell line that has not incorporated a genetic material of interest into its own genome and does not have the capability to express the product of the genetic material after many generations of cell division.

Exemplary insect host cells include, but are not limited to, *Drosophila* S2 cells, Sf9 cells, Sf21 cells, High Five™ cells, and expresSF+® cells.

In some instances, plant cells include a cell from algae. Exemplary insect cell lines include, but are not limited to, strains from *Chlamydomonas reinhardtii* 137c, or *Synechococcus elongatus* PPC 7942.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific antibody comprising a first antigen-binding site that specifically binds to CD3 and a second antigen-binding site that specifically binds to a tumor antigen.

The label or package insert indicates that the composition is used for treating the condition of choice. Moreover, the article of manufacture may comprise (a) a first container with a composition contained therein, wherein the composition comprises the bispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Methods of Treatment

In some embodiments, the isolated polypeptide comprising the cleavable linkers described herein are used in a method of treating cancer. In some embodiments, the cancer has cells that express EGFR. In some embodiments, the polypeptides or polypeptide complexes described herein are used in a method of treating colorectal cancer (CRC), squamous cell carcinoma of the head and Neck (SCCHN), non-small cell lung cancer (NSCLC), prostate cancer, breast cancer, colon/rectum cancer, head and neck cancer, esophagostric cancer, liver cancer, glioblastoma, cervical cancer, ovarian cancer, bladder cancer, kidney cancer, or pancreatic cancer. In some embodiments, the polypeptides or polypeptide complexes described herein are used in a method of treating subjects who are resistant to EGFR inhibitor treatment. In some embodiments, the polypeptides or polypeptide complexes described herein are used in a method of treating subjects who harbor KRAS mutations. In some embodiments, the polypeptides or polypeptide complexes described herein are used in a method of treating subjects who are resistant to EGFR inhibitor treatment and harbor KRAS mutations.

While preferred embodiments of the present invention have been shown and described herein, it will be obvious to those skilled in the art that such embodiments are provided

EMBODIMENTS

Embodiment 1 comprises an isolated polypeptide comprising a cleavable linker according to the amino acid sequence of SEQ ID NO: 1 (LSGRSDAG).

Embodiment 2 comprises an isolated polypeptide of embodiment 1, wherein the cleavable linker comprises the amino acid sequence of SEQ ID NO: 3 (ISSGLLSGRSDAG).

Embodiment 3 comprises an isolated polypeptide of any one of embodiments 1-2, wherein the cleavable linker comprises the amino acid sequence of SEQ ID NO: 26 (AGLLAPPGGLSGRSDAG).

Embodiment 4 comprises an isolated polypeptide of any one of embodiments 1-3, wherein the cleavable linker comprises the amino acid sequence of SEQ ID NO: 4 (AAGLLAPPGGLSGRSDAG).

Embodiment 5 comprises an isolated polypeptide of any one of embodiments 1-4, wherein the cleavable linker comprises the amino acid sequence of SEQ ID NO: 5 (SPLGLSGRSDAG).

Embodiment 6 comprises an isolated polypeptide of any one of embodiments 1-5, wherein the cleavable linker comprises the amino acid sequence of SEQ ID NO: 6 (LSGRSDAGSPLGLAG).

Embodiment 7 comprises an isolated polypeptide of any one of embodiments 1-6, wherein the cleavable linker is cleavable by a protease.

Embodiment 8 comprises an isolated polypeptide of embodiment 7, wherein the protease comprises a tumor specific protease.

Embodiment 9 comprises an isolated polypeptide of any one of embodiments 7-8, wherein the protease comprises a matrix metalloprotease (MMP) or a serine protease.

Embodiment 10 comprises an isolated polypeptide of embodiment 9, wherein the matrix metalloprotease comprises MMP2, MMP7, MMP9, MMP13, or MMP14.

Embodiment 11 comprises an isolated polypeptide of embodiment 9, wherein the serine protease comprises matriptase, urokinase, or hepsin.

Embodiment 12 comprises an isolated polypeptide of any one of embodiments 1-11, wherein the isolated polypeptide further comprises an antigen binding domain that binds to a target antigen.

Embodiment 13 comprises an isolated polypeptide of embodiment 12, wherein the antigen binding domain is C-terminal to the cleavable linker.

Embodiment 14 comprises an isolated polypeptide of any one of embodiments 1-11, wherein the isolated polypeptide further comprises a cytokine or cytokine fragment that binds to a cytokine receptor.

Embodiment 15 comprises an isolated polypeptide of embodiment 14, wherein the cytokine or cytokine fragment is C-terminal to the cleavable linker.

Embodiment 16 comprises an isolated polypeptide of any one of embodiments 1-15, wherein the cleavable linker connects a peptide to an antigen binding domain that binds to a target antigen or to a cytokine or cytokine fragment that binds to a cytokine receptor in a configuration according to Formula I: $A_1$-$L_1$-$P_1$ wherein A comprises the antigen binding domain that binds to the target antigen or the cytokine or cytokine fragment that binds to the cytokine receptor; $L_1$ comprises the cleavable linker; $P_1$ comprises a peptide that impairs binding of the antigen binding domain to the target antigen or impairs binding of the cytokine to the cytokine receptor.

Embodiment 17 comprises an isolated polypeptide of embodiment 16, wherein $P_1$ is connected N-terminal to the cleavable linker and $A_1$ is connected C-terminal to the cleavable linker.

Embodiment 18 comprises an isolated polypeptide of embodiment 16, wherein $P_1$ is connected C-terminal to the cleavable linker and $A_1$ is connected N-terminal to the cleavable linker.

Embodiment 19 comprises an isolated polypeptide of any one of embodiments 16-18, wherein $P_1$ is bound to $A_1$ through ionic interactions, electrostatic interactions, hydrophobic interactions, $P_1$-stacking interactions, and H-bonding interactions, or a combination thereof.

Embodiment 20 comprises an isolated polypeptide of any one of embodiments 16-19, wherein $P_1$ has less than 70% sequence homology to the target antigen or the cytokine receptor.

Embodiment 21 comprises an isolated polypeptide of any one of embodiments 16-20, wherein $P_1$ comprises a peptide sequence of at least 10 amino acids in length.

Embodiment 22 comprises an isolated polypeptide of any one of embodiments 16-21, wherein $P_1$ comprises a peptide sequence of at least 10 amino acids in length and no more than 20 amino acids in length.

Embodiment 23 comprises an isolated polypeptide of any one of embodiments 16-22, wherein $P_1$ comprises a peptide sequence of at least 16 amino acids in length.

Embodiment 24 comprises an isolated polypeptide of any one of embodiments 16-23, wherein $P_1$ comprises a peptide sequence of no more than 40 amino acids in length.

Embodiment 25 comprises an isolated polypeptide of any one of embodiments 16-24, wherein $P_1$ comprises a cyclic peptide or a linear peptide.

Embodiment 26 comprises an isolated polypeptide of any one of embodiments 16-25, wherein $P_1$ comprises a cyclic peptide.

Embodiment 27 comprises an isolated polypeptide of any one of embodiments 16-26, wherein $P_1$ is further linked to a half-life extending moiety.

Embodiment 28 comprises an isolated polypeptide of embodiment 27, wherein the half-life extending moiety is a single-domain antibody.

Embodiment 29 comprises an isolated polypeptide of embodiment 28, wherein the single domain antibody comprises 10G.

Embodiment 30 comprises an isolated polypeptide of any one of embodiments 16-29, wherein $A_1$ comprises an antibody, a single chain variable fragment (scFv), a heavy chain variable domain (VH domain), a light chain variable domain (VL domain), a variable domain (VHH) of a camelid derived single domain antibody, a Fab, a Fab', a Fab light chain polypeptide, or a Fab heavy chain polypeptide.

Embodiment 31 comprises an isolated polypeptide of any one of embodiments 16-30, wherein the target antigen comprises a tumor antigen.

Embodiment 32 comprises an isolated polypeptide of any one of embodiments 30-31, wherein $A_1$ comprises the Fab light chain polypeptide or the Fab heavy chain polypeptide.

Embodiment 33 comprises an isolated polypeptide of any one of embodiments 16-32, wherein $A_1$ comprises an epidermal growth factor receptor (EGFR) binding domain.

Embodiment 34 comprises an isolated polypeptide of any one of embodiments 16-30, wherein the target antigen comprises an effector cell antigen.

Embodiment 35 comprises an isolated polypeptide of embodiment 34, wherein A, comprises the scFv.

Embodiment 36 comprises an isolated polypeptide of embodiment 35, wherein the scFv comprises an an anti-CD3e single chain variable fragment.

Embodiment 37 comprises an isolated polypeptide of any one of embodiments 16-29, wherein $A_1$ comprises the cytokine.

Embodiment 38 comprises an isolated polypeptide of embodiment 37, wherein the cytokine or cytokine fragment is a wild-type cytokine.

Embodiment 39 comprises an isolated polypeptide of embodiment 37, wherein the cytokine or cytokine fragment is a mutein of the cytokine.

Embodiment 40 comprises an isolated polypeptide of any one of embodiments 37-39, wherein the cytokine receptor is an interferon receptor or an interleukin receptor.

Embodiment 41 comprises an isolated polypeptide of any one of embodiments 37-40, wherein the cytokine receptor comprises an interferon receptor, GM-CSF receptor, IL-2 receptor, IL-4 receptor, IL-6 receptor, IL-7 receptor, IL-10 receptor, IL-12 receptor, IL-15 receptor, IL-21 receptor, or TGF-β receptor.

Embodiment 42 comprises an isolated polypeptide of any one of embodiments 37-41, wherein the cytokine or cytokine fragment comprises an interferon, GM-CSF, IL-2, IL-7, IL-12, IL-15, or IL-21.

Embodiment 43 comprises an isolated polypeptide of any one of embodiments 37-42, wherein the cytokine or cytokine fragment comprises an IL-2, IL-12, IL-6, IL-4, IL-10, or TGFβ.

Embodiment 44 comprises an isolated polypeptide of any one of embodiments 1-43, wherein the isolated polypeptide is complexed with a second isolated polypeptide comprising a second antigen binding domain or a second cytokine or second cytokine fragment.

Embodiment 45 comprises an isolated polypeptide of embodiment 44, wherein the second isolated polypeptide is in a configuration according to Formula II: $A_2$-$L_2$-$P_2$ wherein $A_2$ comprises the second antigen binding domain or the second cytokine; $L_2$ comprises a second cleavable linker; $P_2$ comprises a second peptide that impairs binding of the second antigen binding domain to a second target antigen or impairs binding of the second cytokine or second cytokine fragment to a second cytokine receptor.

Embodiment 46 comprises an isolated polypeptide of embodiment 45, wherein the second cleavable linker comprises the amino acid sequence of SEQ ID NO: 1 (LSGRSDAG).

Embodiment 47 comprises an isolated polypeptide of any one of embodiments 45-46, wherein the second cleavable linker comprises the amino acid sequence of SEQ ID NO: 3 (ISSGLLSGRSDAG).

Embodiment 48 comprises an isolated polypeptide of any one of embodiments 45-47, wherein the second cleavable linker comprises the amino acid sequence of SEQ ID NO: 26 (AGLLAPPGGLSGRSDAG).

Embodiment 49 comprises an isolated polypeptide of any one of embodiments 45-48, wherein the second cleavable linker comprises the amino acid sequence of SEQ ID NO: 4 (AAGLLAPPGGLSGRSDAG).

Embodiment 50 comprises an isolated polypeptide of any one of embodiments 45-49, wherein the second cleavable linker comprises the amino acid sequence of SEQ ID NO: 5 (SPLGLSGRSDAG).

Embodiment 51 comprises an isolated polypeptide of any one of embodiments 45-50, wherein the second cleavable linker comprises the amino acid sequence of SEQ ID NO: 6 (LSGRSDAGSPLGLAG).

Embodiment 52 comprises an isolated polypeptide of any one of embodiments 45-51, wherein $P_2$ is connected N-terminal to the second cleavable linker and $A_2$ is connected C-terminal to the second cleavable linker.

Embodiment 53 comprises an isolated polypeptide of any one of embodiments 45-51, wherein $P_2$ is connected C-terminal to the second cleavable linker and $A_2$ is connected N-terminal to the second cleavable linker.

Embodiment 54 comprises an isolated polypeptide of any one of embodiments 45-53, wherein $P_2$ is bound to $A_2$ through ionic interactions, electrostatic interactions, hydrophobic interactions, $P_1$-stacking interactions, and H-bonding interactions, or a combination thereof.

Embodiment 55 comprises an isolated polypeptide of any one of embodiments 45-54, wherein $P_2$ has less than 70% sequence homology to the second target antigen or the second cytokine receptor.

Embodiment 56 comprises an isolated polypeptide of any one of embodiments 45-55, wherein $P_2$ comprises a peptide sequence of at least 10 amino acids in length.

Embodiment 57 comprises an isolated polypeptide of any one of embodiments 45-56, wherein $P_2$ comprises a peptide sequence of at least 10 amino acids in length and no more than 20 amino acids in length.

Embodiment 58 comprises an isolated polypeptide of any one of embodiments 45-57, wherein $P_2$ comprises a peptide sequence of at least 16 amino acids in length.

Embodiment 59 comprises an isolated polypeptide of any one of embodiments 45-56, wherein $P_2$ comprises a peptide sequence of no more than 40 amino acids in length.

Embodiment 60 comprises an isolated polypeptide of any one of embodiments 45-59, wherein $P_2$ comprises a cyclic peptide or a linear peptide.

Embodiment 61 comprises an isolated polypeptide of any one of embodiments 45-60, wherein $P_2$ comprises a cyclic peptide.

Embodiment 62 comprises an isolated polypeptide of any one of embodiments 45-61, wherein $A_2$ comprises an antibody, a single chain variable fragment (scFv), a heavy chain variable domain (VH domain), a light chain variable domain (VL domain), a variable domain (VHH) of a camelid derived single domain antibody, a Fab, a Fab', a Fab light chain polypeptide, or a Fab heavy chain polypeptide.

Embodiment 63 comprises an isolated polypeptide of any one of embodiments 45-62, wherein the second target antigen comprises a tumor antigen.

Embodiment 64 comprises an isolated polypeptide of embodiment 62, wherein $A_2$ comprises the Fab light chain polypeptide or the Fab heavy chain polypeptide.

Embodiment 65 comprises an isolated polypeptide of any one of embodiments 45-64, wherein $A_2$ comprises an epidermal growth factor receptor (EGFR) binding domain.

Embodiment 66 comprises an isolated polypeptide of any one of embodiments 45-62, wherein the second target antigen comprises an effector cell antigen.

Embodiment 67 comprises an isolated polypeptide of embodiment 62, wherein $A_2$ comprises the scFv.

Embodiment 68 comprises an isolated polypeptide of any one of embodiments 66-67, wherein the scFv comprises an anti-CD3e single chain variable fragment.

Embodiment 69 comprises an isolated polypeptide of any one of embodiments 45-61, wherein $A_2$ comprises the second cytokine.

Embodiment 70 comprises an isolated polypeptide of embodiment 69, wherein the second cytokine or second cytokine fragment is a wild-type cytokine.

Embodiment 71 comprises an isolated polypeptide of embodiment 69, wherein the second cytokine or second cytokine fragment is a mutein of the cytokine.

Embodiment 72 comprises an isolated polypeptide of any one of embodiments 69-71, wherein the second cytokine receptor is an interferon receptor or an interleukin receptor.

Embodiment 73 comprises an isolated polypeptide of any one of embodiments 69-72, wherein the second cytokine receptor comprises an interferon receptor, GM-CSF receptor, IL-2 receptor, IL-4 receptor, IL-6 receptor, IL-7 receptor, IL-10 receptor, IL-12 receptor, IL-15 receptor, IL-21 receptor, or TGF-β receptor.

Embodiment 74 comprises an isolated polypeptide of any one of embodiments 69-73, wherein the second cytokine or second cytokine fragment comprises an interferon, GM-CSF, IL-2, IL-7, IL-12, IL-15, or IL-21.

Embodiment 75 comprises an isolated polypeptide of any one of embodiments 69-74, wherein the second cytokine or second cytokine fragment comprises an IL-2, IL-12, IL-6, IL-4, IL-10, or TGFβ.

Embodiment 76 comprises a pharmaceutical composition comprising: the isolated polypeptide comprising a cleavable linker of any one of the above embodiments; and a pharmaceutically acceptable excipient.

Embodiment 77 comprises an isolated recombinant nucleic acid molecule encoding the isolated polypeptide comprising a cleavable linker of any one of the above embodiments.

Embodiment 78 comprises a vector comprising the isolated recombinant nucleic acid molecule according to Embodiment 77.

Embodiment 79 comprises a method of producing an isolated polypeptide comprising a cleavable linker according to any of the above embodiments comprising culturing a cell under conditions that lead to expression of the polypeptide, wherein the cell comprises the vector of embodiment 78.

Embodiment 80 comprises a method of manufacturing an isolated polypeptide comprising a cleavable linker, the method comprising: (a) culturing a cell comprising the recombinant nucleic acid molecule of embodiment 77 under conditions that lead to expression of the polypeptide, and (b) isolating the polypeptide.

EXAMPLES

Example 1. Proteolysis Rates and Serum Stability

The polypeptide complexes were evaluated for tumor and serum protease activity.

Briefly, polypeptide complexes PC-1, PC-2, PC-3, PC-4, and PC-5 were generated comprising peptide masks genetically fused to the polypeptide complexes using cleavable linkers recognized by various tumor proteases. The polypeptide complexes were exposed to various tumor proteases. Cleavage rate was determined when the polypeptide complexes were exposed to MMP2, MMP7, MMP9, MMP13, MMP14, uPa, MTSP1, and Hepsin. The data for apparent cleavage rate and relative serum stability are seen in Tables 2-4.

TABLE 2

| Apparent Cleavage Rate Comparisons | | | | | |
|---|---|---|---|---|---|
| Tumor Proteases | PC-1 | PC-2 | PC-3 | PC-4 | PC-5 |
| MMP2 | $10^4 < r < 10^5$ | $10^4 < r < 10^5$ | $>10^5$ | $>10^5$ | $>10^5$ |
| MMP7 | $\leq 25 \times 10^3$ | $\leq 2.5 \times 10^3$ | $10^4 < r < 10^5$ | $>10^5$ | $>10^5$ |
| MMP9 | $\leq 25 \times 10^3$ | $\leq 2.5 \times 10^3$ | $10^4 < r < 10^5$ | $>10^5$ | $>10^5$ |
| MMP13 | $10^4 < r < 10^5$ | $10^4 < r < 10^5$ | $>10^5$ | $>10^5$ | $>10^5$ |
| MMP14 | $10^4 < r < 10^5$ | $10^4 < r < 10^5$ | $10^4 < r < 10^5$ | $10^4 < r < 10^5$ | $10^4 < r < 10^5$ |
| uPa | $2.5 \times 10^3 < r < 10^4$ | $2.5 \times 10^3 < r < 10^4$ | $2.5 \times 10^3 < r < 10^4$ | $2.5 \times 10^3 < r < 10^4$ | $2.5 \times 10^3 < r < 10^4$ |
| MTSP1 | $2.5 \times 10^3 < r < 10^4$ | $2.5 \times 10^3 < r < 10^4$ | $10^4 < r < 10^5$ | $10^4 < r < 10^5$ | $10^4 < r < 10^5$ |
| Hepsin | $>10^5$ | $>10^5$ | $10^4 < r < 10^5$ | $10^4 < r < 10^5$ | $10^4 < r < 10^5$ |

TABLE 3

Apparent Cleavage Rate Constants
Apparent Cleavage Rate Constants ($M^{-1}$ $s^{-1}$) (EGFR side)

| Tumor Protease | PC-1 | PC-2 | PC-3 | PC-4 | PC-5 |
|---|---|---|---|---|---|
| MMP2 | 1.99E+04 | 2.47E+04 | 3.63E+05 | 3.29E+05 | 3.48E+05 |
| MMP7 | 1.50E+02 | 1.57E+02 | 1.34E+04 | 1.76E+05 | 9.15E+04 |
| MMP9 | 2.35E+03 | 5.00E+01 | 4.10E+04 | 2.36E+05 | 2.82E+05 |
| MMP13 | 1.89E+04 | 1.20E+04 | 1.56E+05 | 2.75E+05 | 3.80E+05 |
| MMP14 | 1.01E+04 | 1.07E+04 | 2.78E+04 | 1.42E+04 | 1.95E+04 |
| uPa | 8.39E+03 | 4.32E+03 | 3.41E+03 | 4.03E+03 | 5.88E+03 |
| MTSP1 | 9.96E+03 | 8.63E+03 | 3.83E+04 | 3.92E+04 | 5.65E+04 |
| Hepsin | 2.53E+05 | 2.53E+05 | 7.00E+04 | 4.26E+04 | 8.28E+04 |

TABLE 4

Relative Serum Stability
Relative serum stability (% cleavage per day) (EGFR side/CD3e side)

| Serum | PC-1 | PC-2 | PC-3 | PC-4 | PC-5 |
|---|---|---|---|---|---|
| Human | 0.51%/ 0.56% | 0.52%/ 0.65% | 0.44%/0.63% | 0.44%/0.82% | 0.72%/0.71% |

The data shows that serum proteolytic activity is greater than blood. The data also shows the cleavable linker sequences have increased rates of proteolysis while retaining stability in human serum.

Example 2. Confirmation of Comparable Masking with Cleavable Linkers

The polypeptide complexes were evaluated for EGFR and CDR binding.

Figure 1B:
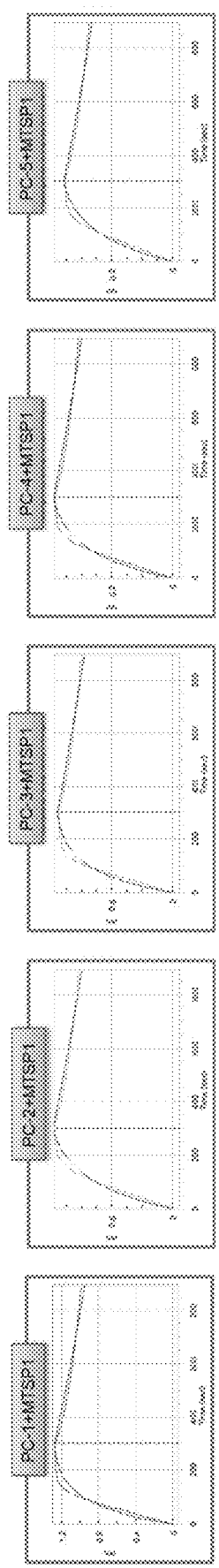

Briefly, the binding of polypeptide complexes PC-1, PC-2, PC-3, PC-4, and PC-5 comprising EGFR masking was determined. As seen in FIG. 1A, EGFR masking blocks binding for the various polypeptide complexes. Following cleavage by the tumor protease MTSP1, the polypeptide complexes are able to bind (FIG. 1B).

Details of the EGFR binding shifts are seen in Tables 5-8.

TABLE 5

| Step | Time | PH |
|---|---|---|
| Baseline: Octet buffer | 60 sec | pH 7.4 |
| Load: 30 nM EGFR-biotin (2.169 ug/mL) | 300 sec | pH 7.4 |
| Biocytin quench (100 uM) | 300 sec | pH 7.4 |
| Baseline: Octet buffer | 90 sec | pH 7.4 |

TABLE 5-continued

| Step | Time | PH |
|---|---|---|
| Association: | | |
| 25 nM PC-2 | 300 sec | pH 7.4 |
| 25 nM PC-3 | | |
| 25 nM PC-4 | | |
| 25 nM PC-5 | | |
| 25 nM PC-2 + MTSP1 | | |
| 25 nM PC-3 + MTSP1 | | |
| 25 nM PC-4 + MTSP1 | | |
| 25 nM PC-5 + MTSP1 | | |
| Dissociation: Octet buffer | 600 sec | pH 7.4 |

TABLE 6

| Sample ID | Loading Sample ID | Conc. (nM) | KD (M) | KD Error | kon (1/Ms) | kdis (1/s) | Full $R^2$ | Full $X^2$ | Response |
|---|---|---|---|---|---|---|---|---|---|
| PC-2 | EGFR | 25 | | | No significant binding | | | | |
| PC-3 | EGFR | 25 | | | No significant binding | | | | |
| PC-4 | EGFR | 25 | | | No significant binding | | | | |
| PC-5 | EGFR | 25 | | | No significant binding | | | | |
| PC-2 + MTSP1 | EGFR | 25 | 1.34E−09 | 2.87E−11 | 3.48E+05 | 4.66E−04 | 0.9735 | 2.3843 | 1.5573 |
| PC-3 + MTSP1 | EGFR | 25 | 9.46E−10 | 1.99E−11 | 4.72E+05 | 4.46E−04 | 0.9684 | 2.3105 | 1.5016 |
| PC-4 + MTSP1 | EGFR | 25 | 1.19E−09 | 2.56E−11 | 3.82E+05 | 4.54E−04 | 0.9715 | 2.45 | 1.553 |
| PC-5 + MTSP1 | EGFR | 25 | 1.45E−09 | 2.98E−11 | 3.50E+05 | 5.07E−04 | 0.9728 | 1.9973 | 1.4156 |

TABLE 7

| Step | Time | pH |
|---|---|---|
| Baseline: Octet buffer | 60 sec | pH 7.4 |
| Load: 30 nM EGFR-biotin (2.169 ug/mL) | 300 sec | pH 7.4 |
| Biocytin quench (100 uM) | 300 sec | pH 7.4 |
| Baseline: 5% human serum | 300 sec | pH 7.4 |
| Association: | | |
| 30nM PC-1, | 300 sec | pH 7.4 |
| 30nM PC-1 + MTSP1 | | |
| 30nM PC-6, | | |
| buffer | | |
| Dissociation: 5% human serum | 600 sec | pH 7.4 |

TABLE 8

| Sample ID | Loading Sample ID | Conc. (nM) | KD (M) | KD Error | kon (1/Ms) | kdis (1/s) | Full $R^2$ | Full $X^2$ | Response |
|---|---|---|---|---|---|---|---|---|---|
| PC-1 | EGFR-biotin | 50 | | | No significant binding | | | | |
| PC-1 + MTSP1 | EGFR-biotin | 50 | 1.91E−09 | 3.85E−11 | 2.60E+05 | 4.98E−04 | 0.965 | 1.7318 | 1.2733 |
| PC-6 | EGFR-biotin | 50 | 1.77E−09 | 3.19E−11 | 4.93E+05 | 8.72E−04 | 0.9535 | 1.4956 | 1.0938 |
| buffer | EGFR-biotin | 50 | <1.0E−12 | 6.00E−09 | 1.29E+04 | <1.0E−07 | 0.5559 | 0.1511 | 0.0151 |

Figure 2A:
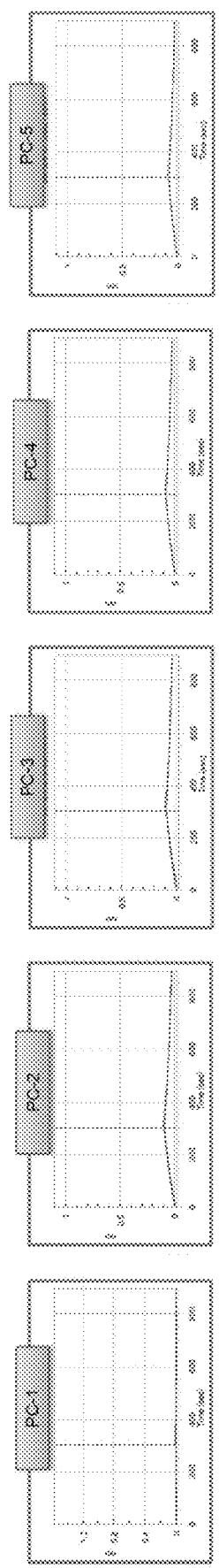
FIGS. 2A-2B illustrate of polypeptide complexes PC-1, PC-2, PC-3, PC-4, and PC-5 comprising CD3e masking (FIG. 2A) and followed by cleavage by the tumor protease MTSP1 (FIG. 2B).
Figure 2B:
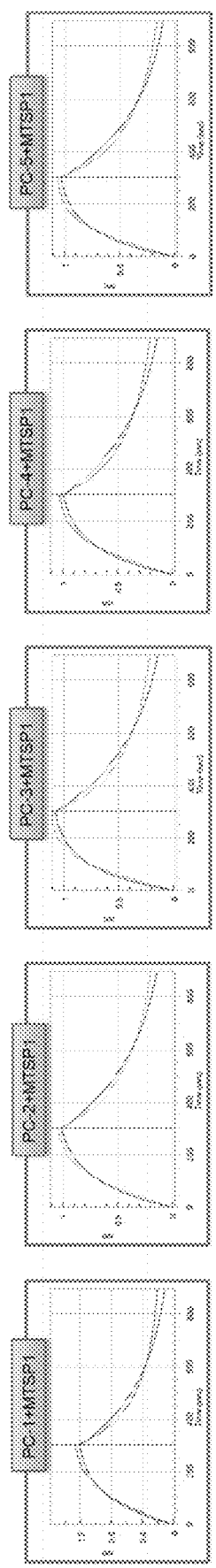

The polypeptide complexes were also evaluated for CD3ε binding. Briefly, the binding of the polypeptide complexes PC-1, PC-2, PC-3, PC-4, and PC-5 comprising CD3ε masking was determined. As seen in FIG. 2A, the masks block binding for the various polypeptide complexes. Following cleavage by the tumor protease MTSP1, the polypeptide complexes are able to bind (FIG. 2B).

Details of the CD3ε binding shifts are seen in Tables 9-12.

TABLE 9

| Step | Time | pH |
|---|---|---|
| Baseline: Octet buffer | 60 sec | pH 7.4 |
| Load: 30 nM CD3e-biotin (0.465 ug/mL) | 300 sec | pH 7.4 |

TABLE 9-continued

| Step | Time | pH |
|---|---|---|
| Biocytin quench (100 uM) | 300 sec | pH 7.4 |
| Baseline: Octet buffer | 90 sec | pH 7.4 |
| Association: | | |
| 25nM PC-2 | 300 sec | pH 7.4 |
| 25nM PC-3 | | |
| 25nM PC-4 | | |
| 25nM PC-5 | | |
| 25nM PC-2 + MTSP1 | | |
| 25nM PC-3 + MTSP1 | | |
| 25nM PC-4 + MTSP1 | | |
| 25nM PC-5 + MTSP1 | | |
| Dissociation: Octet buffer | 600 sec | pH 7.4 |

TABLE 10

| Sample ID | Loading Sample ID | Conc. (nM) | KD (M) | KD Error | kon (1/Ms) | kdis (1/s) | Full $R^2$ | Full $X^2$ | Response |
|---|---|---|---|---|---|---|---|---|---|
| PC-2 | CD3e | 25 | No significant binding | | | | | | |
| PC-3 | CD3e | 25 | No significant binding | | | | | | |
| PC-4 | CD3e | 25 | No significant binding | | | | | | |
| PC-5 | CD3e | 25 | No significant binding | | | | | | |
| PC-2 + MTSP1 | CD3e | 25 | 1.41E−08 | 3.66E−10 | 2.37E+05 | 3.33E−03 | 0.9829 | 1.2588 | 1.0342 |
| PC-3 + MTSP1 | CD3e | 25 | 1.00E−08 | 2.60E−10 | 3.37E+05 | 3.37E−03 | 0.976 | 2.078 | 1.1036 |
| PC-4 + MTSP1 | CD3e | 25 | 1.19E−08 | 3.14E−10 | 2.78E+05 | 3.30E−03 | 0.9786 | 1.5272 | 1.0227 |
| PC-5 + MTSP1 | CD3e | 25 | 1.32E−08 | 3.33E−10 | 2.91E+05 | 3.84E−03 | 0.9832 | 1.452 | 1.0526 |

TABLE 11

| Step | Time | pH |
|---|---|---|
| Baseline: Octet buffer | 60 sec | pH 7.4 |
| Load: 30 nM CD3e-biotin (0.46 ug/mL) | 300 sec | pH 7.4 |
| Biocytin quench (100 uM) | 300 sec | pH 7.4 |
| Baseline: 5% human serum | 300 sec | pH 7.4 |
| Association: | | |
| 30 nM PC-1, | 300 sec | pH 7.4 |
| 30 nM PC-1 + MTSP1 | | |
| 30 nM PC-6, | | |
| buffer | | |
| Dissociation: 5% human serum | 600 sec | pH 7.4 |

TABLE 12

| Sample ID | Loading Sample ID | Conc. (nM) | KD (M) | KD Error | kon (1/Ms) | kdis (1/s) | Full $R^2$ | Full $X^2$ | Response |
|---|---|---|---|---|---|---|---|---|---|
| PC-1 | CD3e-biotin | 50 | No significant binding | | | | | | |
| PC-1 + MTSP1 | CD3e-biotin | 50 | 3.15E−08 | 1.01E−09 | 1.25E+05 | 3.95E−03 | 0.9774 | 2.6058 | 1.2556 |
| PC-6 | CD3e-biotin | 50 | 2.26E−08 | 6.81E−10 | 1.33E+05 | 3.02E−03 | 0.9702 | 4.4245 | 1.5652 |
| buffer | CD3e-biotin | 50 | No significant binding | | | | | | |

Figure 3A:
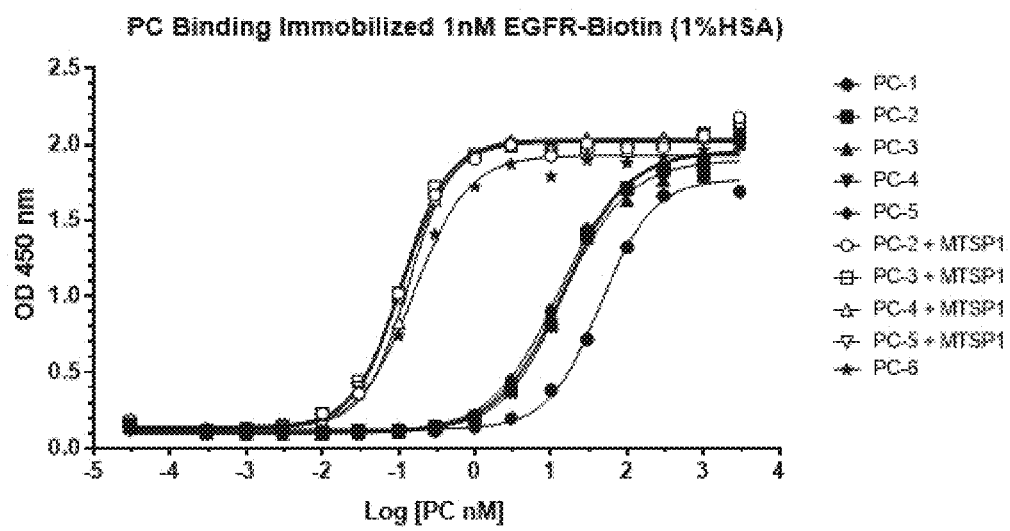
FIGS. 3A-3B illustrate binding of polypeptide complexes PC-2, PC-3, PC-4, PC-5, PC-1, and PC-6 to EGFR-biotin (FIG. 3A) and CD3ε-biotin (FIG. 3B) measured by ELISA.
Figure 3B:
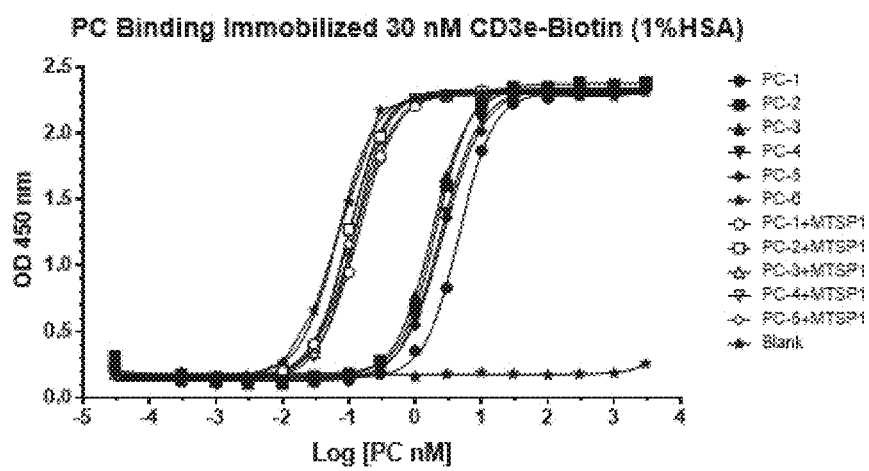
Figure 4A:
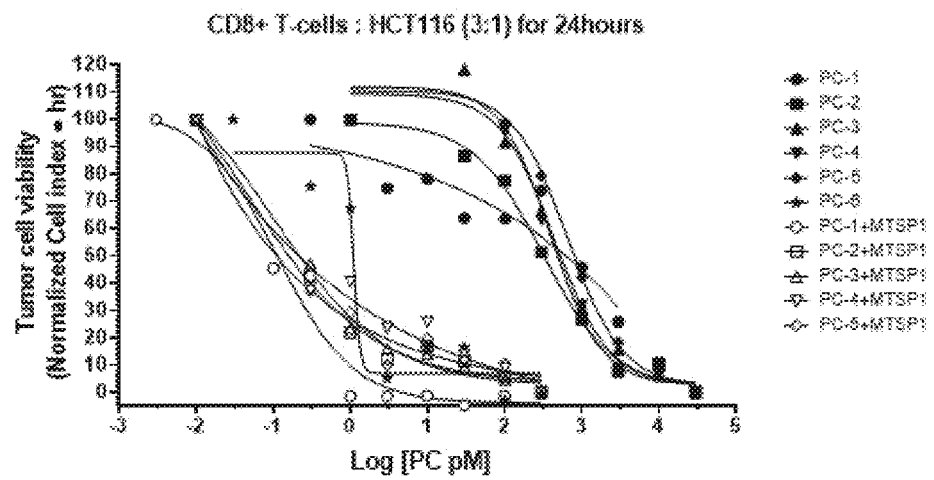
FIGS. 4A-4E illustrate cytotoxicity against tumor target cells HCT116 for polypeptide complexes PC-2, PC-3, PC-4, PC-5, PC-1, and PC-6.
Figure 4B:
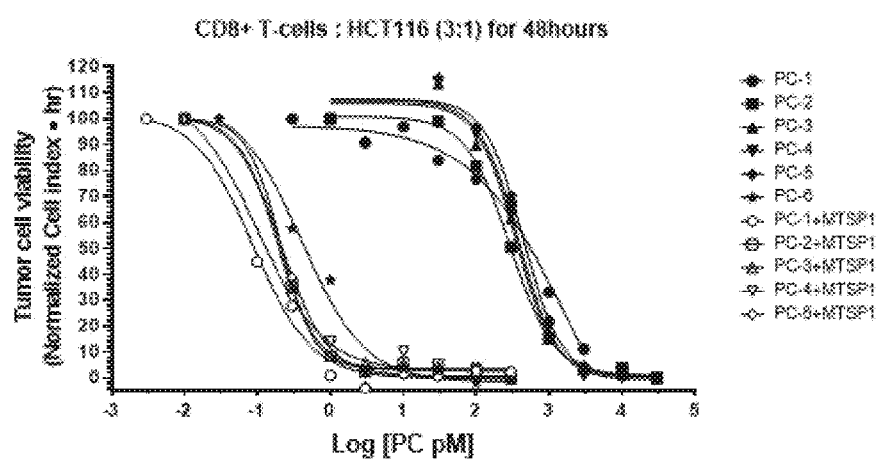
Figure 4C:
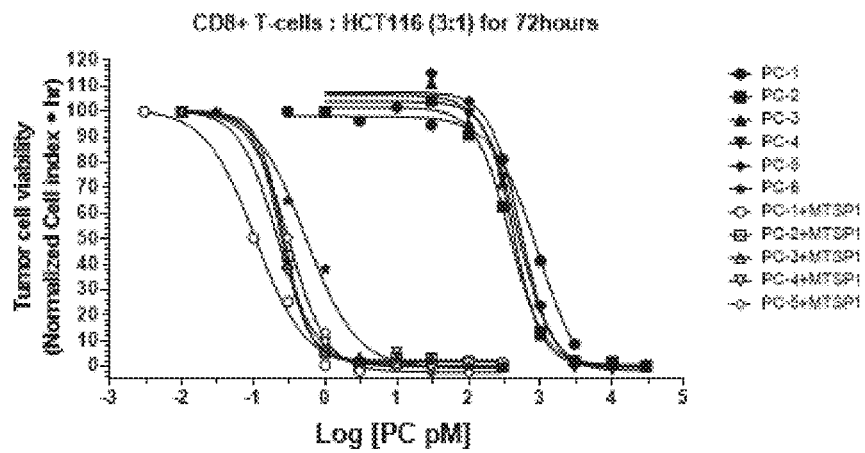
Figure 4D:
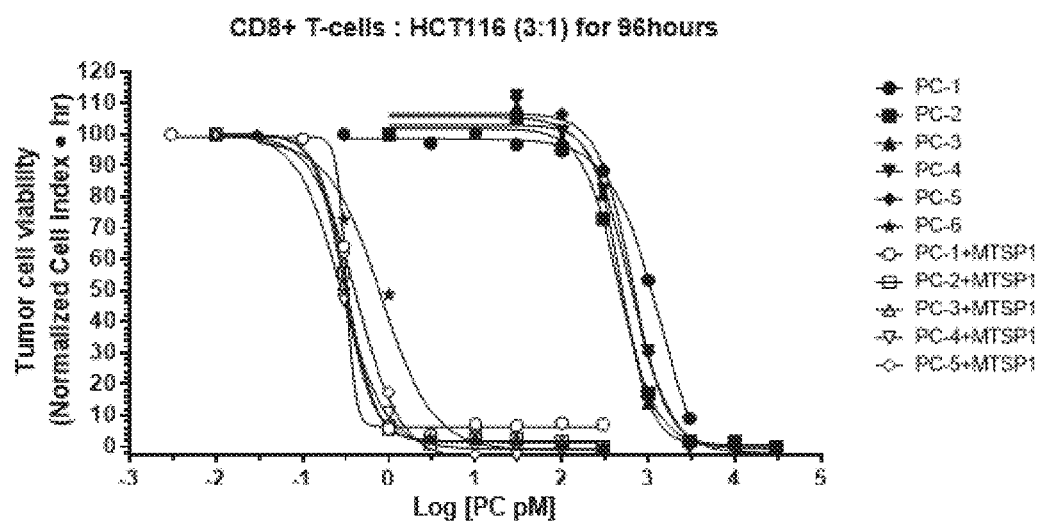
Figure 4E:
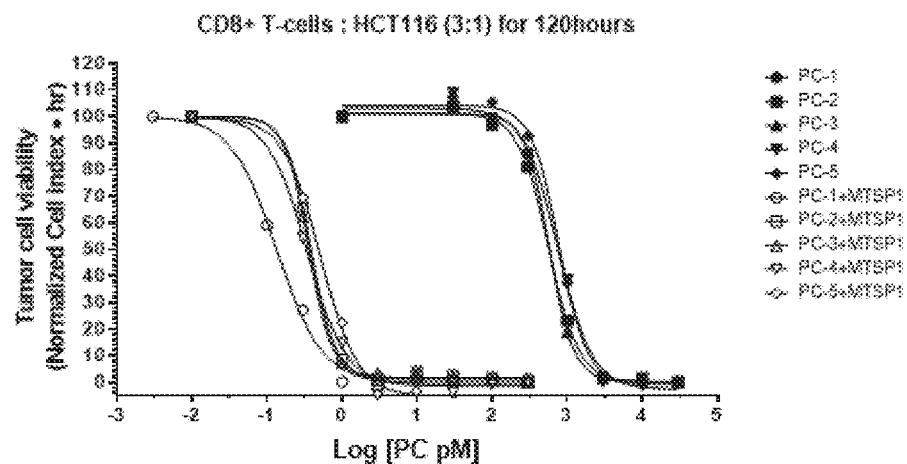
Figure 5A:
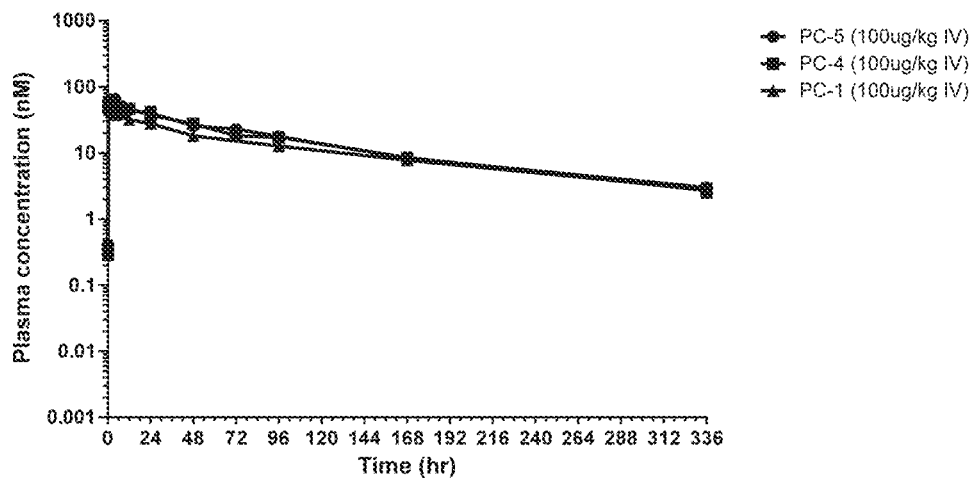
FIGS. 5A-5D illustrate pharmacokinetics of polypeptide PC-1, PC-2, PC-3, PC-7, PC-4, and PC-5 in cynomolgus monkey.
Figure 5B:
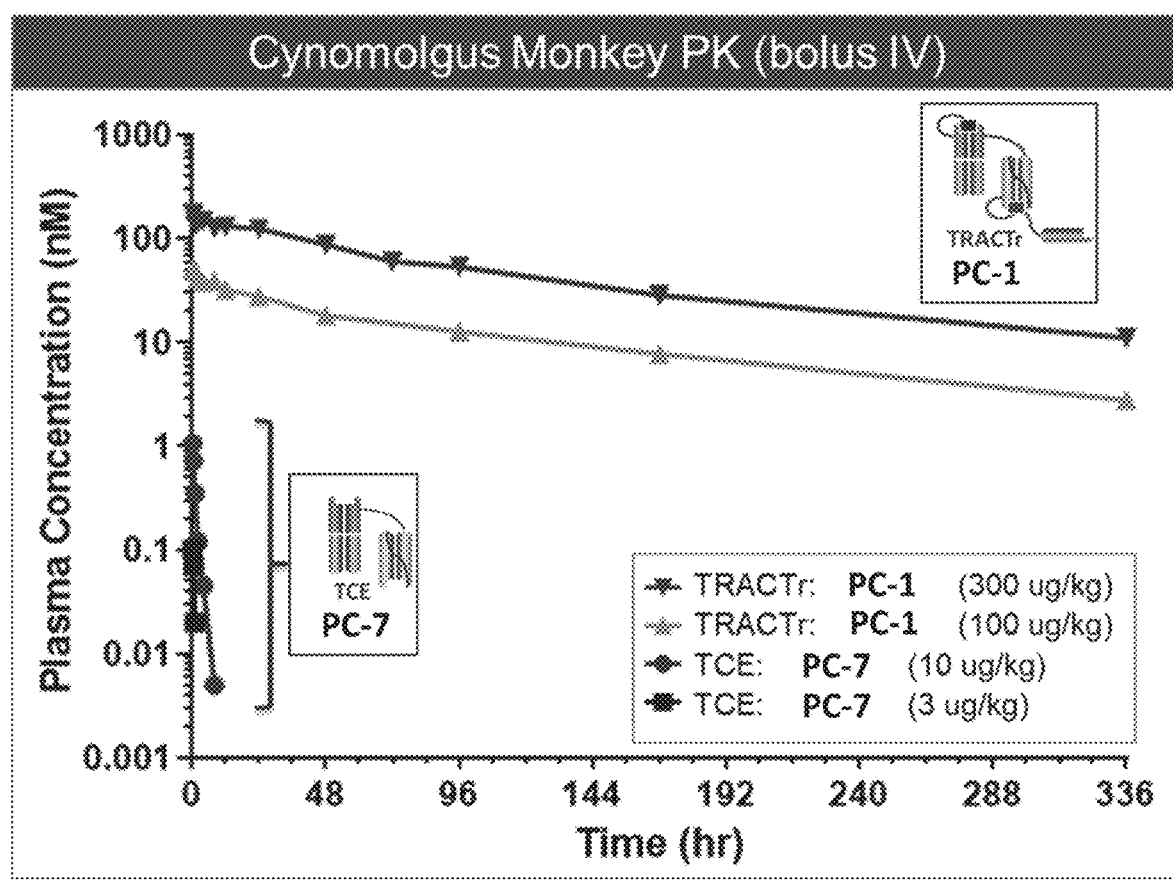
Figure 5C:
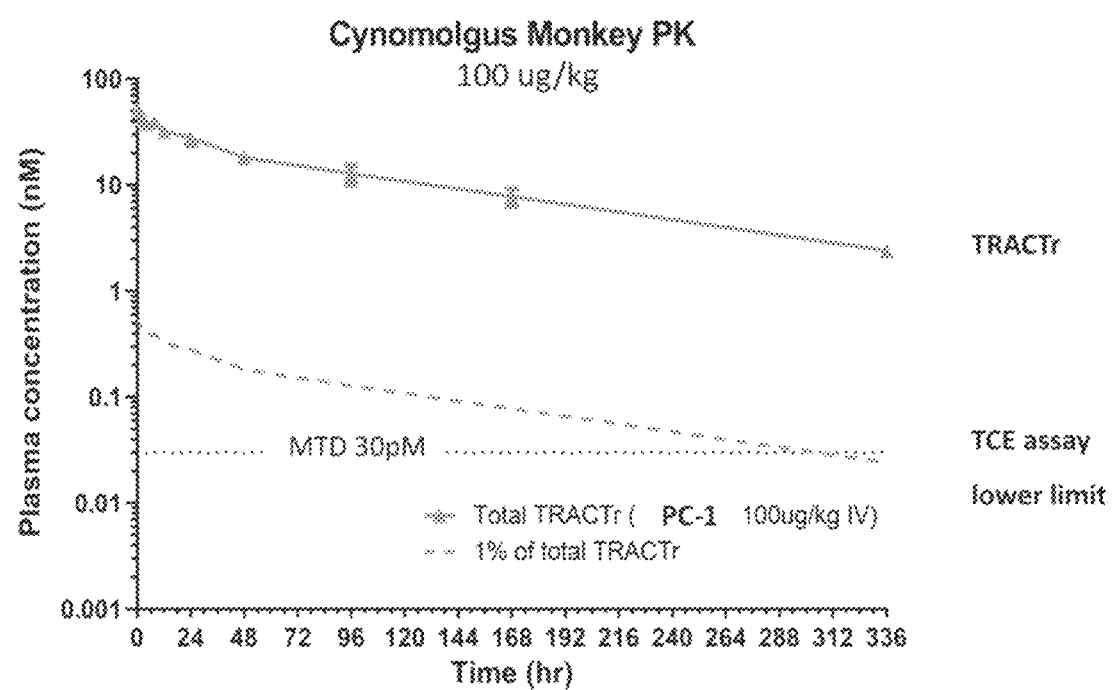
Figure 5D:
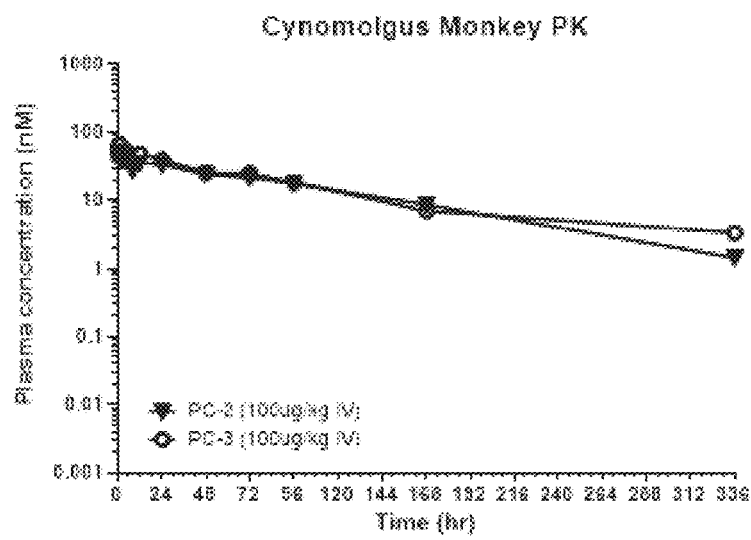
Figure 6A:
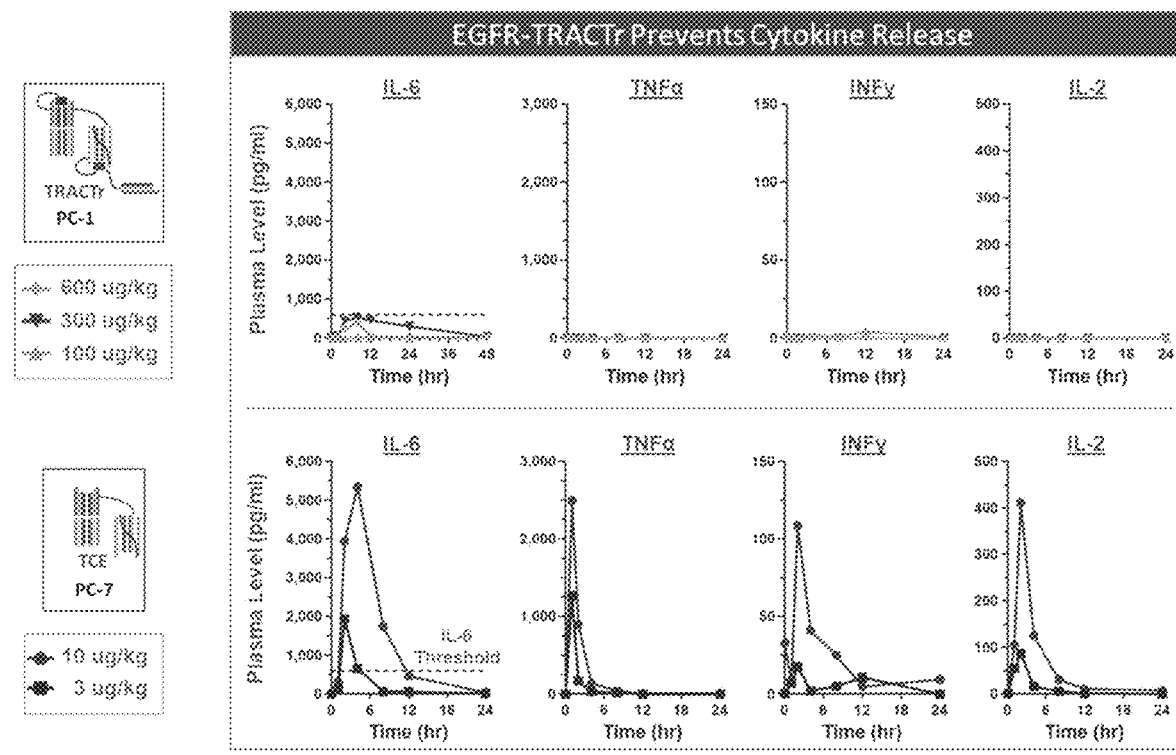
FIGS. 6A-6D illustrate cytokine release of polypeptide complexes PC-1, PC-2, PC-3, PC-7, PC-4, and PC-5 molecules in cynomolgus monkey.
Figure 6B:
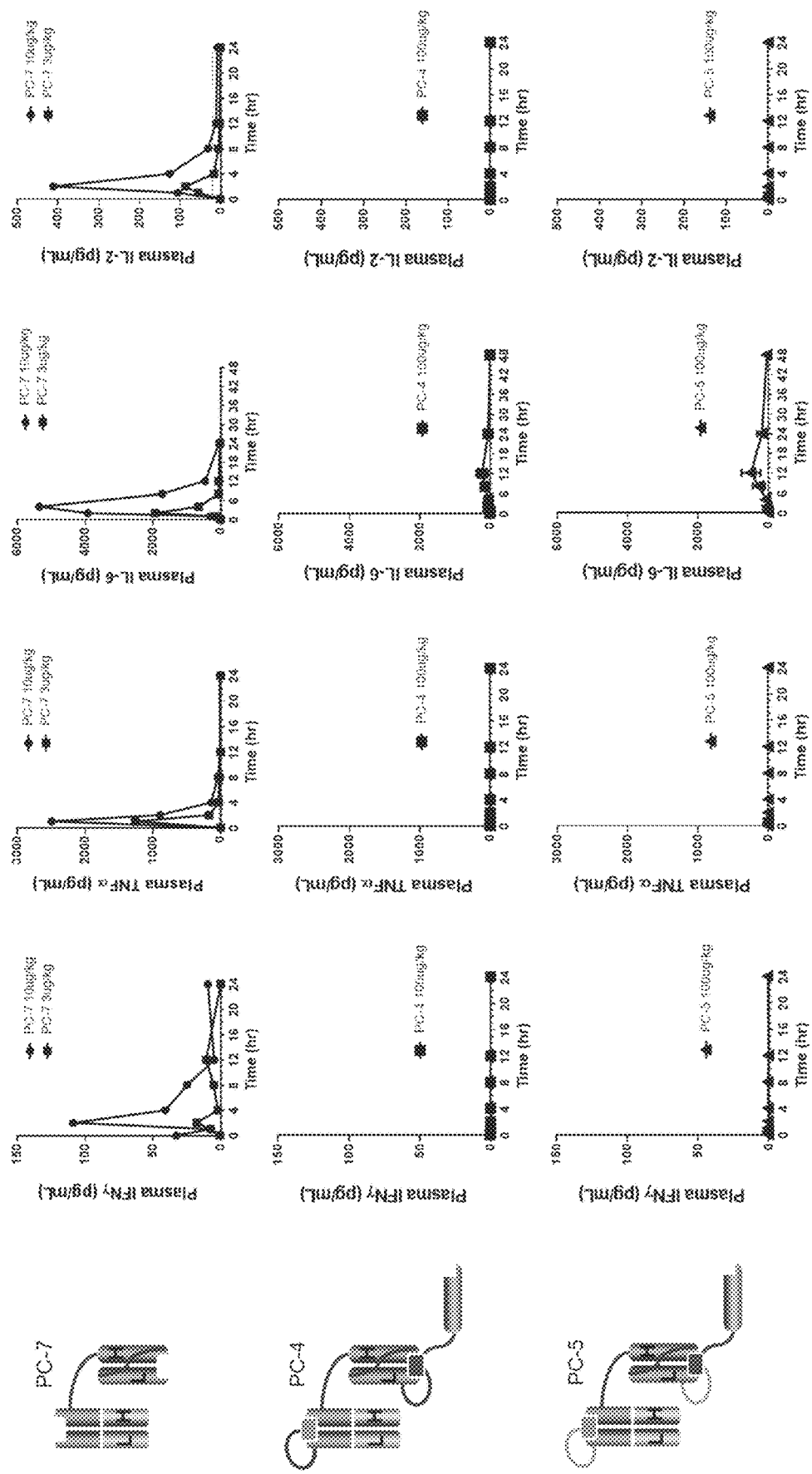
Figure 6C:
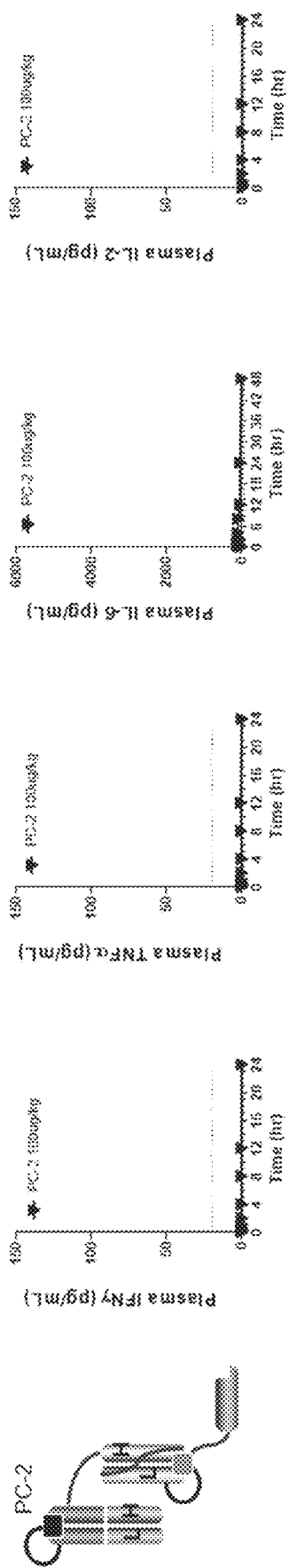
Figure 6D:
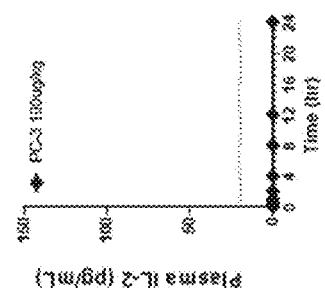
Figure 6D:
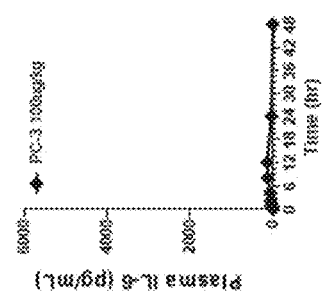
Figure 6D:
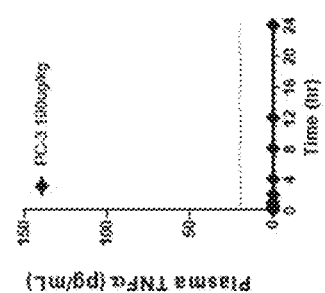
Figure 6D:
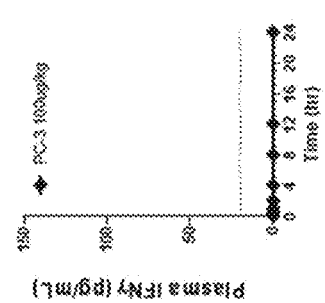
Figure 6D:
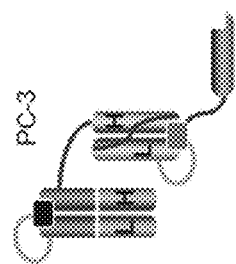

The polypeptide complexes binding was evaluated using enzyme linked immunosorbent assays (ELISAs). Biotinylated peptides were captured on neutravidin coated plates. A secondary antibody was used to detect bound polypeptide complex. Data for PC-2, PC-3, PC-4, PC-5, PC-1, and PC-6 comprising the mask and following cleavage of the mask is seen in FIGS. 3A-3B and EC50 binding data is summarized in Tables 13-14.

tions indicated. The data for PC-2, PC-3, PC-4, PC-5, PC-1, and PC-6 is seen in FIGS. 4A-4E and Tables 15-16.

TABLE 15

Tumor cell viability, IC50 (pM)

| Cytotox time | PC-6 | PC-1 | PC-2 | PC-3 | PC-4 | PC-5 | PC-2 + MTSP1 | PC-3 + MTSP1 | PC-4 + MTSP1 | PC-5 + MTSP1 |
|---|---|---|---|---|---|---|---|---|---|---|
| 24 hr | 1.13 | 555.6 | 326.6 | 578.3 | 539.9 | 869.4 | 0.2377 | 0.2811 | 0.3557 | 0.2294 |
| 48 hr | 0.4675 | 460.9 | 301.8 | 389.1 | 419.7 | 499.6 | 0.1998 | 0.1843 | 0.1596 | 0.2197 |
| 72 hr | 0.5507 | 763.5 | 389.3 | 444 | 522.6 | 588.6 | 0.2632 | 0.2402 | 0.218 | 0.3065 |
| 96 hr | 0.7548 | 1023 | 475.3 | 511.8 | 659.1 | 712.9 | 0.3296 | 0.3099 | 0.2809 | 0.394 |
| 120 hr |  |  | 577.5 | 589.6 | 773.2 | 824.2 | 0.3901 | 0.3679 | 0.3351 | 0.4737 |

TABLE 16

Tumor cell viability, Functional Shift

| Cytotox time | PC-6 | PC-1 | PC-2 | PC-3 | PC-4 | PC-5 | PC-2 + MTSP1 | PC-3 + MTSP1 | PC-4 + MTSP1 | PC-5 + MTSP1 |
|---|---|---|---|---|---|---|---|---|---|---|
| 24 hr | 1x | 491.7x | 289x | 511.8x | 477.8x | 769.4x | 0.2x | 0.2x | 0.3x | 0.2x |
| 48 hr | 1x | 985.9x | 645.6x | 832.3x | 897.8x | 1068.7x | 0.4x | 0.4x | 0.3x | 0.5x |
| 72 hr | 1x | 1386.4x | 706.9x | 806.2x | 949x | 1068.8x | 0.5x | 0.4x | 0.4x | 0.6x |
| 96 hr | 1x | 1355.3x | 629.7x | 678.1x | 873.2x | 944.5x | 0.4x | 0.4x | 0.4x | 0.5x |
| 120 hr |  |  | 765.1x | 781.1x | 1024.4x | 1091.9x | 0.5x | 0.5x | 0.4x | 0.6x |

TABLE 13

| EC50 nM | Masked | Cleaved | Shift |
|---|---|---|---|
| PC-2 | 21.29 | 0.13 | 169.5 |
| PC-3 | 23.47 | 0.12 | 198.2 |
| PC-4 | 20.59 | 0.15 | 139.3 |
| PC-5 | 18.28 | 0.13 | 143.5 |
| PC-1 | 44.79 | — | 282.8 |
| PC-6 | — | 0.16 | — |

TABLE 14

| EC50 nM | Masked | Cleaved | Shift |
|---|---|---|---|
| PC-2 | 2.082 | 0.101 | 20.6x |
| PC-3 | 1.792 | 0.1007 | 17.8x |
| PC-4 | 2.439 | 0.119 | 20.5x |
| PC-5 | 2.665 | 0.121 | 22.0x |
| PC-1 | 4.598 | 0.1383 | 33.2x |
| PC-6 | — | 0.069 | — |

Example 3. Confirmation of Comparable T-Cell Shifts with Cleavable Linkers

The polypeptide complexes were next evaluated in functional in vitro tumor cell killing and related T cell activation studies.

Briefly, HCT116 cells were seeded onto 96 well tissue culture treated flat bottom plates and allowed to adhere overnight. The following day, culture medium and nonadherent cells were removed and replaced with fresh medium containing titrated the polypeptide complexes at concentrations indicated.

Example 4. In Vivo Cynomolgus Monkey PK Comparison

The polypeptide complexes were assessed for pharmacokinetic and safety in cynomolgus monkey.

Cynomolgus Monkeys

Young naïve male cynomolgus monkeys were paired housed by group and identified by unique body tattoo. All animals were acclimated to housing conditions for 3 days prior to the start of the study. Prior to initiation all animals had undergone a physical examination by the study veterinarian. Only animals that, in the opinion of the study veterinarian, were healthy and otherwise met the criteria were admitted to the study. Food was withheld overnight prior to dosing. Purina 5049 was provided daily in amounts appropriate for the size of the animal. Tap water was provided ad libitum via automatic watering device.

Pharmacokinetics

Polypeptide complex pharmacokinetics for polypeptide complexes PC-1, PC-2, PC-3, PC-4, and PC-5 were determined in naïve male cynomolgus monkeys weighing 2-3 kg. Briefly, two group housed monkeys were used per dosing group and allowed to acclimate to their surroundings prior to dosing. Animals were sedated with Ketamine HCL 10-20 mg/kg IM prior to dosing and bleeding. Concentrated test articles were diluted in sterile phosphate buffered saline and administered to animals at a quantity relative to the animals' mass in kg. The dose for each test article was administered intravenously at 1 mL/kg dosing volume. For dosing, the left and right limbs were clipped and prepped with alcohol. The saphenous vein was identified, and a standard catheter was placed for IV bolus infusion (in either the left or right limb). The test article dosing solution was attached to the catheter via syringe and the bolus infusion occurred via manual compression of the syringe.

For blood collections, animals were sedated using ketamine, the femoral triangle was prepared, and blood was collected from the femoral vein using a 22G 1.5 inch needle, vacutainer sheath, and collection tube. Following venipuncture, manual compression of the vein was maintained until hemostasis was achieved. Blood collections were based on weight of the animals and did not exceed AGI maximum bleeds as set forth by IACUC. Blood was collected in EDTA tubes and processed to plasma. The blood samples were centrifuged cold at 3000×g for 10 min to separate cells from plasma. The plasma supernatant was harvested and stored frozen prior to analysis.

The concentration of the polypeptide complexes in cyno plasma samples was determined by ELISA. Briefly, anti-histag capture antibody was coated directly on ELISA plates. Standard dilutions of polypeptide complex in cyno serum were used to generate a calibration curve to which animal PK test samples could be compared. Standards and test samples were added to the plate and incubated cold overnight. Several different dilutions of test samples were used to make sure signals landed within appropriate dynamic range of the standard curve. Plates were washed and incubated with an anti-human HRP detection antibody for a brief time. Plates were washed, developed, and stopped using standard ELISA techniques. Standard curves plotting absorbance at 450 nm versus known polypeptide complex concentration were used to calculate the concentration of unknown test articles in each mouse PK plasma sample. Concentration of polypeptide complexes were plotted versus time and fit to a standard two stage distribution and elimination pharmacokinetic model. The calculated pharmacokinetic and parameters for polypeptide complexes PC-1, PC-7, PC-4, and PC-5 from cynomolgus monkey are shown in FIGS. 5A-5D and Tables 17-20.

TABLE 17

| Construct | Dose (ug/kg) | $C_{max}$ (nM) | $T_{1/2}$ (hr) | Vd (L) | CL (ml/h/kg) | $AUC_{(0 \to d7)}$ (nM · min) |
|---|---|---|---|---|---|---|
| PC-1 | 100 | 51 | 100 | 0.06 | 0.14 | 165,895 |
| PC-2 | 100 | | | | | |
| PC-3 | 100 | | | | | |
| PC-4 | 100 | 48 | 91 | 0.07 | 0.16 | 221,875 |
| PC-5 | 100 | 61 | 97 | 0.05 | 0.12 | 244,051 |

TABLE 18

Cyno PK Parameters

| Construct | Dose (ug/kg) | $C_{max}$ (nM) | $T_{1/2}$ (hr) | Vd (L) | CL (ml/h/kg) |
|---|---|---|---|---|---|
| PC-1 | 300 | 153 | 109 | 0.06 | 0.13 |
| PC-1 | 100 | 51 | 100 | 0.06 | 0.14 |
| PC-7 | 10 | 1.7 | 1.2 | 0.24 | 47 |
| PC-7 | 3 | 0.17 | 0.3 | 0.68 | 491 |

TABLE 19

| Construct | Dose (ug/kg) | $C_{max}$ (nM) | $T_{1/2}$ (hr) | Vd (L) | CL (ml/h/kg) |
|---|---|---|---|---|---|
| PC-1 | 100 | 51 | 100 | 0.06 | 0.14 |

TABLE 20

| Parameter | PC-2 100 ug/kg | PC-3 100 ug/kg | Units |
|---|---|---|---|
| CMAX | 40.37 | 53.78 | nM |
| t1/2 | 69.44 | 104.57 | hr |

TABLE 20-continued

| Parameter | PC-2 100 ug/kg | PC-3 100 ug/kg | Units |
|---|---|---|---|
| Vd | 0.08 | 0.06 | L |
| VSS | 0.06 | 0.11 | L |
| CL | 0.26 | 0.13 | mL/hr/kg |
| BW | 3.00 | 3.00 | kg |
| 7 day AUC | 207834 | 305952 | nM · min |

The data shows that the polypeptide complexes comprising the cleavable linkers exhibit prolonged serum half-life in cynomolgus monkeys.

Example 5. In Vivo Cynomolgus Monkey Cytokine Release

Cytokine release was measured in cynomolgus monkeys.

Cytokines present in plasma post treatment were measured using the non-human primate Th1/Th2 cytometric bead array assay kit from BD Biosciences (Cat no. 557800) according to the manufacturer's instructions. Data is shown in FIGS. 6A-6D and Table 21.

TABLE 21

| Property | PC-7 | PC-7 | PC-1 | PC-2 | PC-3 | PC-4 | PC-5 |
|---|---|---|---|---|---|---|---|
| | 3 ug/kg | 10 ug/kg | | 100 ug/kg | | | |
| | Plasma Cytokine Levels (Cmax pg/ml) | | | | | | |
| IL-6 | 1,932 | 5,352 | BQL | TBD | TBD | 234 | 493 |
| TNFα | 1,267 | 2,497 | BQL | TBD | TBD | BQL | BQL |
| IFNγ | BQL | 109 | BQL | TBD | TBD | BQL | BQL |
| IL-2 | 87 | 412 | BQL | TBD | TBD | BQL | BQL |

Example 6. In Vivo Cynomolgus Monkey Liver ALT/AST

Figure 7A:
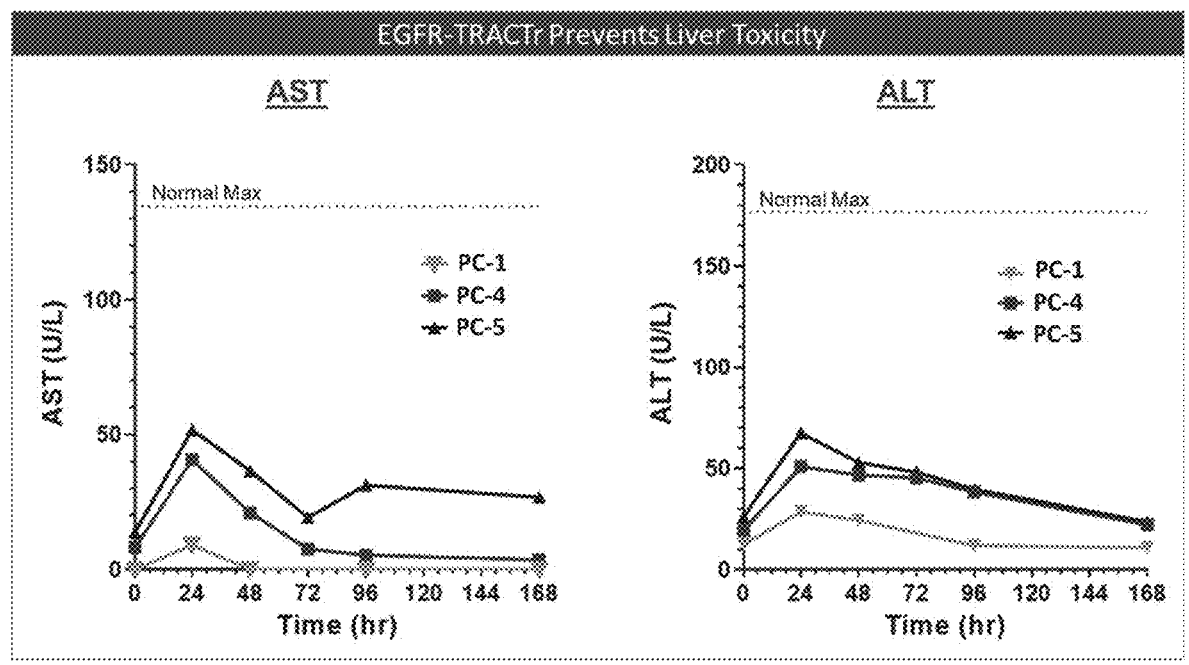
FIG. 7A-7B illustrates graphs of AST and ALT levels of polypeptide complexes PC-1, PC-2, PC-3, PC-4, and PC-5 in cynomolgus monkey.
Figure 7B:
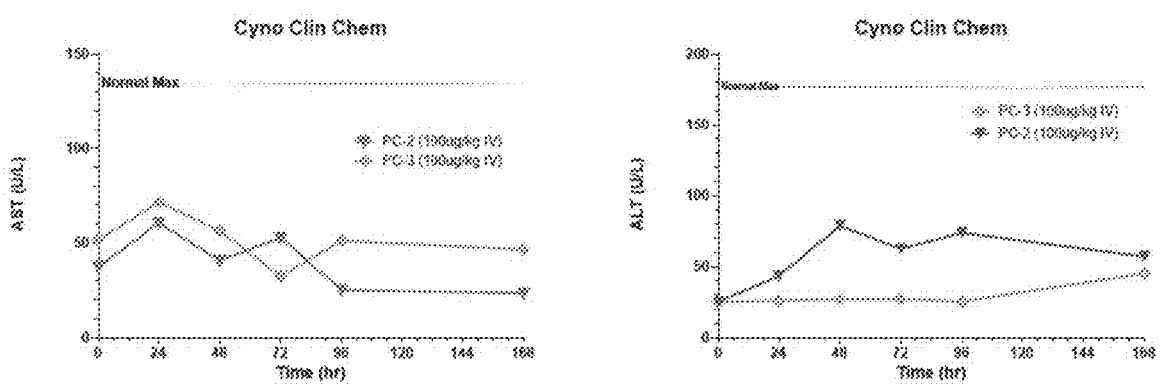

ALT/AST levels were measured. As seen in FIGS. 7A and 7B and Table 22, polypeptide complexes prevented liver toxicity in cynomolgus monkeys.

TABLE 22

| Property | PC-1 | PC-2 | PC-3 | PC-4 | PC-5 |
|---|---|---|---|---|---|
| | | | 100 ug/kg | | |
| | Plasma Levels (U/L) | | | | |
| ALT | 18 | TBD | TBD | 40 | 41 |
| AST | 9 | TBD | TBD | 40 | 51 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An isolated polypeptide comprising a cleavable linker according to the amino acid sequence of SEQ ID NO: 6 (LSGRSDAGSPLGLAG).

2. The isolated polypeptide of claim 1, wherein the cleavable linker is cleavable by a protease.

3. The isolated polypeptide of claim 2, wherein the protease comprises a tumor specific protease.

4. The isolated polypeptide of claim 2, wherein the protease comprises a matrix metalloprotease (MMP) or a serine protease.

5. The isolated polypeptide of claim 4, wherein the matrix metalloprotease comprises MMP2, MMP7, MMP9, MMP13, or MMP14.

6. The isolated polypeptide of claim 4, wherein the serine protease comprises matriptase, urokinase, or hepsin.

7. The isolated polypeptide of claim 1, wherein the isolated polypeptide further comprises an antigen binding domain that binds to a target antigen.

8. The isolated polypeptide of claim 7, wherein the antigen binding domain is C-terminal to the cleavable linker.

9. The isolated polypeptide of claim 7, wherein the cleavable linker connects a peptide to the antigen binding domain that binds to the target antigen in a configuration according to Formula I: $A_1$-$L_1$-$P_1$ wherein $A_1$ comprises the antigen binding domain that binds to the target antigen; $L_1$ comprises the cleavable linker; $P_1$ comprises a peptide that impairs binding of the antigen binding domain to the target antigen.

10. The isolated polypeptide of claim 9, wherein $P_1$ is connected N-terminal to the cleavable linker and $A_1$ is connected C-terminal to the cleavable linker.

11. The isolated polypeptide of claim 9, wherein $P^1$ has less than 70% sequence homology to the target antigen.

12. The isolated polypeptide of claim 9, wherein $P_1$ comprises a peptide sequence of at least 10 amino acids in length and no more than 20 amino acids in length.

13. The isolated polypeptide of claim 9, wherein $P_1$ is further linked to a half-life extending moiety.

14. The isolated polypeptide of claim 13, wherein the half-life extending moiety is a single-domain antibody.

15. The isolated polypeptide of claim 9, wherein $A^1$ comprises an antibody, a single chain variable fragment (scFv), a heavy chain variable domain (VH domain), a light chain variable domain (VL domain), a variable domain (VHH) of a camelid derived single domain antibody, a Fab, a Fab', a Fab light chain polypeptide, or a Fab heavy chain polypeptide.

16. The isolated polypeptide of claim 15, wherein $A^1$ comprises the scFv.

17. The isolated polypeptide of claim 16, wherein the scFv comprises an anti-CD3e single chain variable fragment.

18. A complex comprising the isolated polypeptide of claim 7 and a second isolated polypeptide comprising a second antigen binding domain.

19. The isolated polypeptide of claim 18, wherein the second isolated polypeptide is in a configuration according to Formula II: $A_2$-$L_2$-$P_2$ wherein $A_2$ comprises the second antigen binding domain; $L_2$ comprises a second cleavable linker; $P_2$ comprises a second peptide that impairs binding of the second antigen binding domain to a second target antigen; wherein the second antigen binding domain comprises a Fab light chain polypeptide or a Fab heavy chain polypeptide and the second target antigen comprises a tumor antigen.

20. The isolated polypeptide of claim 19, wherein the second cleavable linker comprises the amino acid sequence of SEQ ID NO: 1 (LSGRSDAG).

21. The isolated polypeptide of claim 19, wherein the second cleavable linker comprises the amino acid sequence of SEQ ID NO: 3 (ISSGLLSGRSDAG).

22. The isolated polypeptide of claim 19, wherein the second cleavable linker comprises the amino acid sequence of SEQ ID NO: 26 (AGLLAPPGGLSGRSDAG).

23. The isolated polypeptide of claim 19, wherein the second cleavable linker comprises the amino acid sequence of SEQ ID NO: 4 (AAGLLAPPGGLSGRSDAG).

24. The isolated polypeptide of claim 19, wherein the second cleavable linker comprises the amino acid sequence of SEQ ID NO: 5 (SPLGLSGRSDAG).

25. The isolated polypeptide of claim 19, wherein the second cleavable linker comprises the amino acid sequence of SEQ ID NO: 6 (LSGRSDAGSPLGLAG).

* * * * *

UNITED STATES PATENT AND TRADEMARK OFFICE
CERTIFICATE OF CORRECTION

PATENT NO. : 11,512,113 B2
APPLICATION NO. : 17/398500
DATED : November 29, 2022
INVENTOR(S) : David Campbell and Thomas R. DiRaimondo It is certified that error appears in the above-identified patent and that said Letters Patent is hereby corrected as shown below:

In the Claims

Column 93, Claim 11, Line 61, please replace 'P$^1$' with --P$_1$--;

Column 94, Claim 15, Line 31, please replace 'A$^1$' with --A$_1$--; and

Column 94, Claim 16, Line 38, please replace 'A$^1$' with --A$_1$--.

Signed and Sealed this
Twenty-first Day of February, 2023

Katherine Kelly Vidal
*Director of the United States Patent and Trademark Office*